(12) United States Patent
Taing et al.

(10) Patent No.: US 7,429,651 B2
(45) Date of Patent: *Sep. 30, 2008

(54) FLUORESCENT NUCLEOBASE CONJUGATES HAVING ANIONIC LINKERS

(75) Inventors: Meng Taing, San Mateo, CA (US); Shaheer H. Khan, Foster City, CA (US); Steven M. Menchen, Fremont, CA (US); Barnett B. Rosenblum, San Jose, CA (US)

(73) Assignee: Applera Corporation, Foster City, CA (US)

( * ) Notice: Subject to any disclaimer, the term of this patent is extended or adjusted under 35 U.S.C. 154(b) by 299 days.

This patent is subject to a terminal disclaimer.

(21) Appl. No.: 10/977,341

(22) Filed: Oct. 28, 2004

(65) Prior Publication Data

US 2005/0250119 A1    Nov. 10, 2005

Related U.S. Application Data

(63) Continuation of application No. 09/976,168, filed on Oct. 11, 2001, now Pat. No. 6,811,979.

(60) Provisional application No. 60/239,660, filed on Oct. 11, 2000.

(51) Int. Cl.
   *C07H 21/04* (2006.01)
(52) U.S. Cl. .................... 536/23.1; 536/24.3; 536/26.7; 536/26.8
(58) Field of Classification Search ................ 536/26.7, 536/26.8
   See application file for complete search history.

(56) References Cited

U.S. PATENT DOCUMENTS

| | | | |
|---|---|---|---|
| 4,795,699 A | 1/1989 | Tabor et al. | |
| 5,047,519 A | 9/1991 | Hobbs, Jr. et al. | |
| 5,558,991 A | 9/1996 | Trainor | |
| 5,986,086 A * | 11/1999 | Brush et al. | .............. 536/26.26 |
| 6,248,531 B1 | 6/2001 | Houthoff et al. | |
| 6,340,747 B1 | 1/2002 | Bazin et al. | |

FOREIGN PATENT DOCUMENTS

| | | |
|---|---|---|
| EP | 00731178 | 9/1996 |
| WO | WO9319078 | 9/1993 |
| WO | WO9611937 | 4/1996 |
| WO | WO9858942 | 12/1998 |
| WO | WO9918114 | 4/1999 |
| WO | WO9937810 | 7/1999 |
| WO | WO9940223 | 8/1999 |
| WO | WO0119841 | 3/2001 |

OTHER PUBLICATIONS

Confalone, J. Heterocyclic Chem., 1990, 27, 31-46.
Finn et al., Nucleic Acids Res., 2002, 30(13), 2877-2885.
Rosenblum B.B. et al., New dye-labeled terminators for improved DNA sequencing patterns, Nucleic Acids Research, 1997, 25 (22), 4500-4504.
Schoetzau et al., Perkin Trans. 1, J. Chem. Soc., 2000, 1411-1415.
Stolze et al., Helvetica Chimica Acta, 1999, 82, 1311-1323.
Yamaguchi et al., Nucleosides and Nucleotides, Oct. 19, 2001, 15, 607-618.

* cited by examiner

*Primary Examiner*—Kenneth R. Horlick
(74) *Attorney, Agent, or Firm*—Vincent P. Liptak; Shirley A. Recipon

(57) ABSTRACT

Provided are nucleotide-dye conjugates and related compounds in which a dye is linked to a nucleobase directly or indirectly by an anionic linker. The anionic character of the linker is provided by one or more anionic moieties which are present in the linker, such as phosphate, phosphonate, sulfonate, and carboxylate groups. When the dye is a provided as a donor/acceptor dye pair, the anionic linker can be located between the donor and the acceptor, or between the nucleobase and either the donor or acceptor, or both. In one embodiment, conjugates of the invention provide enhanced electrophoretic mobility characteristics to sequencing fragments, e.g., for dideoxy sequencing using labeled terminators.

10 Claims, 76 Drawing Sheets

10

+

11

12

13

14

15

23

10

30

27

31

32

32

14

33

35

7

10

28

39

40

27

40

44

Compound 15

56

50

57

58

28

59

60

27

61

62

62

63

64

66

7

73

7

76

77

94

81

95

100

101

102

103

+

11

104

105

14

106

120

+

71

123

76

124

134

+

11

135

136

14

137

143 + 145

146

R = CO₂H  147

14

FLUORESCENT NUCLEOBASE CONJUGATES HAVING ANIONIC LINKERS

CROSS-REFERENCE TO RELATED APPLICATIONS

This application is a continuation of U.S. patent application Ser. No. 09/976,168, filed Oct. 11, 2001, now U.S. Pat. No. 6,811,979, issued Nov. 2, 2004, which claims the benefit of application Ser. No. 60/239,660, filed Oct. 11, 2000, which are all incorporated herein by reference.

FIELD OF THE INVENTION

The present invention relates to fluorescent dye compounds, and to conjugates and uses thereof. The invention also relates to fluorescent polynucleotide conjugates having improved electrophoretic mobilities.

INTRODUCTION

The analysis of complex mixtures of polynucleotides is important in many biological applications. In many situations, it is necessary to separate components of such mixtures to detect target polynucleotides of interest, to determine relative amounts of different components, and to obtain nucleotide sequence information, for example.

Electrophoresis provides convenient methods for analyzing polynucleotides. Typically, polynucleotides can be separated on the basis of length, due to differences in electrophoretic mobility. For example, in a matrix such as crosslinked polyacrylamide, polynucleotides typically migrate at rates that are inversely proportional to polynucleotide length, due to size-dependent obstruction by the crosslinked matrix. In free solution, polynucleotides tend to migrate at substantially the same rates because of their substantially identical mass to charge ratios, so that it is difficult to distinguish different polynucleotides based on size alone. However, distinguishable electrophoretic mobilities can be obtained in free solution using polynucleotides that contain different charge/mass ratios, e.g., by attaching to the polynucleotides a polymer or other chemical entity having a charge/mass ratio that differs from that of the polynucleotides alone (e.g., see U.S. Pat. No. 5,470,705).

When different polynucleotides can be separated based on length or molecular weight, detection can usually be accomplished using a single detectable label, such as a radioisotope or fluorophore. However, in complex mixtures or when different-sequence polynucleotides have similar or identical mobilities, it is preferable to use two or more detectable labels to distinguish different polynucleotides unambiguously.

In DNA sequencing, it is now conventional to use two or more (usually four) different fluorescent labels to distinguish sequencing fragments that terminate with one of the four standard nucleotide bases (A, C, G and T, or analogs thereof). Such labels are usually introduced into the sequencing fragments using suitably labeled extension primers (dye-primer method) or by performing primer extension in the presence of nonextendable nucleotides that contain unique labels (Sanger dideoxy terminator method). Electrophoresis of the labeled products generates ladders of fragments that can be detected on the basis of elution time or band position.

Under sieving conditions in crosslinked or non-crosslinked matrices, shorter poly-nucleotide fragments migrate more rapidly than longer fragments. Usually, the inter-band spacing and migration rates of fragments decrease gradually in proportion to increasing length. However, anomalous migration patterns can occur due to sequence-dependent secondary structures within fragments, even in the presence of denaturing agents such as urea. For example, poly-G segments often cause band compression that make sequence determination of these regions difficult. Compressed band regions can often be resolved using nucleotide analogs such as dITP (2'-deoxyinosine-5'-triphosphate) or 7-deaza-dGTP in the extension reaction instead of dGTP, or by sequencing the complementary strand.

Anomalous migration patterns may also occur for polynucleotide fragments that contain a detectable label, due to interactions between the label and one or more bases in the polynucleotide. Such interactions can be particularly problematic when the interactions are sequence-dependent, so that different-sequence fragments having the same-lengths may have significantly different mobilities. This phenomenon can be inconvenient for sequencing, especially in automated sequencing methods. Accordingly, there is a need for labeled compounds and methods of use to improve electrophoretic performance.

SUMMARY OF THE INVENTION

In one aspect, the present invention provides a conjugate comprising a dye-labeled nucleobase of the form: (1) B-L-D, wherein B is a nucleobase, L is an anionic linker, and D comprises at least one fluorescent dye, or (2) B-L1-D1-L2-D2, wherein B is a nucleobase, L1 and L2 are linkers such that at least one of L1 and L2 is an anionic linker, and D1 and D2 are members of a fluorescent donor/acceptor pair, such that one of D1 and D2 is a donor dye capable of absorbing light at a first wavelength and emitting excitation energy in response thereto, and the other of D1 and D2 is an acceptor dye capable of absorbing the excitation energy emitted by the donor dye and fluorescing at a second wavelength in response thereto.

Each anionic linker may contain one or more anionic groups, such as a sulfonic acid moiety, a sulfate monoester, an anionic phosphate, an anionic phosphonate, or a carboxylic acid.

In one embodiment, L, L1 or L2 contains a phosphate diester moiety whose phosphorus atom is located within a chain of linker atoms (bridging position) or can be a substituent attached to a chain of linker atoms (non-bridging position). In another embodiment, the linker contains a monoanionic phosphonate ester which can be located within the linker chain or attached to the linker chain. Other embodiments are described further herein.

In embodiments in which the conjugate has the form B-L1-D1-L2-D2, one of L1 and L2 can be a nonanionic linker. In one embodiment, L1 is an anionic linker and L2 is non-anionic. For example, when L2 is non-anionic, D1-L2-D2 may comprise structure (a), (b) or (c) below:

  (a)

  (b)

  (c)

wherein: $R_{21}$ is $C_1$-$C_5$ alkyldiyl, $Z_1$, is NH, S, or O, $R_{22}$ is ethenediyl, ethynediyl, 1,3-butadienediyl, 1,3-butadiynediyl, a 5- or 6-membered ring having at least one unsaturated bond or a fused ring structure having at least one unsaturated bone, and $R_{28}$ is a bond or spacer group (a linking segment) that links R22 to D1 or D2. In another embodiment, L1 can be a nonionic linker, of which the following are examples:
—C≡CCH$_2$NH—, —C≡CCH$_2$NHC(O)(CH$_2$)$_5$NH—, —C≡CC(O)NH(CH$_2$)$_5$NH—, —C≡CCH₂OCH₂CH₂NH—,
—C≡CCH₂OCH₂CH₂OCH₂CH₂NH—, —C≡C—CH₂OCH₂CH₂—NH—, and —C≡C(p-C₄H₆)OCH₂CH₂NH—.

Fluorescent dyes used in accordance with the invention can include any fluorescent compound suitable for the purposes of the present invention. Typically, each dye comprises a conjugated, resonance-delocalized or aromatic ring system that absorbs light at a first wavelength and emits light at a second wavelength in response thereto. For example, the dyes can be selected independently from any of a variety of classes of fluorescent compounds, such as xanthene, rhodamine, dibenzorhodamine, fluorescein, [8,9]benzophenoxazine, cyanine, phthalocyanine, squaraine, or bodipy dye.

In another aspect, the invention includes a labeled nucleoside triphosphate comprising a conjugate of the type described herein. In one embodiment, the labeled nucleoside triphosphate is not 3'-extendable. For example, the labeled nucleoside triphosphate can be a 2',3'-dideoxynucleotide or 3'-fluoro-2',3'-dideoxynucleotide. In another embodiment, the labeled nucleoside triphosphate is extendable and contains a 3'-hydroxyl group.

In another aspect, the invention includes a polynucleotide comprising a conjugate of the type discussed herein. In one embodiment, the conjugate is located in a 3' terminal nucleotide subunit of a polynucleotide, such that the subunit may be extendable or nonextendable. In another embodiment, the conjugate is located on a non-terminal nucleotide subunit.

In a further embodiment, the invention provides a mixture comprising a plurality of different-sequence polynucleotides, wherein at least one polynucleotide contains a conjugate as described herein. In one embodiment, the mixture comprises at least two different-sequence polynucleotides which each contain a different conjugate to identify the attached polynucleotide. In another embodiment, the mixture comprises four classes of polynucleotides, wherein the polynucleotides in each class terminate with a different terminator subunit type that contains a distinct nucleobase-dye conjugate to identify the polynucleotides in that class.

The invention also includes a method of identifying one or more polynucleotide(s). In the method, one or more labeled different-sequence polynucleotides are formed such that each different-sequence polynucleotide contains a unique conjugate as described herein. The one or more labeled different-sequence polynucleotides are separated by electrophoresis on the basis of size, and one or more different-sequence polynucleotides are identified on the basis of electrophoretic mobilities and fluorescence properties.

The invention also provides a method of forming a labeled polynucleotide strand, the method comprising reacting together (i) a duplex polynucleotide comprising a 3'-extendable strand hybridized to a complementary template strand having a 5' overhang, (ii) a template-dependent polymerase enzyme, and (iii) a labeled nucleoside triphosphate containing a conjugate as described herein, under conditions effective to form a labeled polynucleotide containing the conjugate. In one embodiment, the labeled nucleoside triphosphate is nonextendable. In another embodiment, the labeled nucleoside triphosphate is extendable.

The invention also provides a method of sequencing a target polynucleotide sequence. In the method, four classes of polynucleotides are formed which are complementary to a target polynucleotide sequence, by template-dependent primer extension, wherein the polynucleotides in each class terminate with a different terminator subunit type that contains a distinct nucleobase-dye conjugate to identify the polynucleotides in that class. The resultant polynucleotides are separated on the basis of size to obtain a mobility pattern from which the sequence of the target polynucleotide sequence can be determined.

The invention also provides kits for performing the various methods of the invention. For nucleic acid sequencing, the kit comprises at least one labeled nucleoside triphosphate comprising a conjugate described herein. The kit may also include one or more of the following components: a 3'-extendable primer, a polymerase enzyme, one or more 3' extendable nucleotides which are not labeled with conjugate, and/or a buffering agent. In some embodiments, the kit includes at least one labeled nucleoside triphosphate that is nonextendable. In other embodiments, the kit comprises four different labeled nucleoside triphosphates which are complementary to A, C, T and G, and each of which contains a distinct conjugate as described herein. In yet another embodiment, the labeled nucleoside triphosphates are nonextendable. In another embodiment, the labeled nucleoside triphosphates are extendable ribonucleoside triphosphates. In another embodiment, the kit comprises at least one labeled, nonextendable nucleoside triphosphate comprising a conjugate described herein, and one or more of the following components: a 3'-extendable primer, a polymerase enzyme, and/or a buffering agent.

These and other objects and features of the invention will become more apparent from the detailed description.

DETAILED DESCRIPTION

Figure 1A:
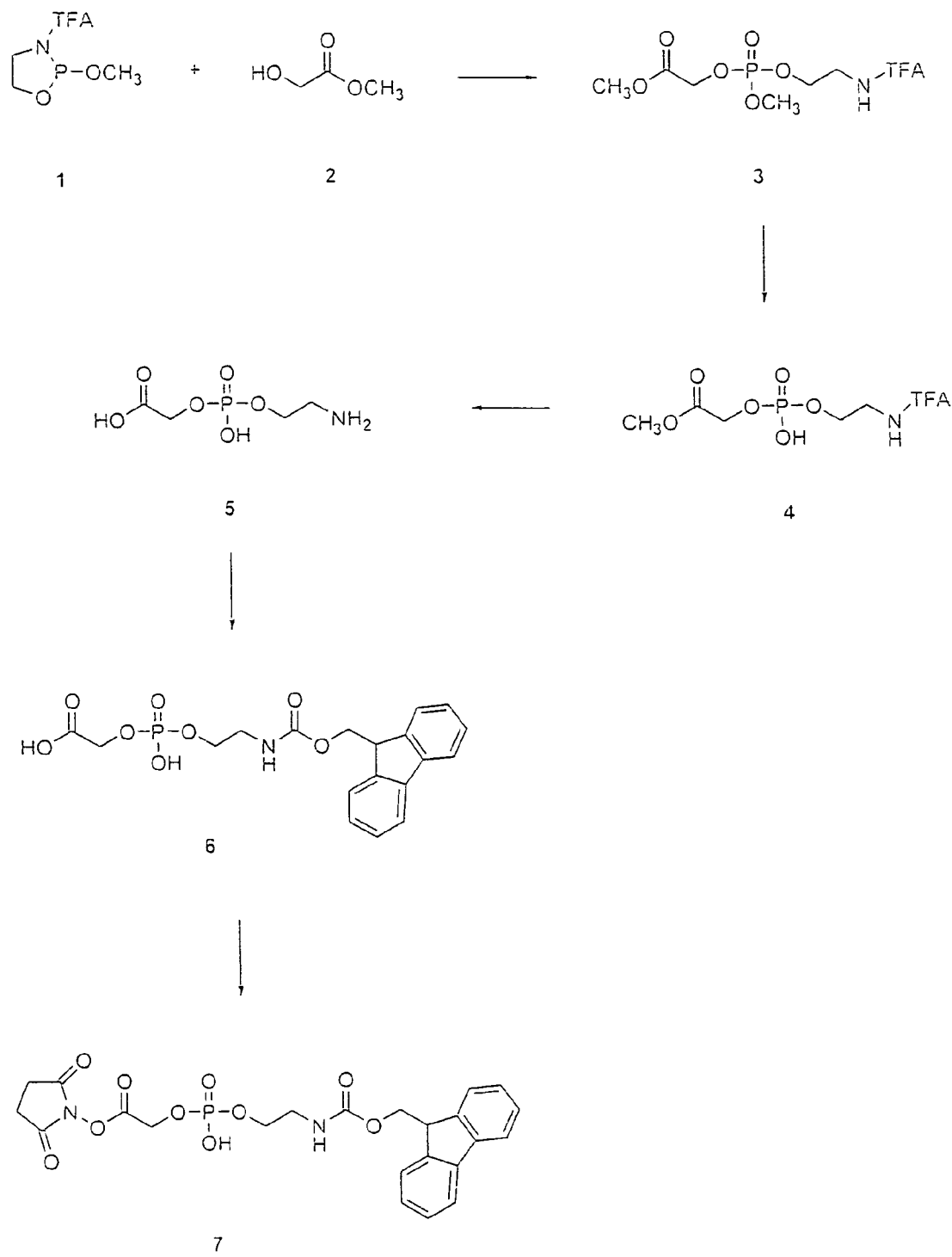
FIGS. 1A-18B and 22A-22B illustrate exemplary synthetic protocols for preparing various conjugates in accordance with the invention.
Figure 1B:
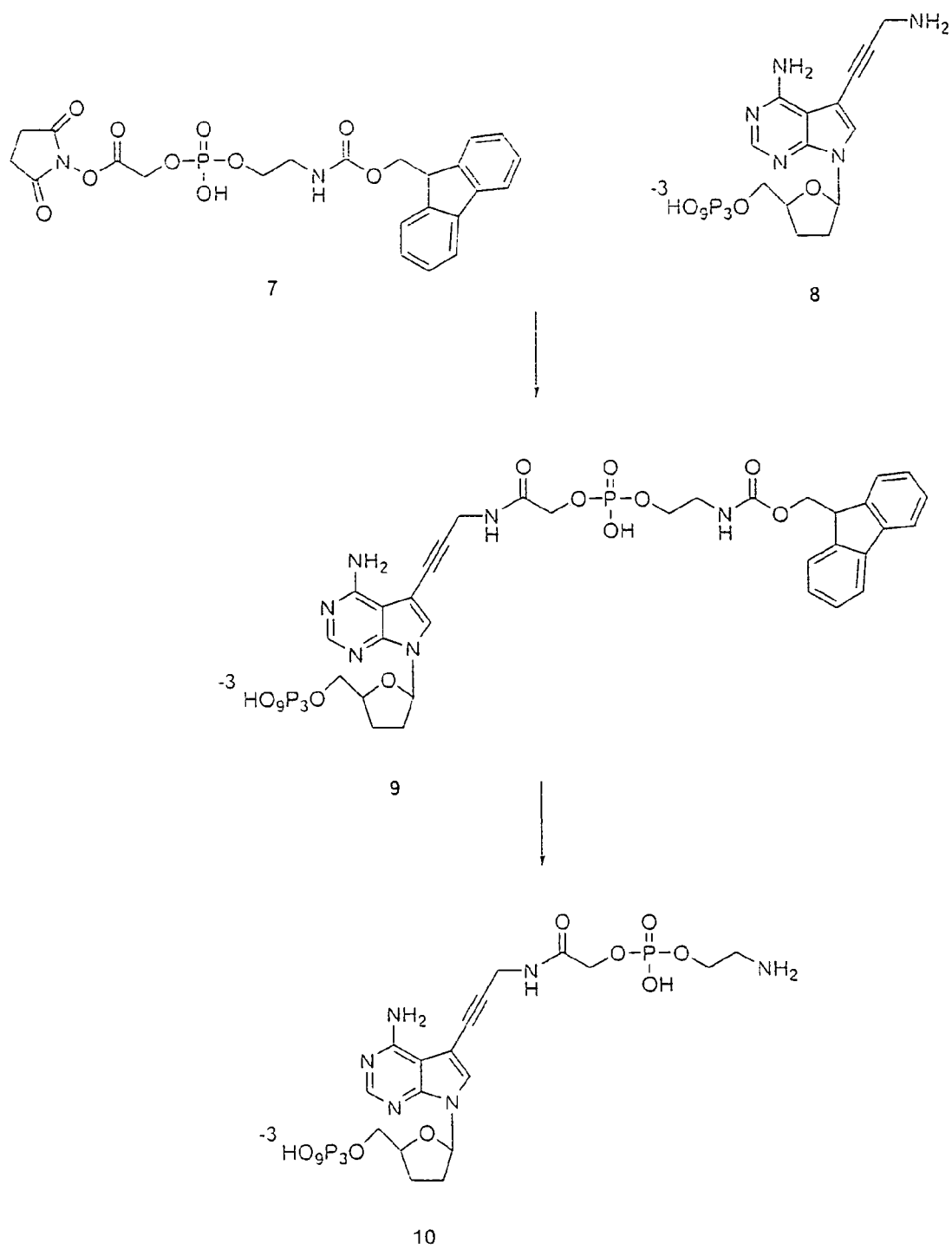
Figure 1C:
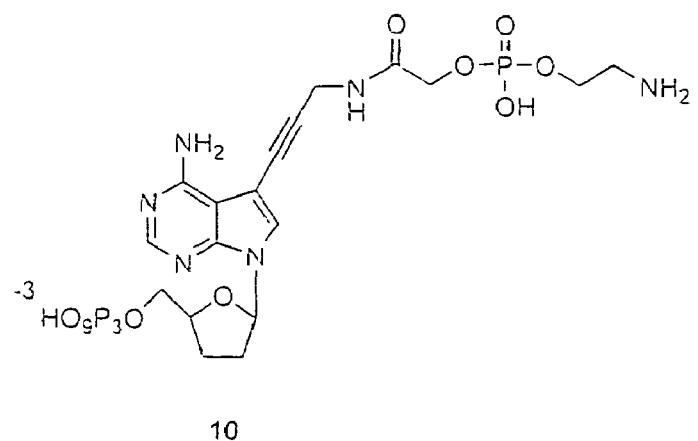
Figure 1C:
Figure 1C:
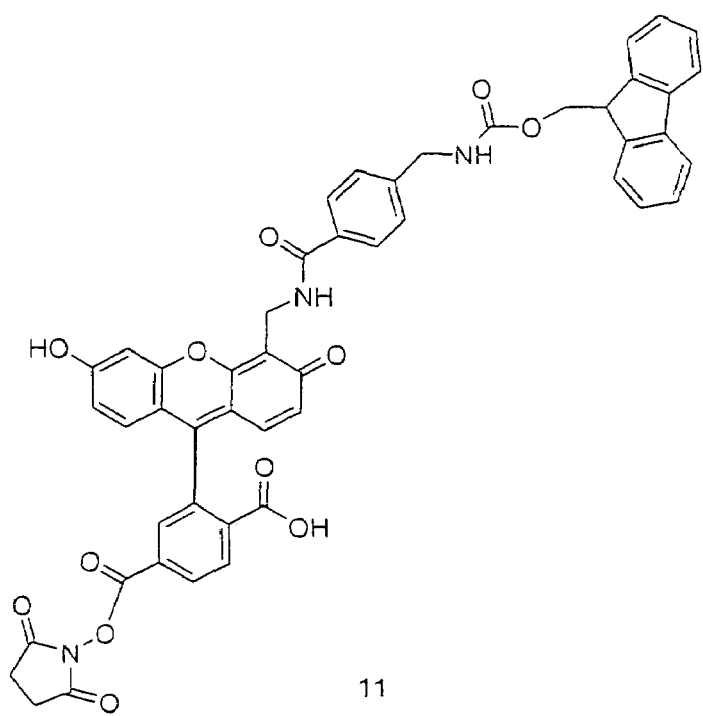
Figure 1C:
Figure 1D:
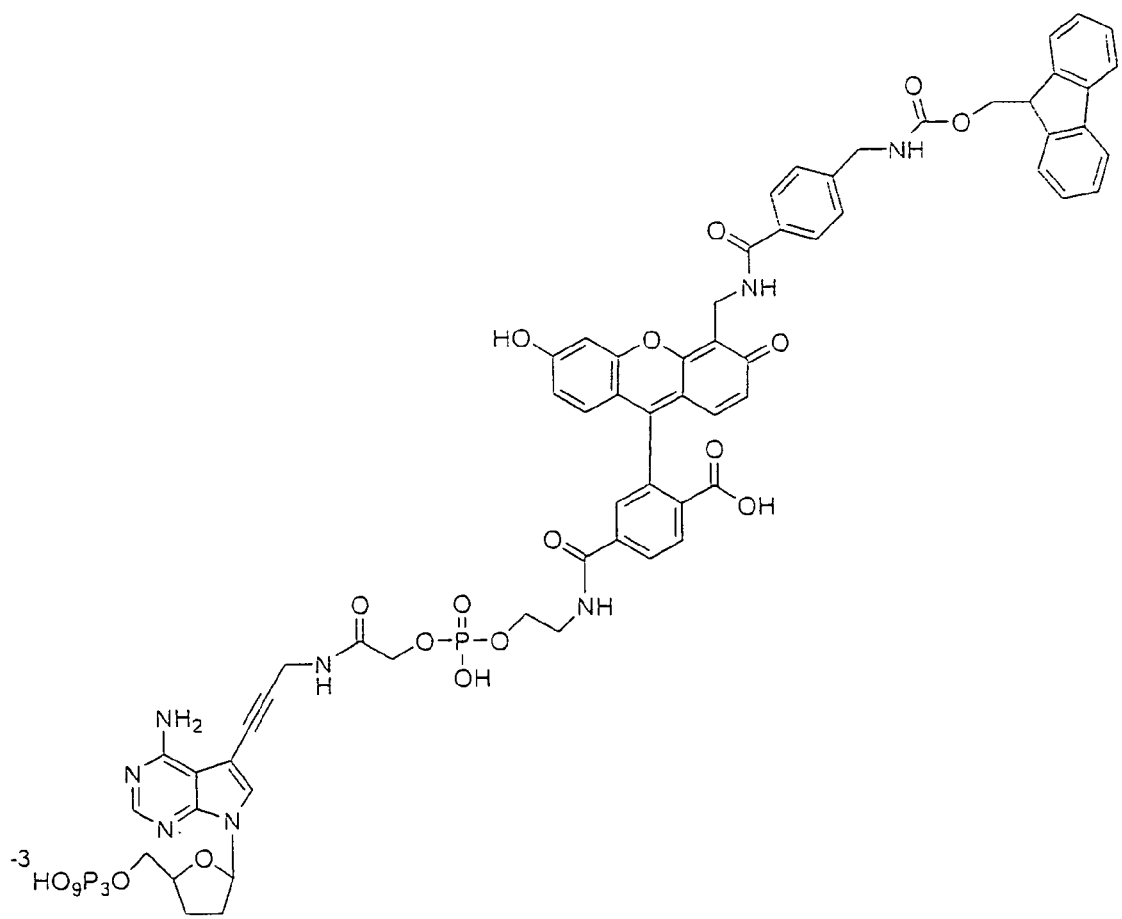
Figure 1D:
Figure 1E:
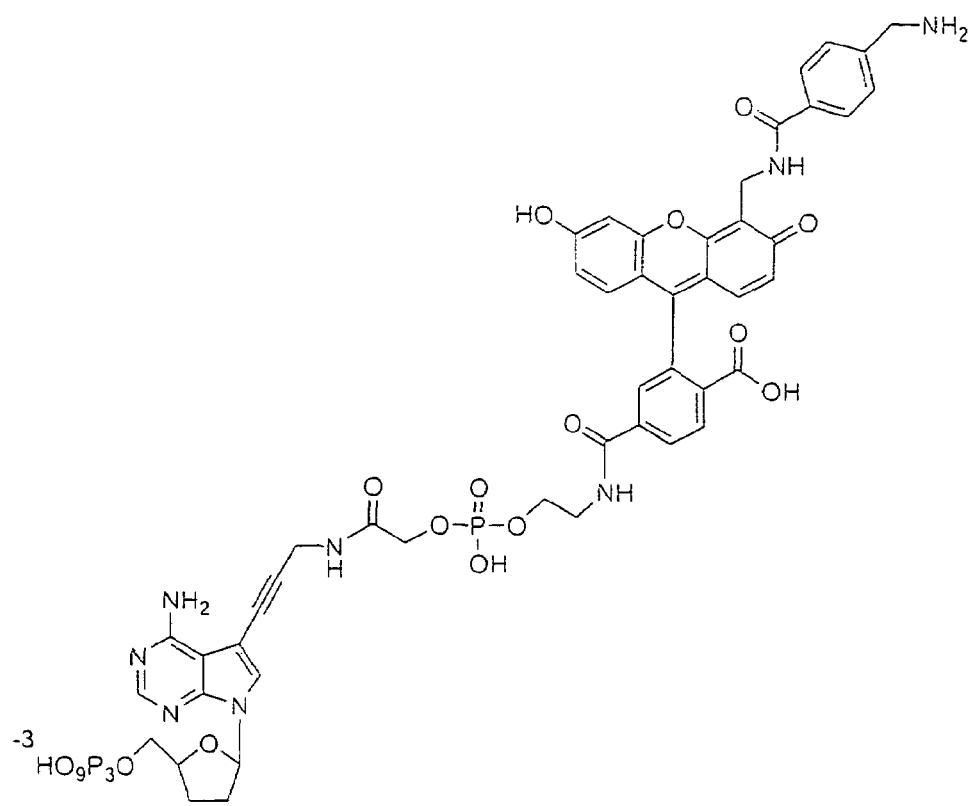
Figure 1E:
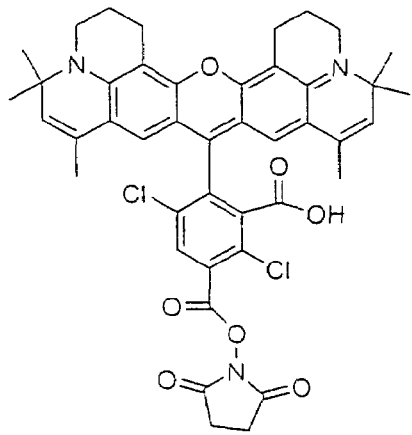
Figure 1F:
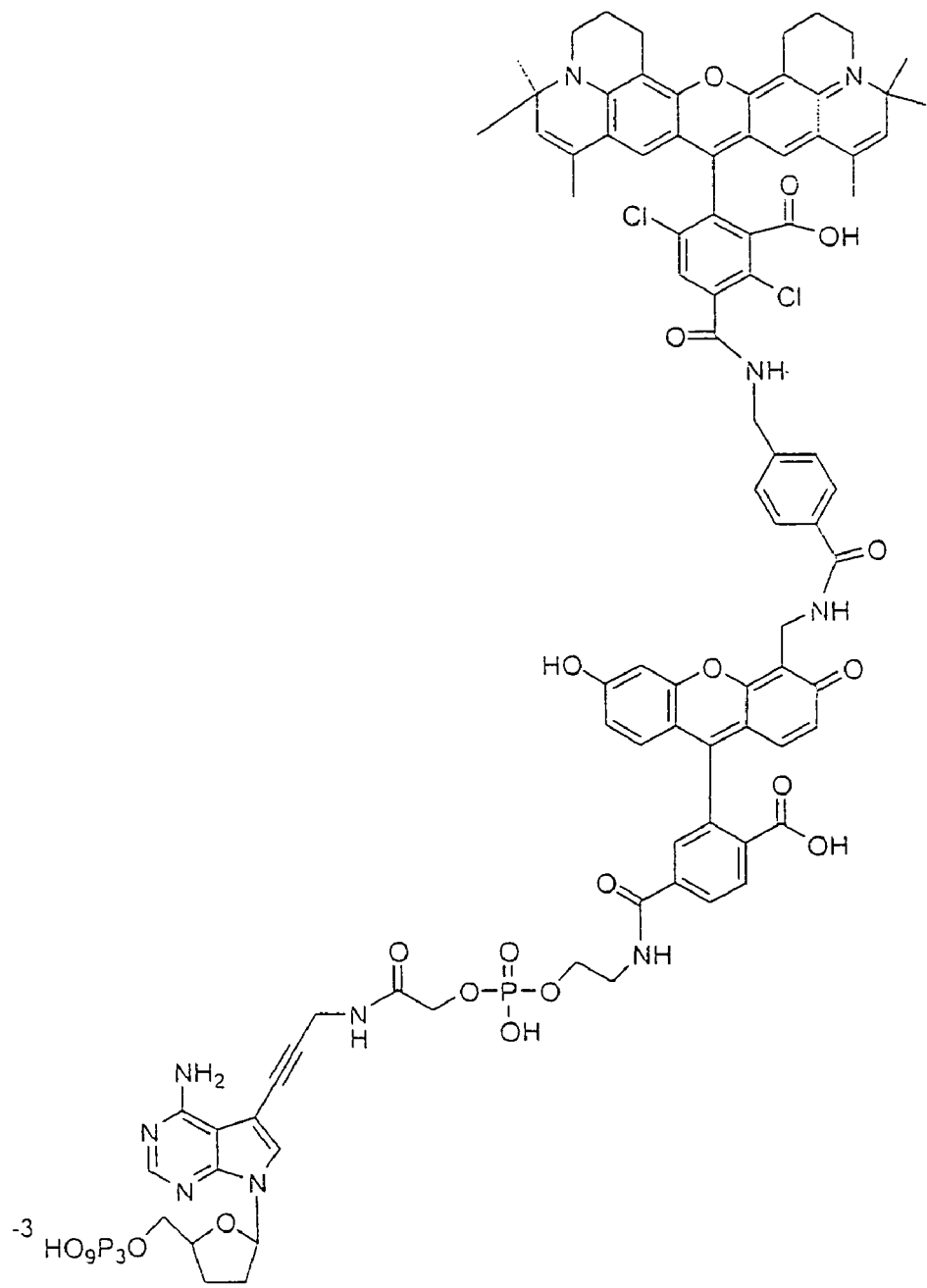
Figure 2A:
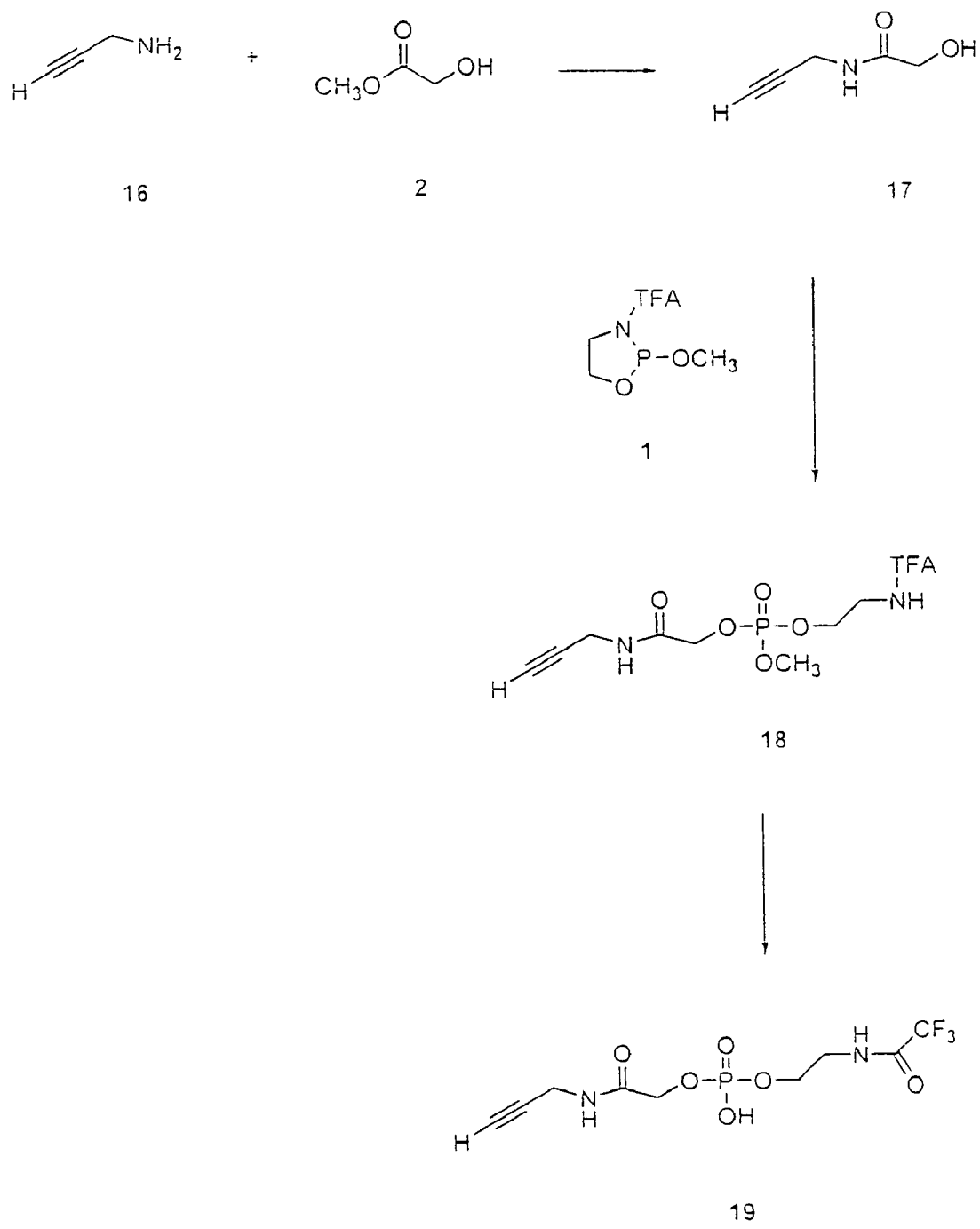
Figure 2B:
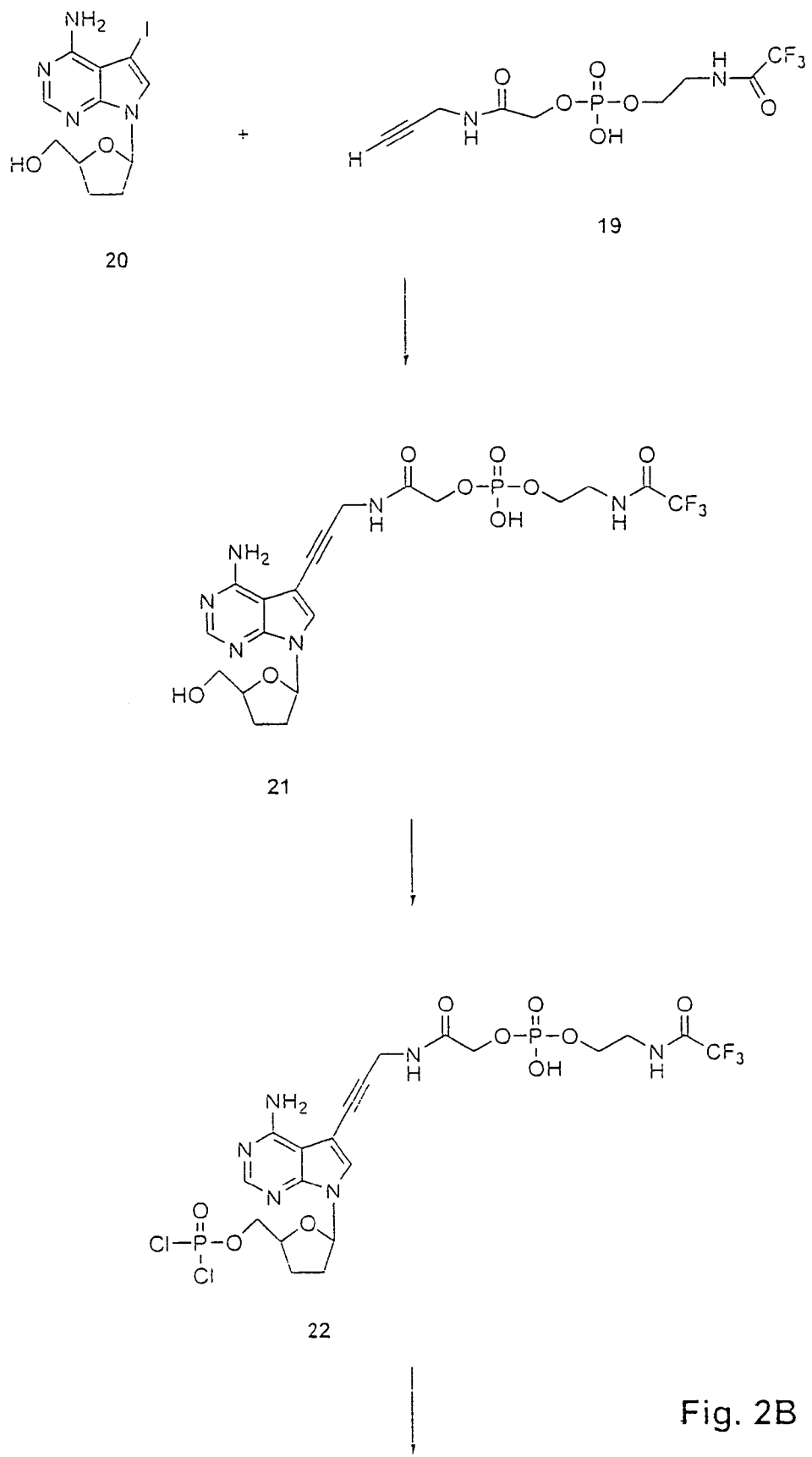
Figure 2C:
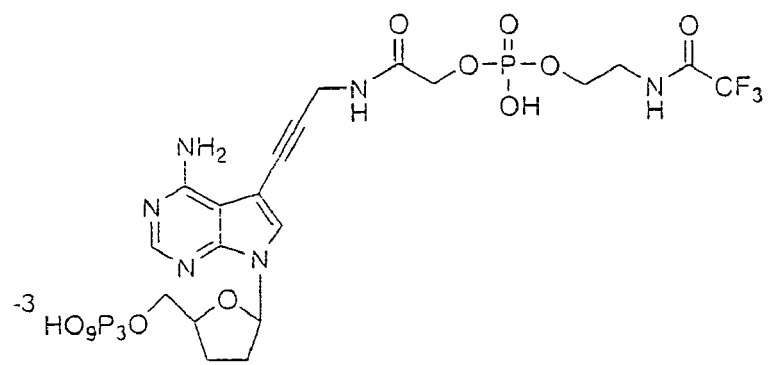
Figure 2C:
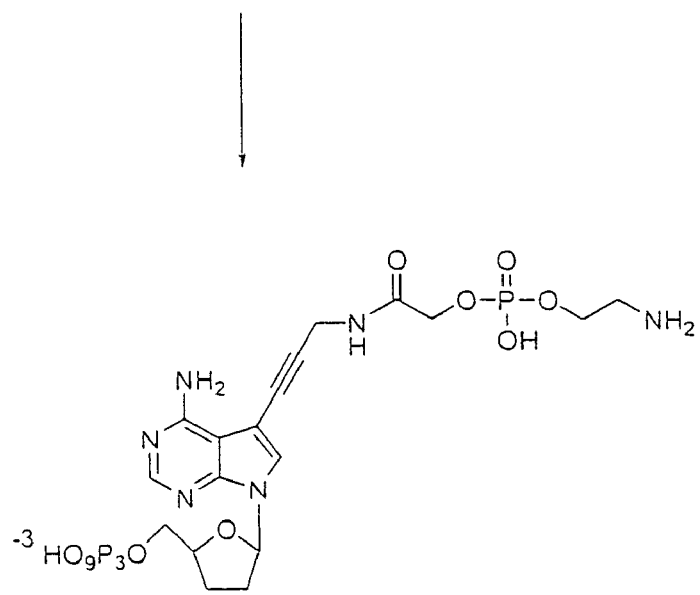
Figure 3A:
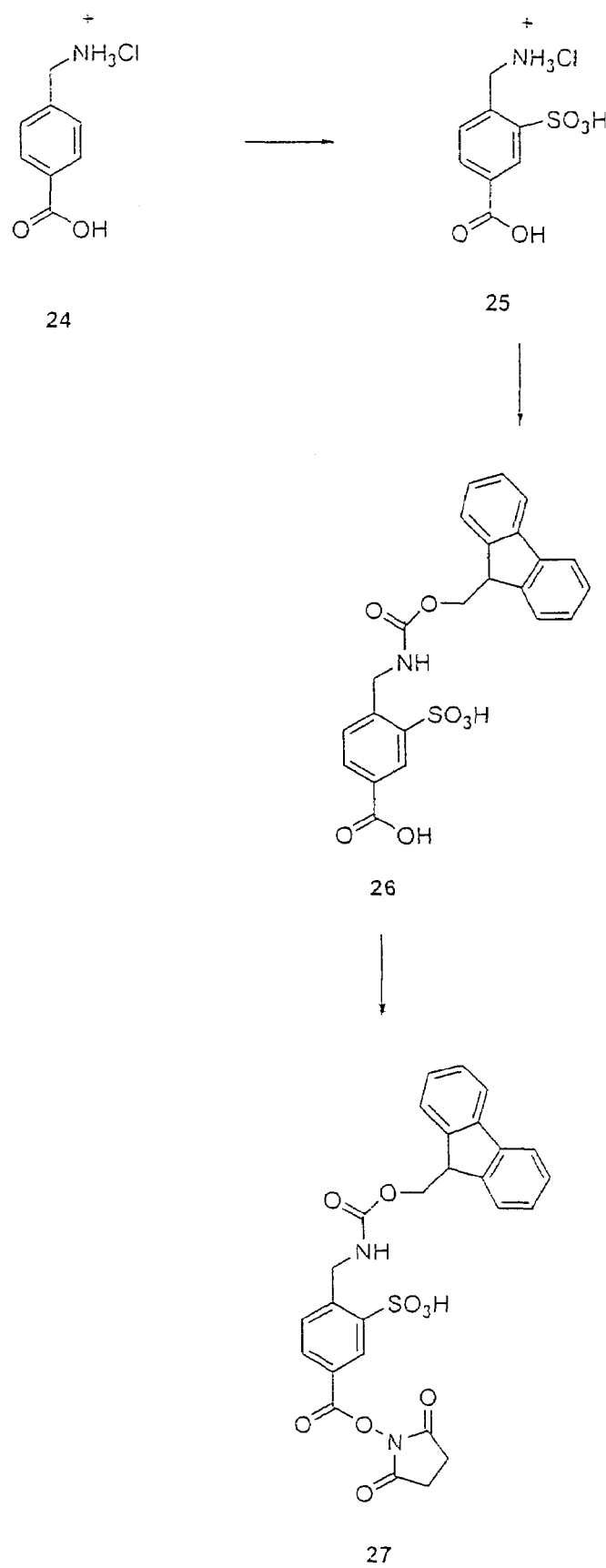
Figure 3B:
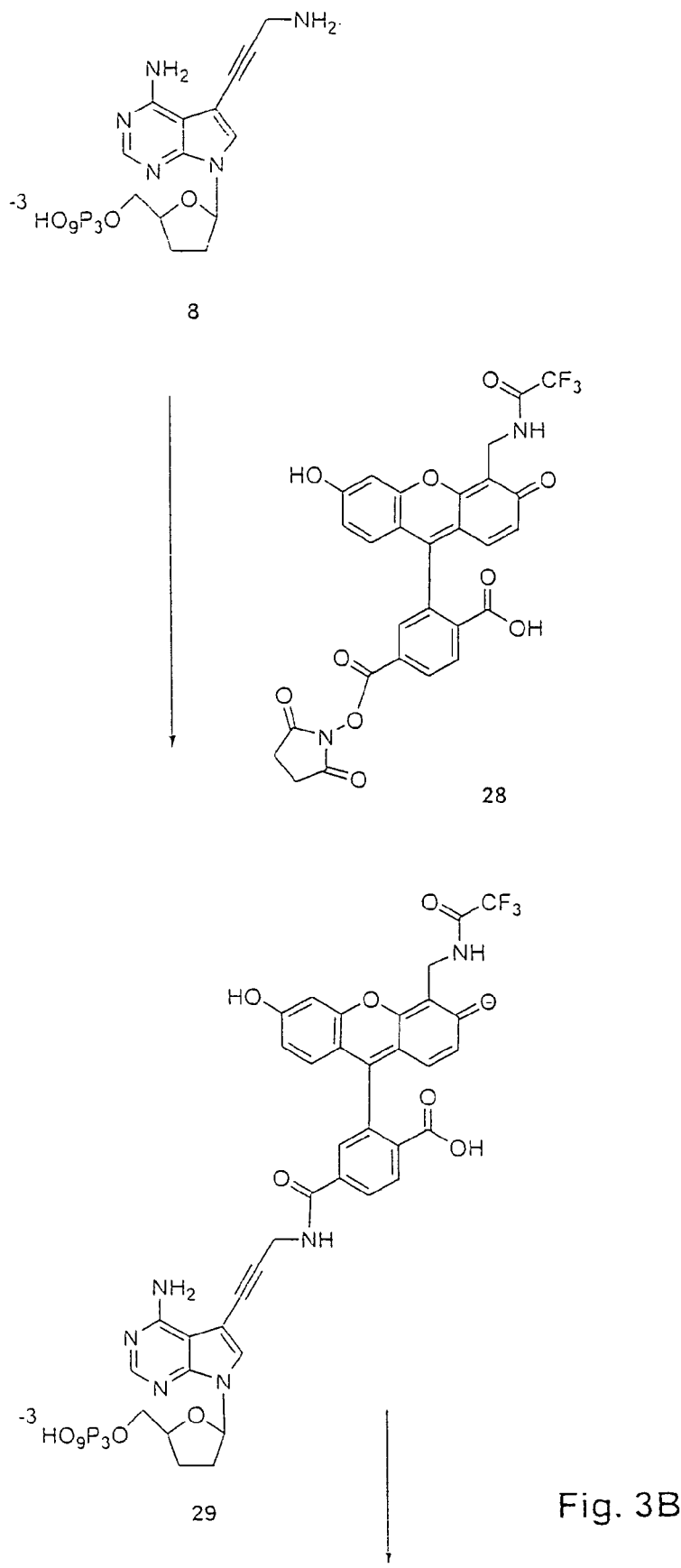
Figure 3C:
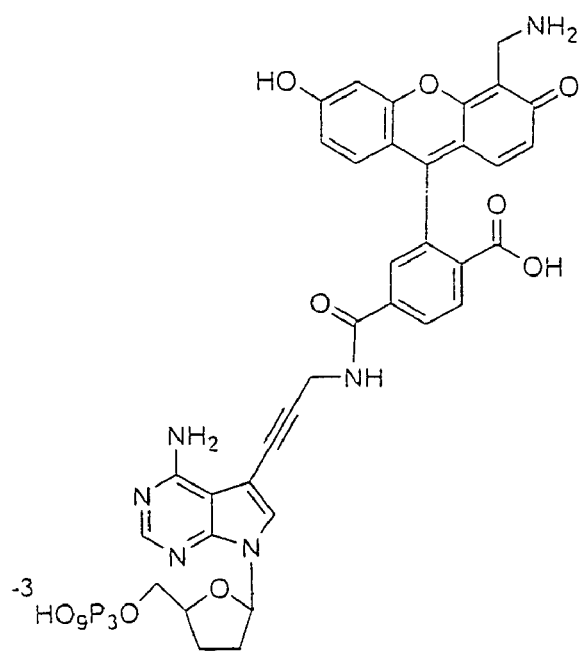
Figure 3C:
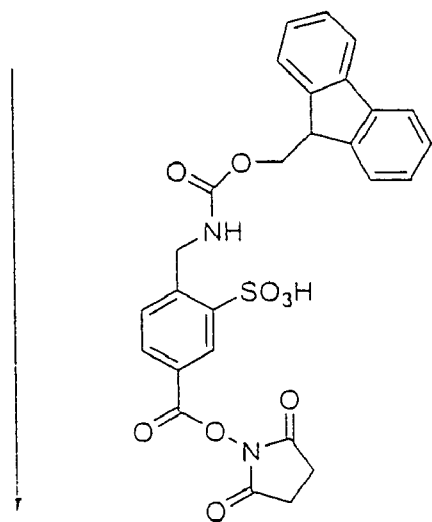
Figure 3D:
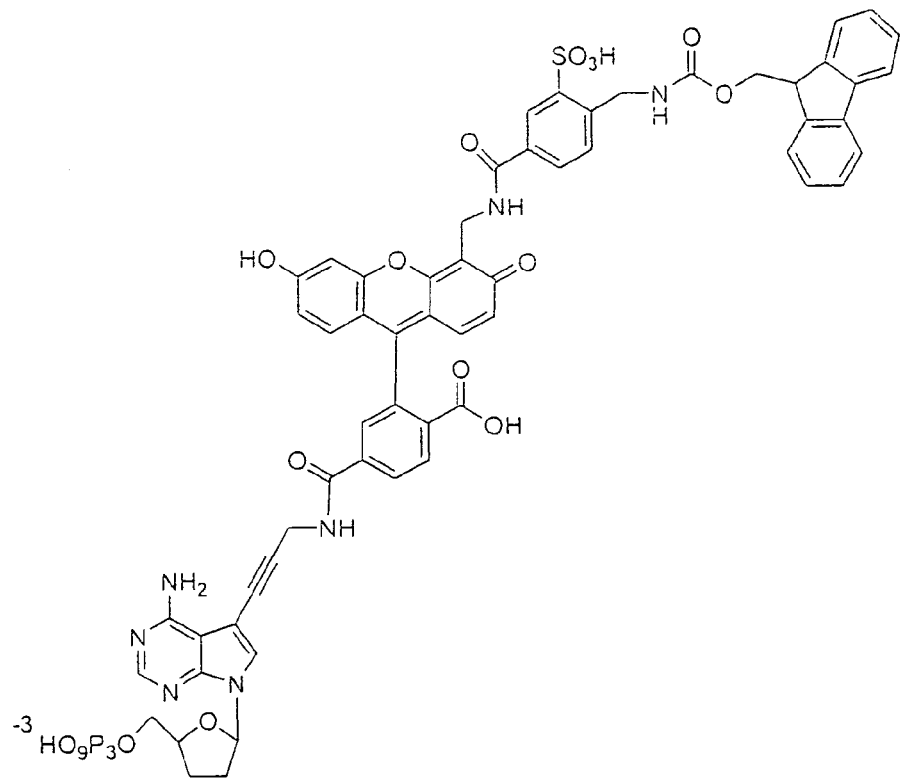
Figure 3D:
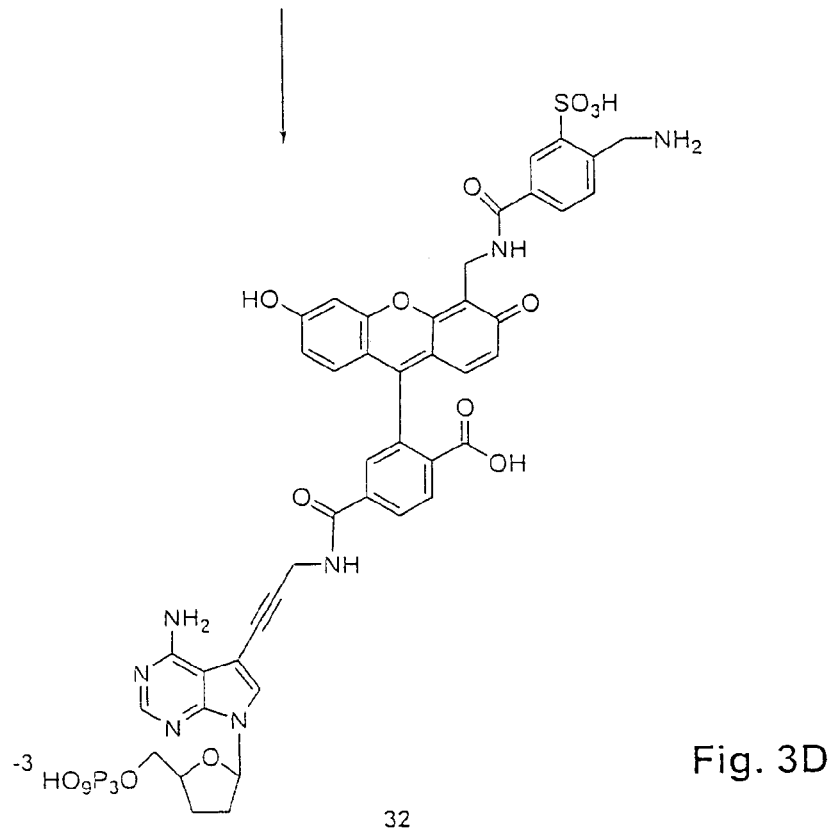
Figure 3E:
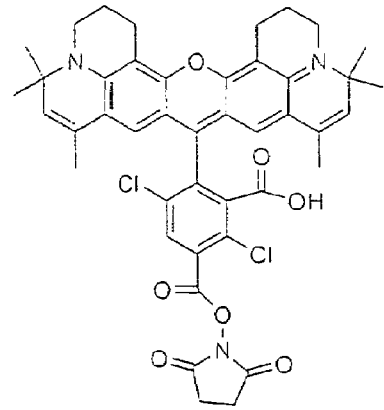
Figure 3E:
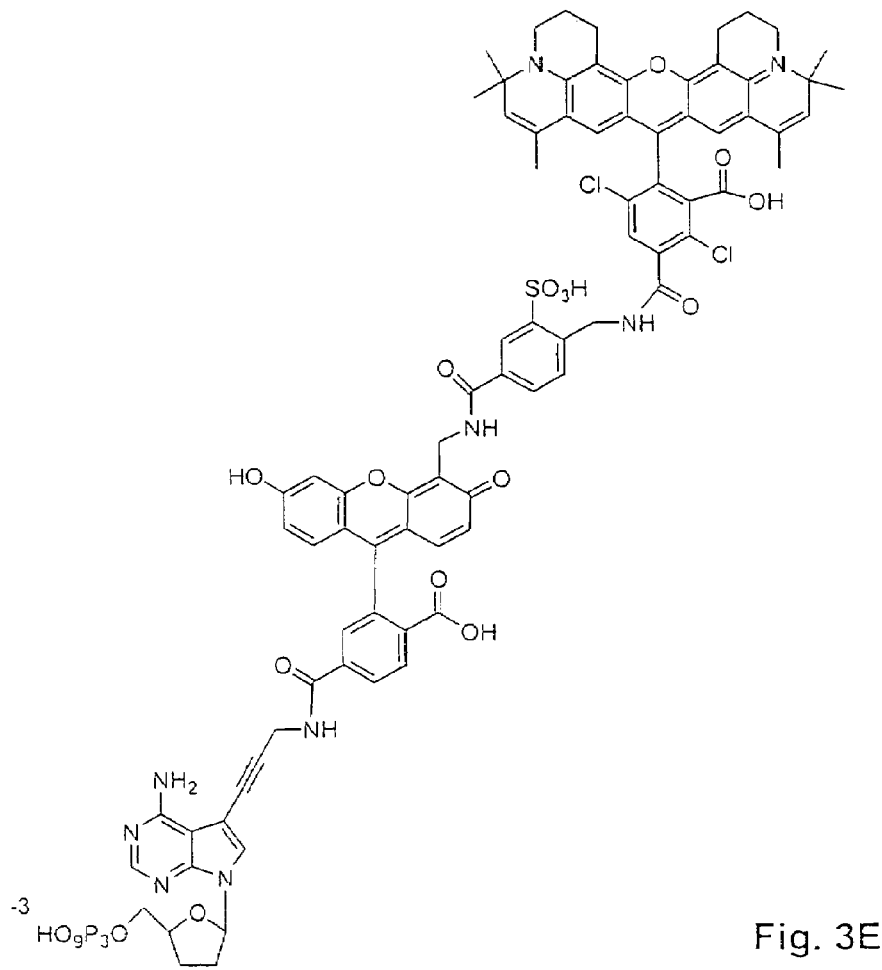
Figure 4A:
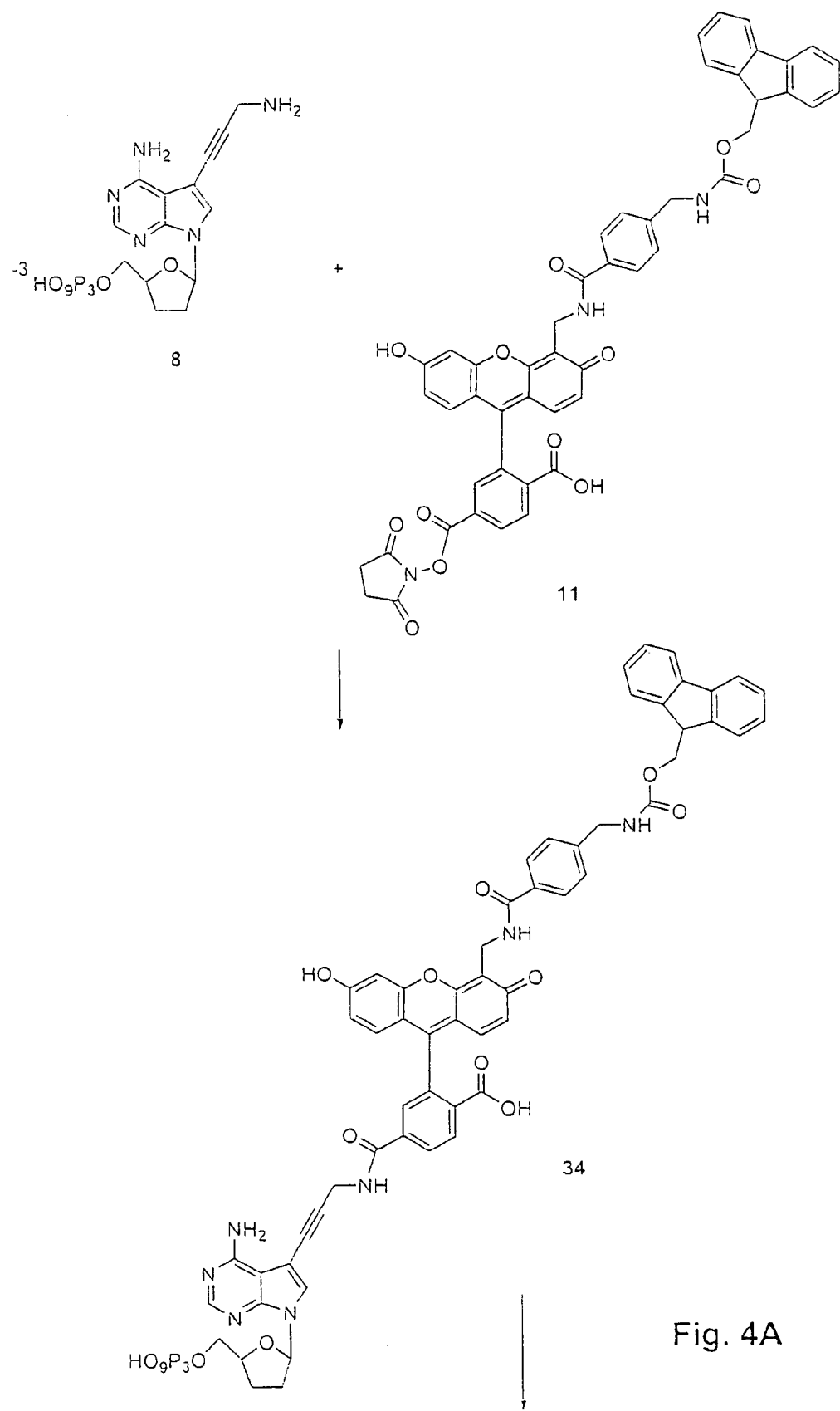
Figure 4B:
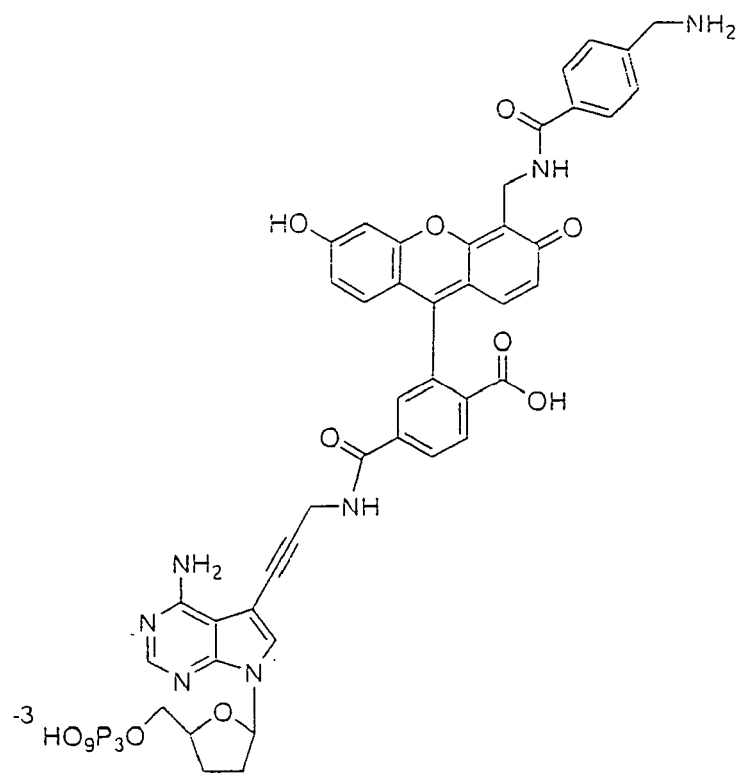
Figure 4B:
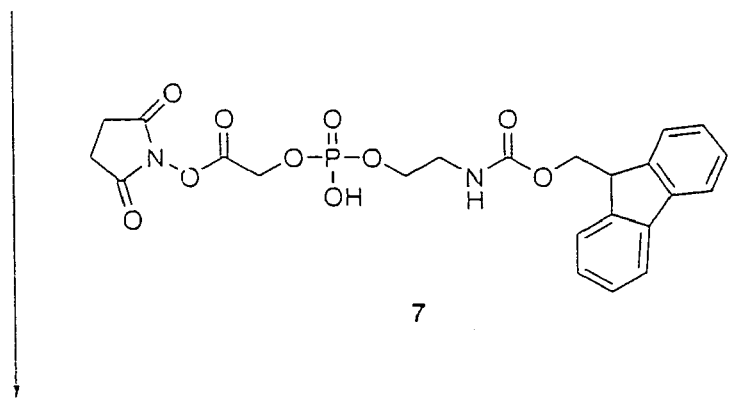
Figure 4C:
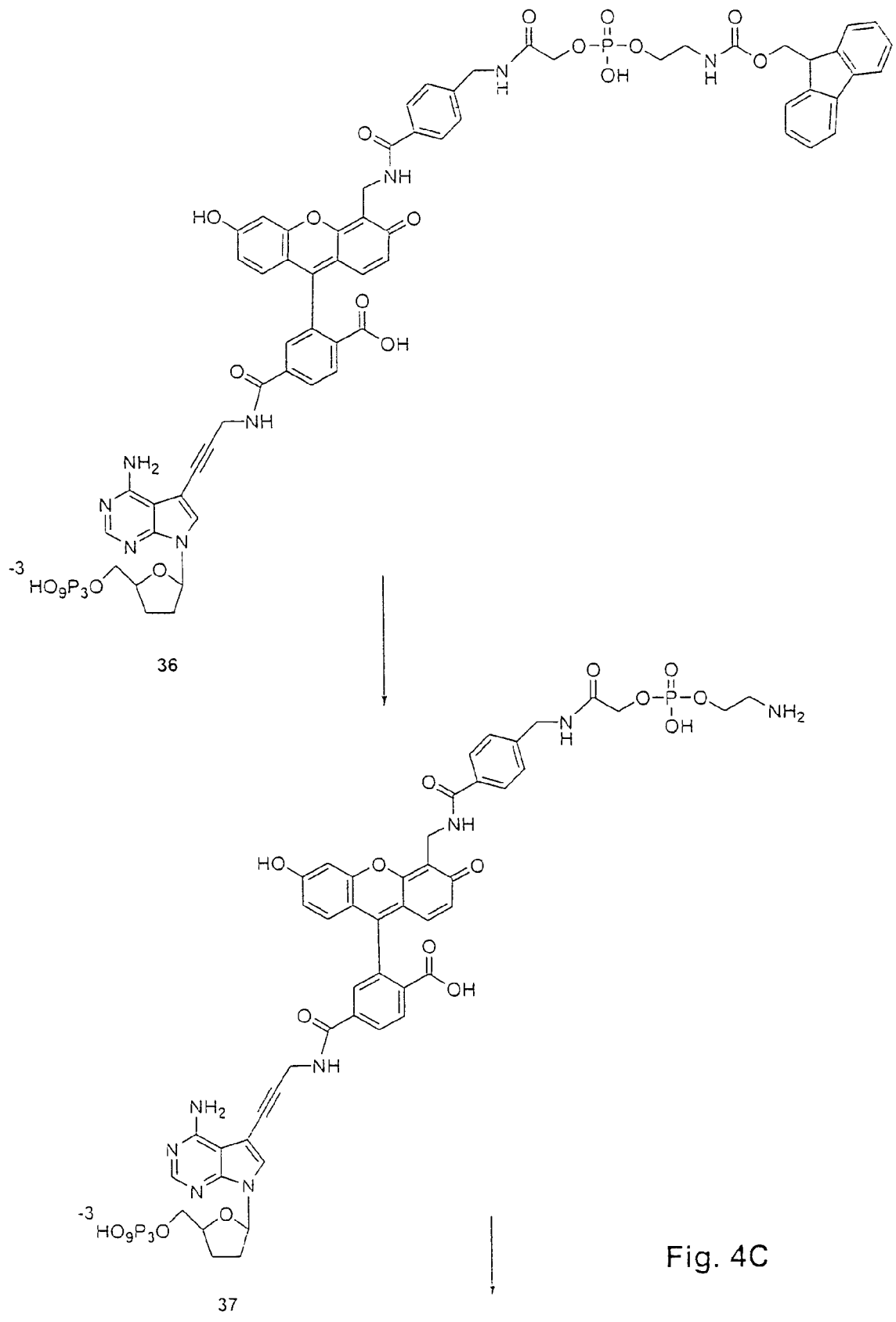
Figure 4D:
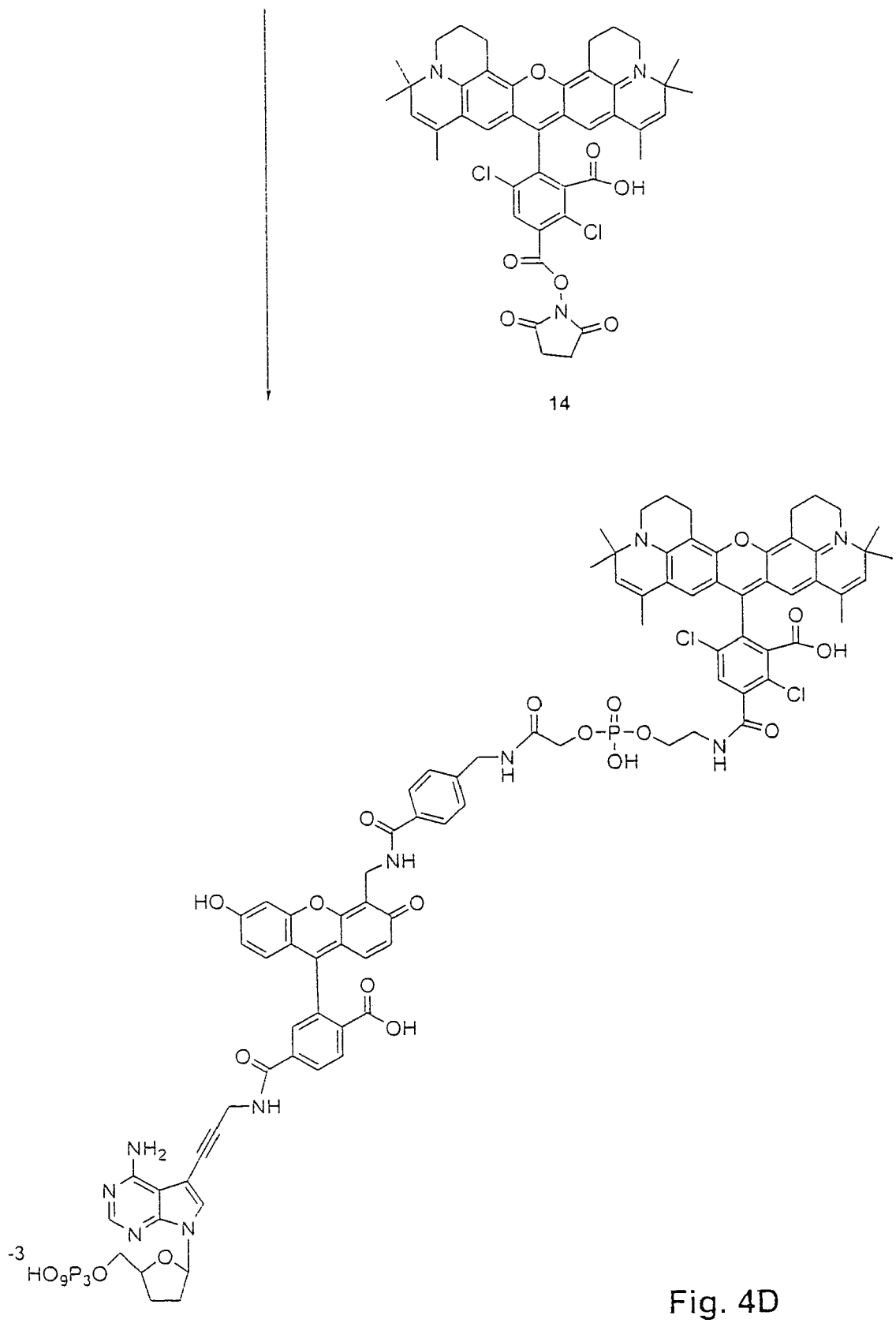
Figure 5A:
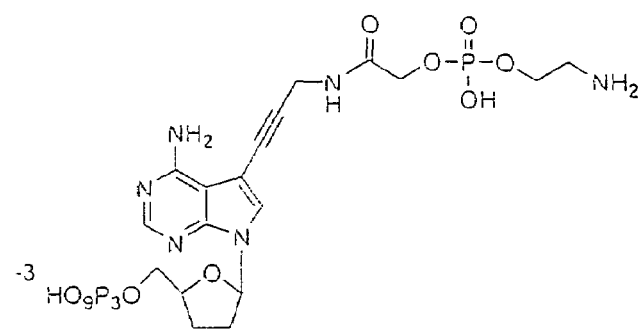
Figure 5A:
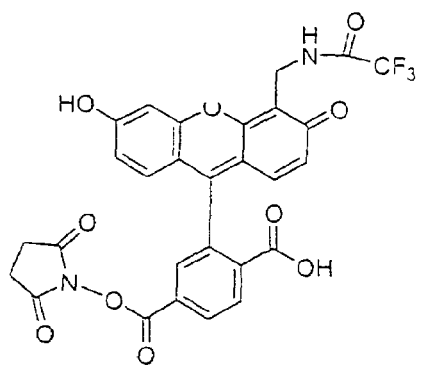
Figure 5A:
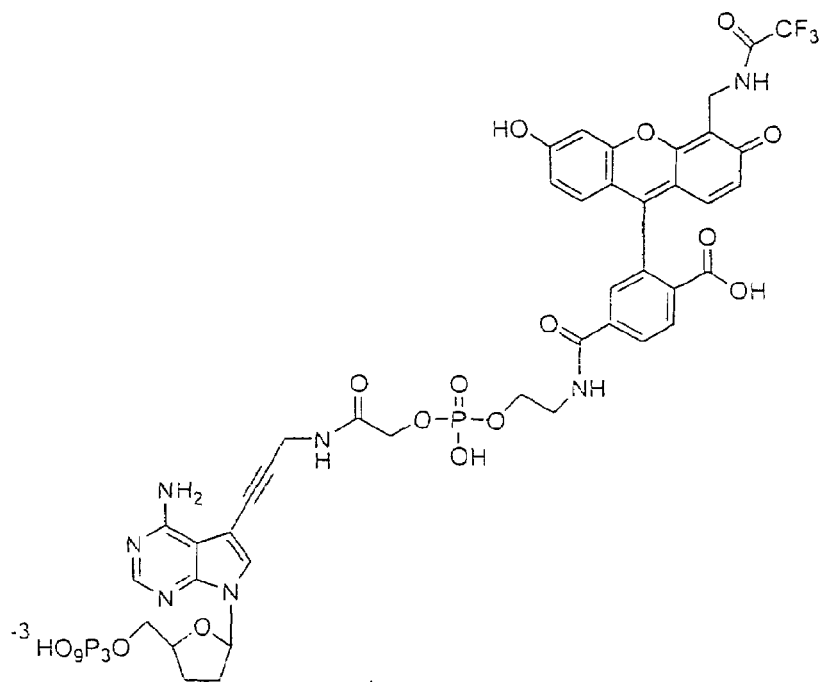
Figure 5B:
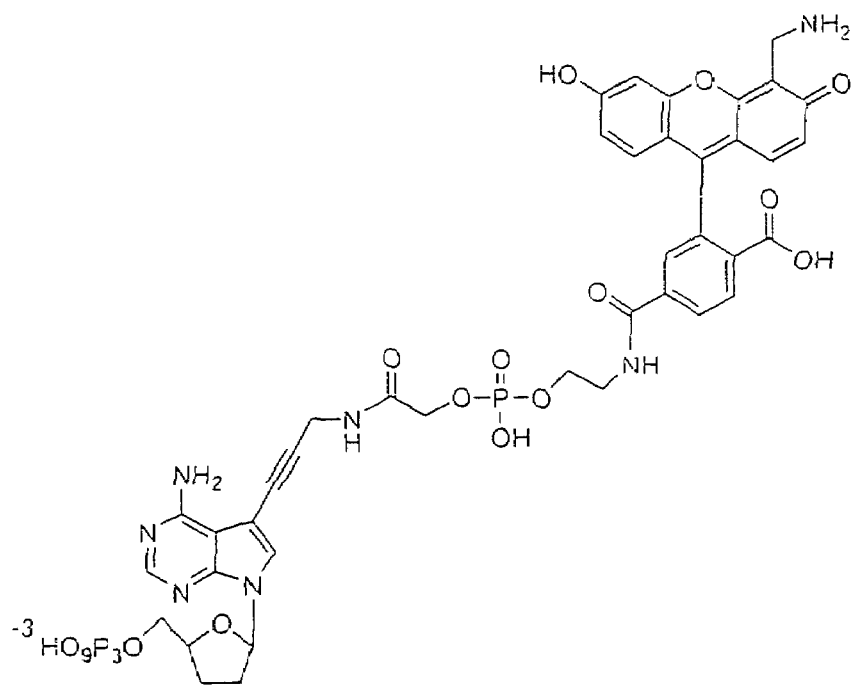
Figure 5B:
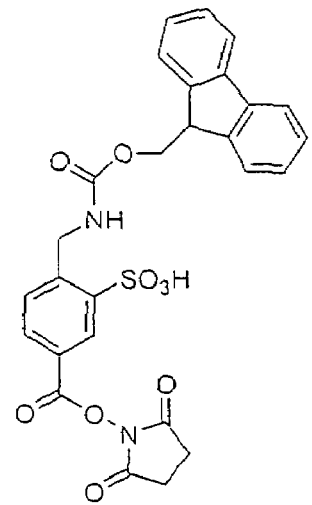
Figure 5C:
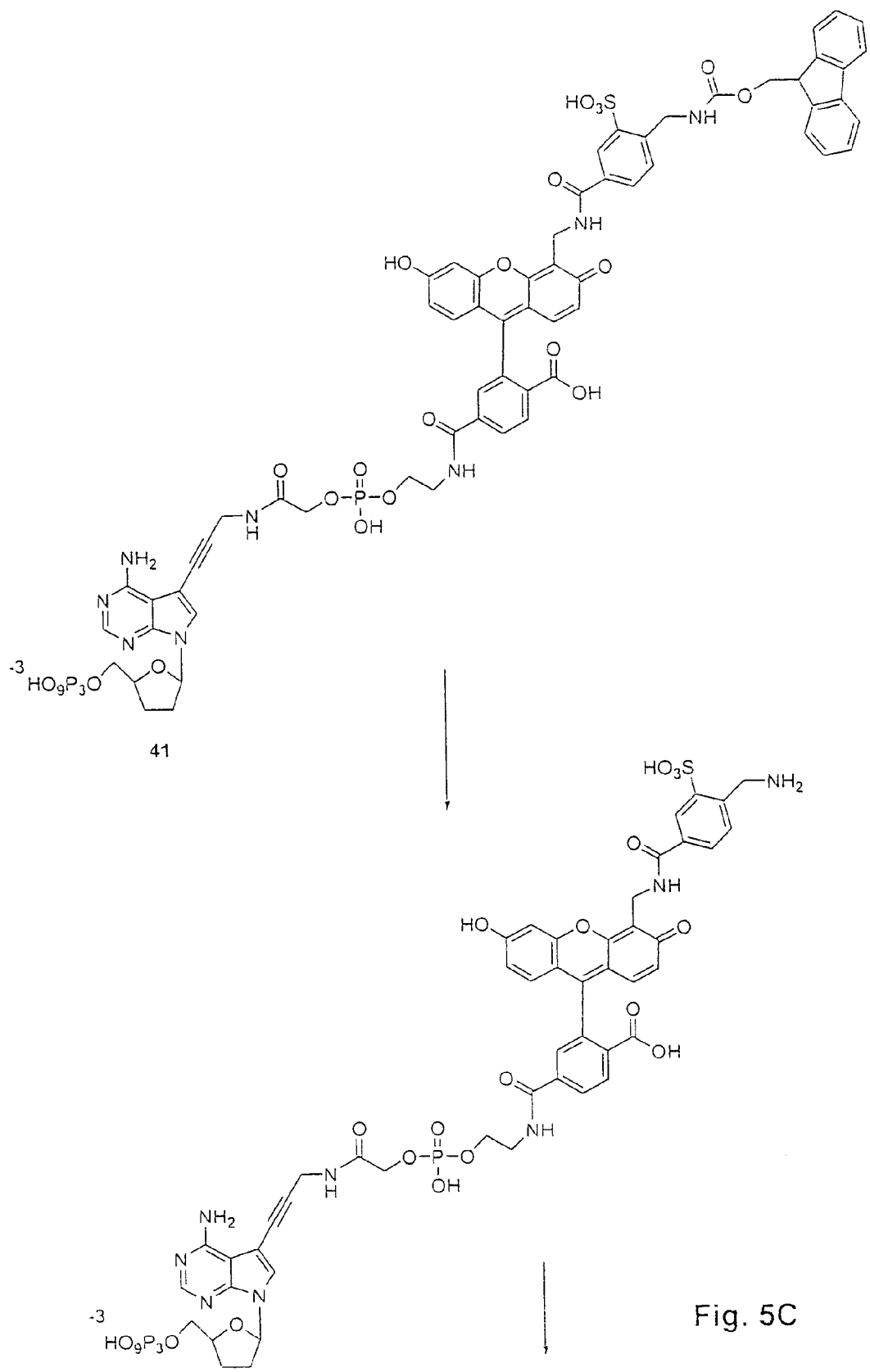
Figure 5D:
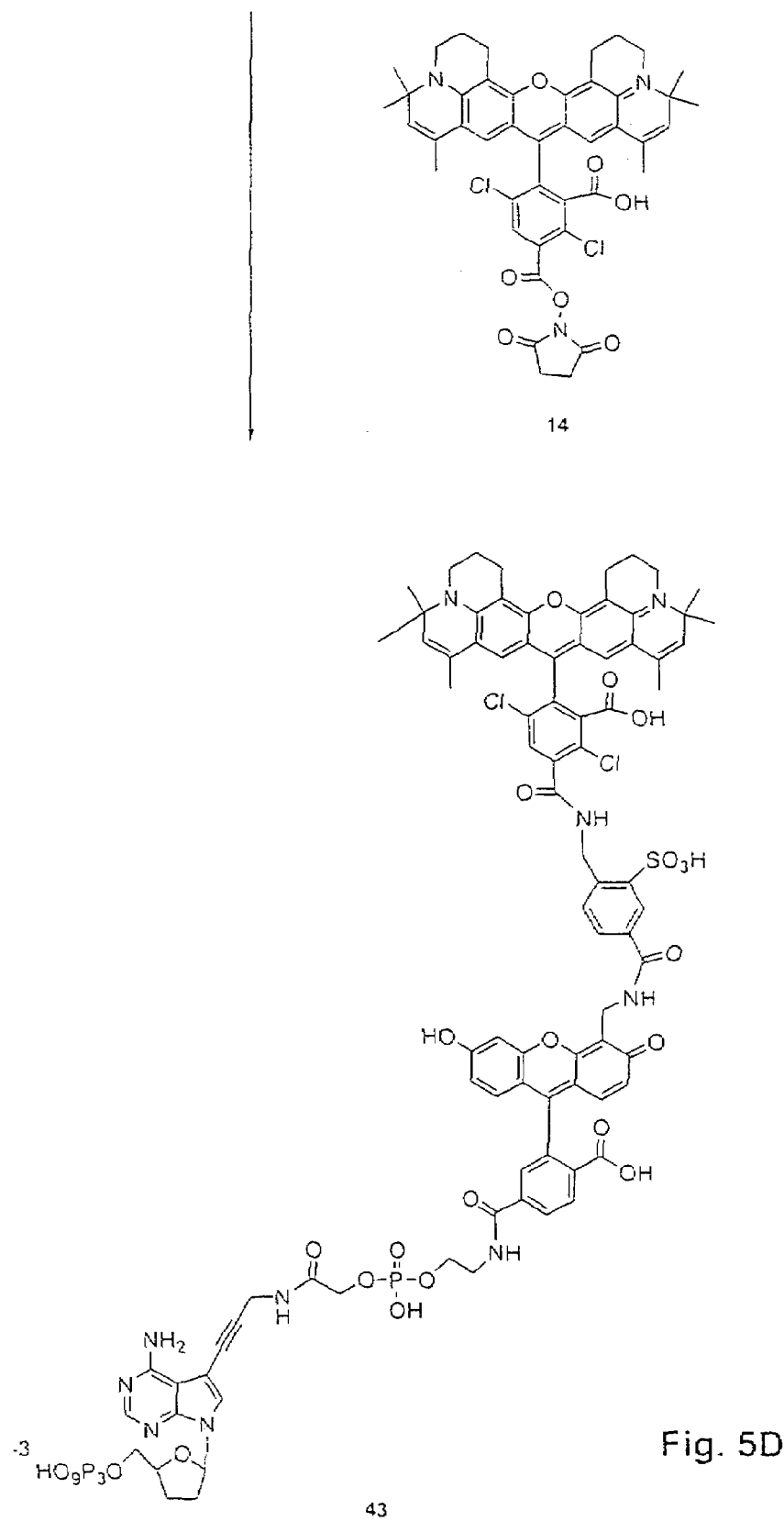
Figure 6:
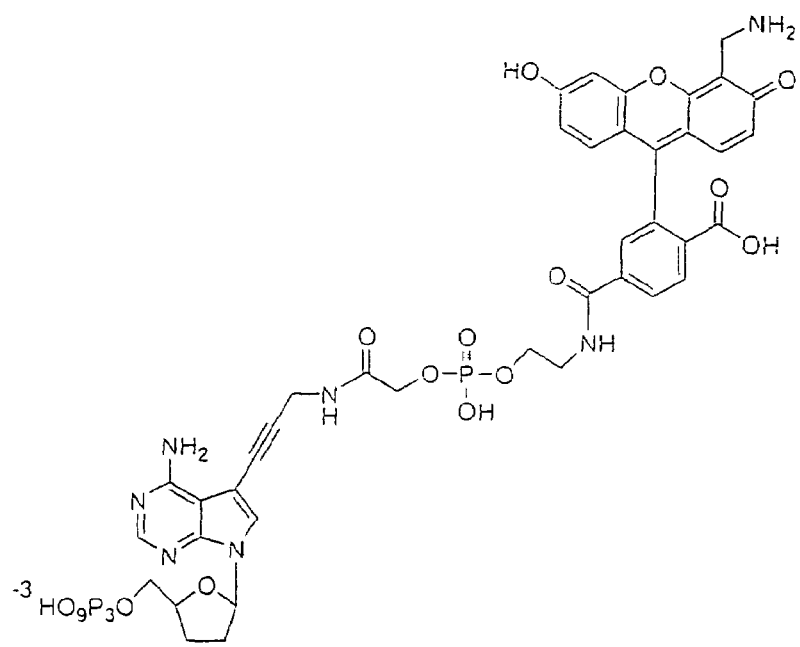
Figure 6:
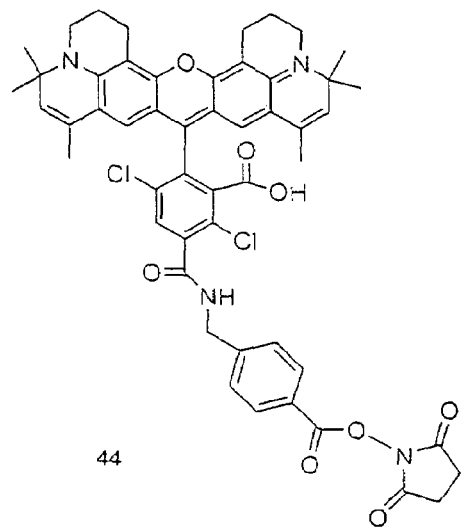
Figure 7A:
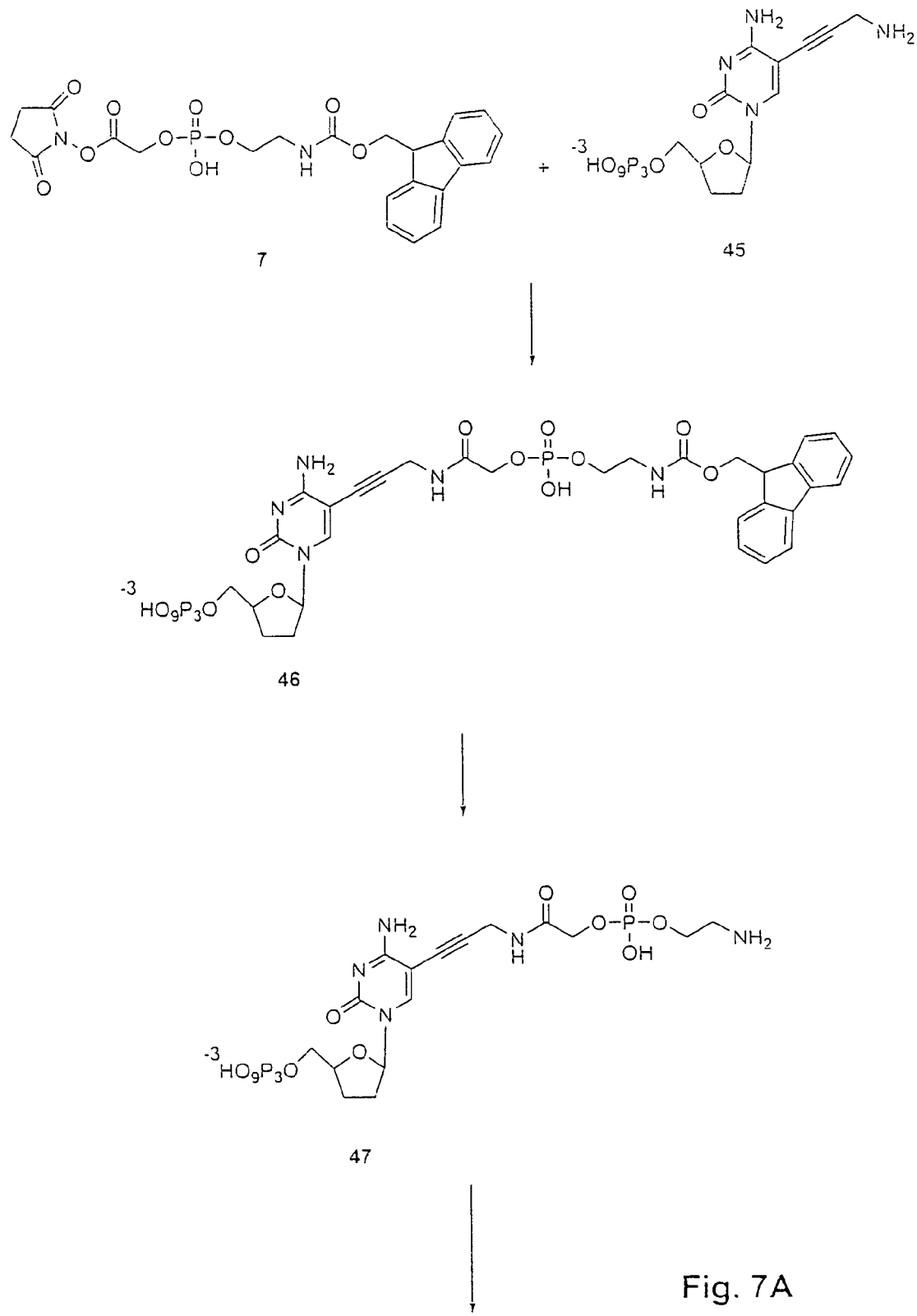
Figure 7B:
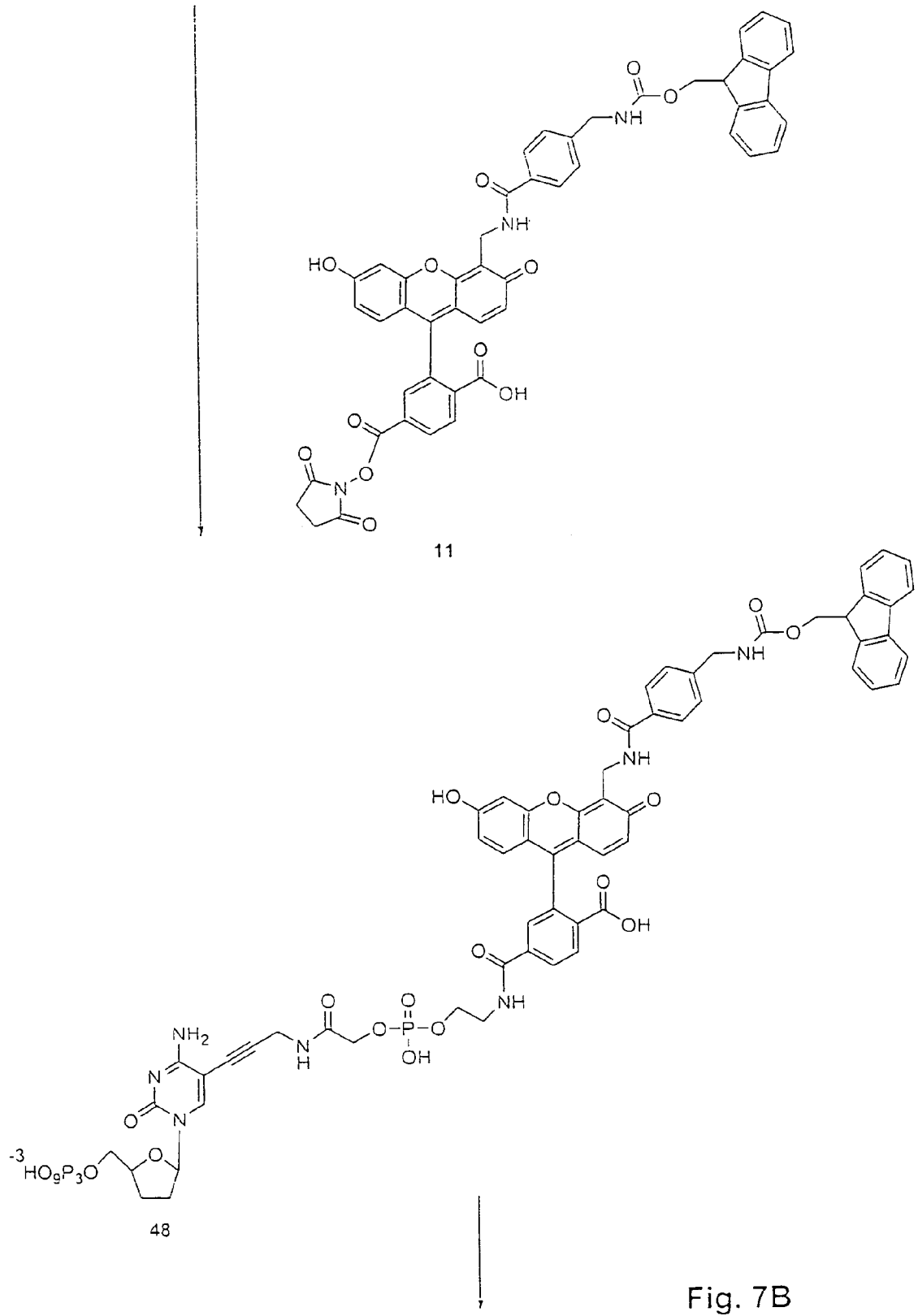
Figure 7C:
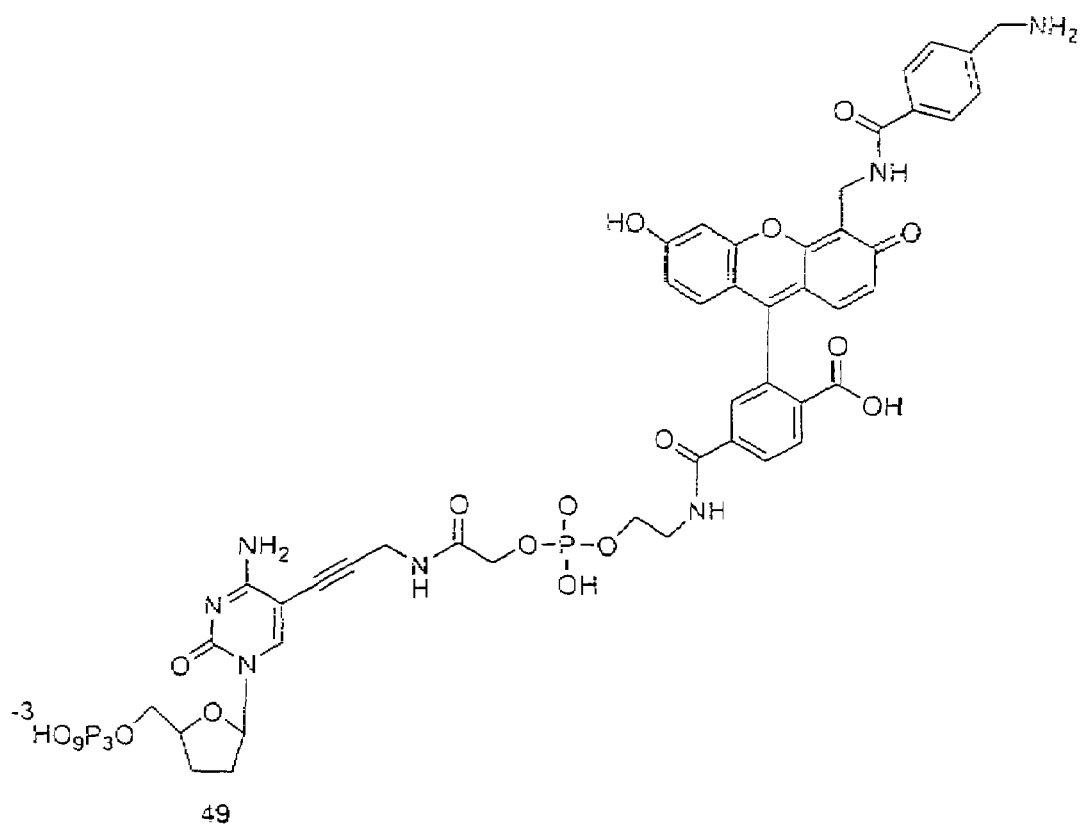
Figure 7C:
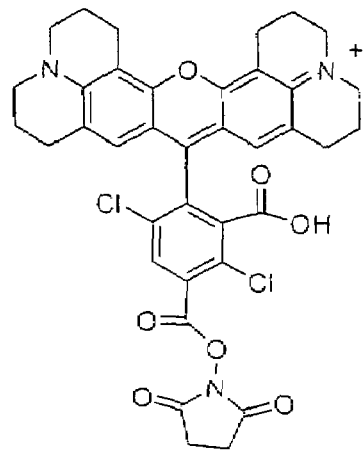
Figure 7D:
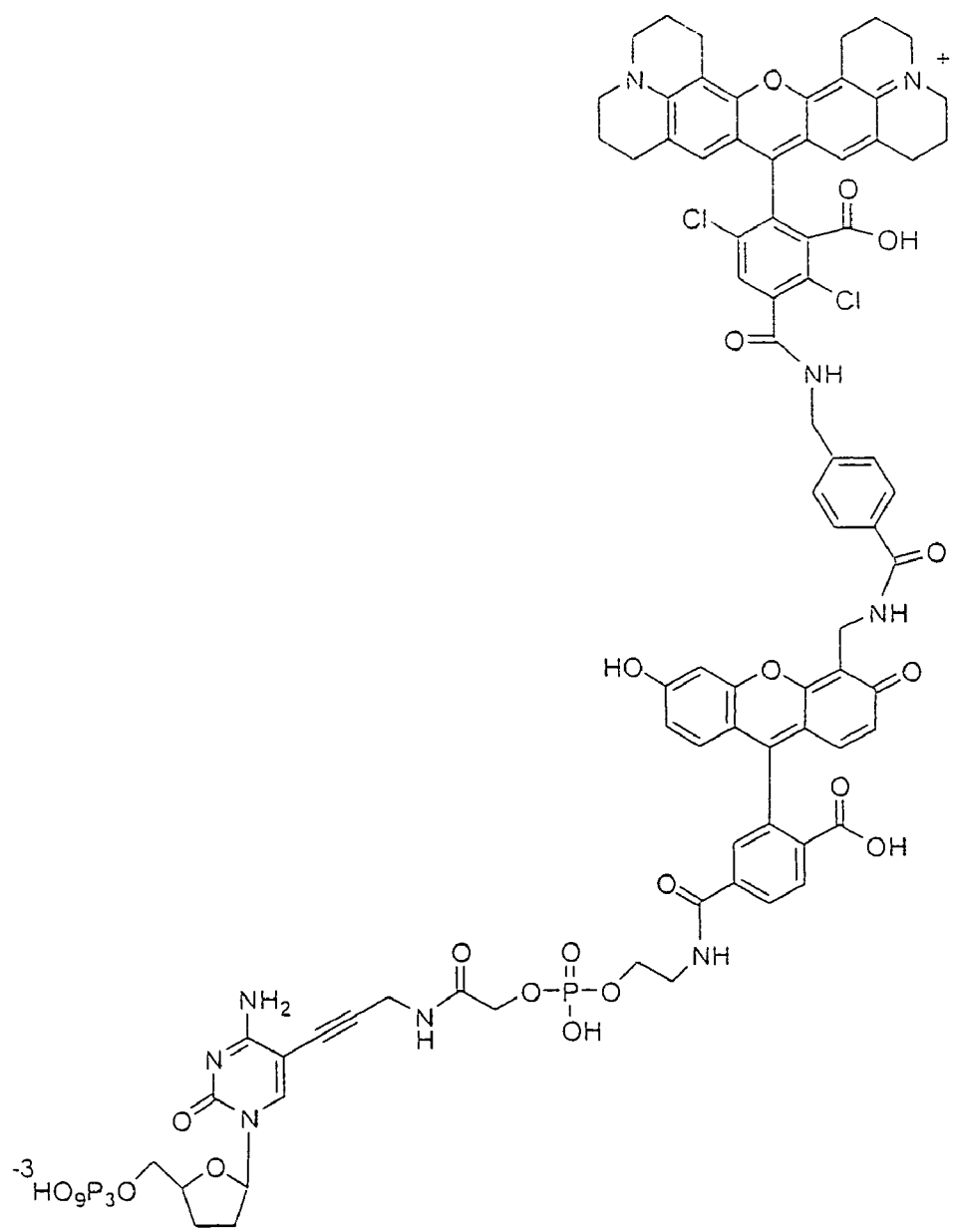
Figure 8A:
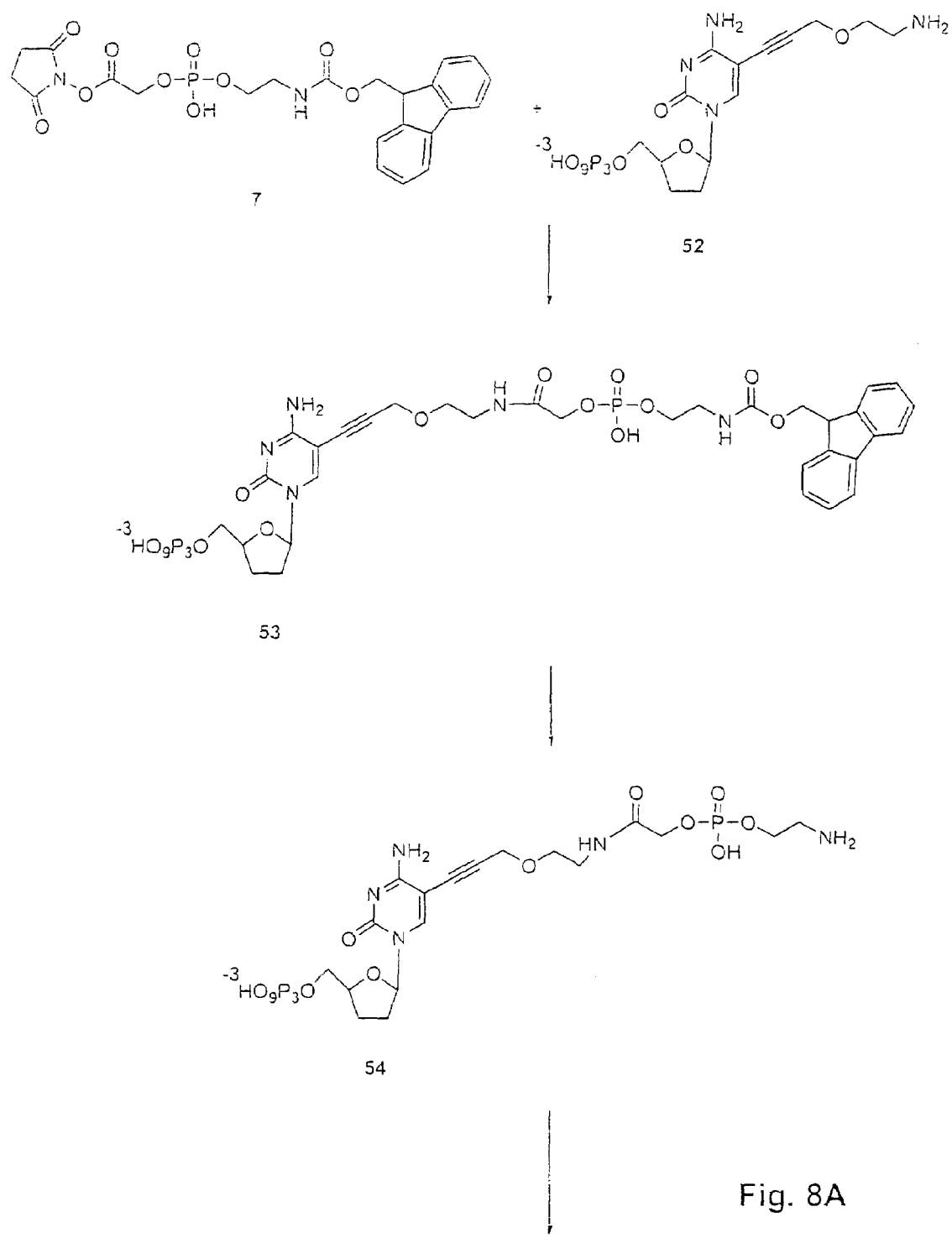
Figure 8B:
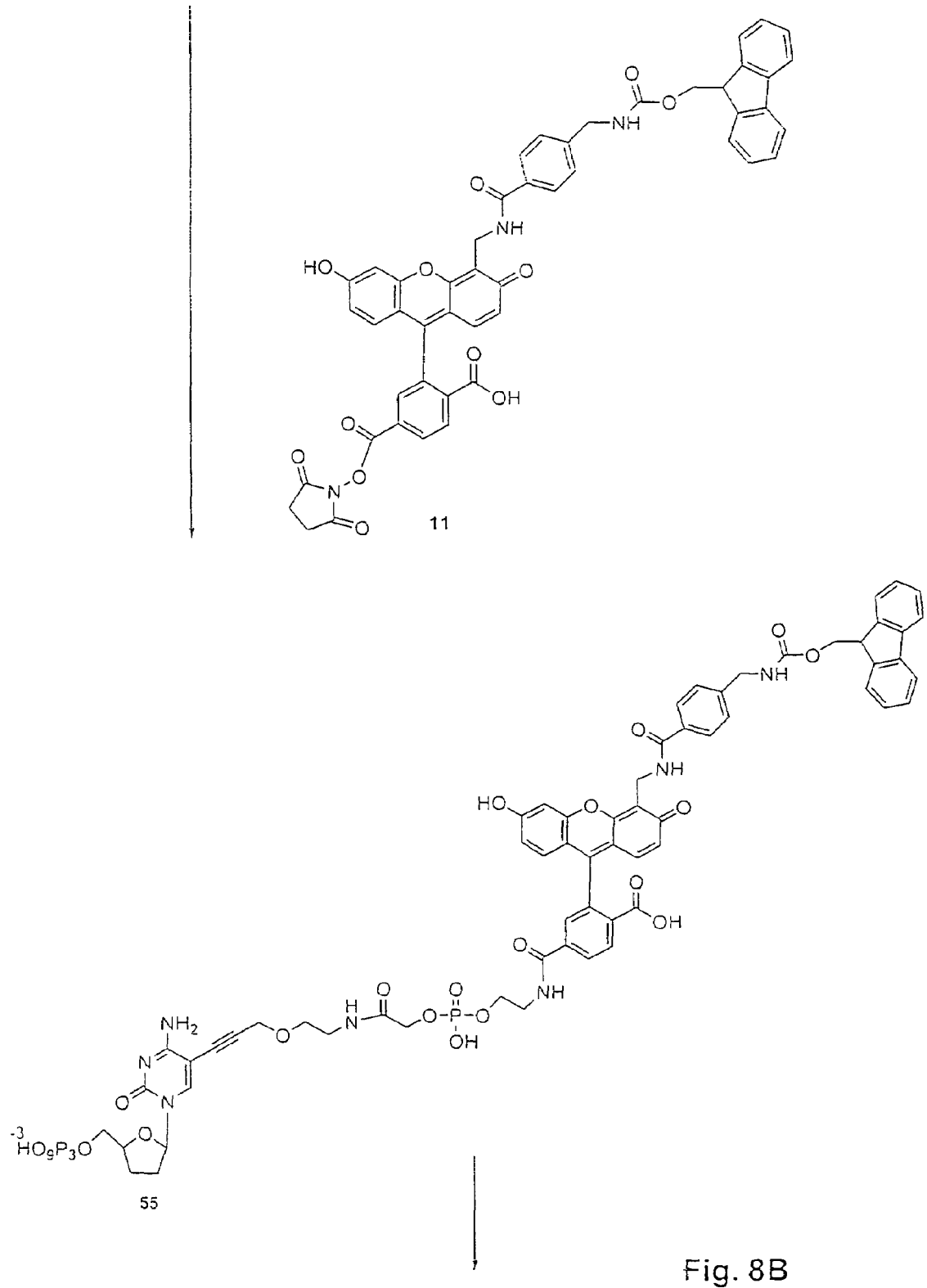
Figure 8C:
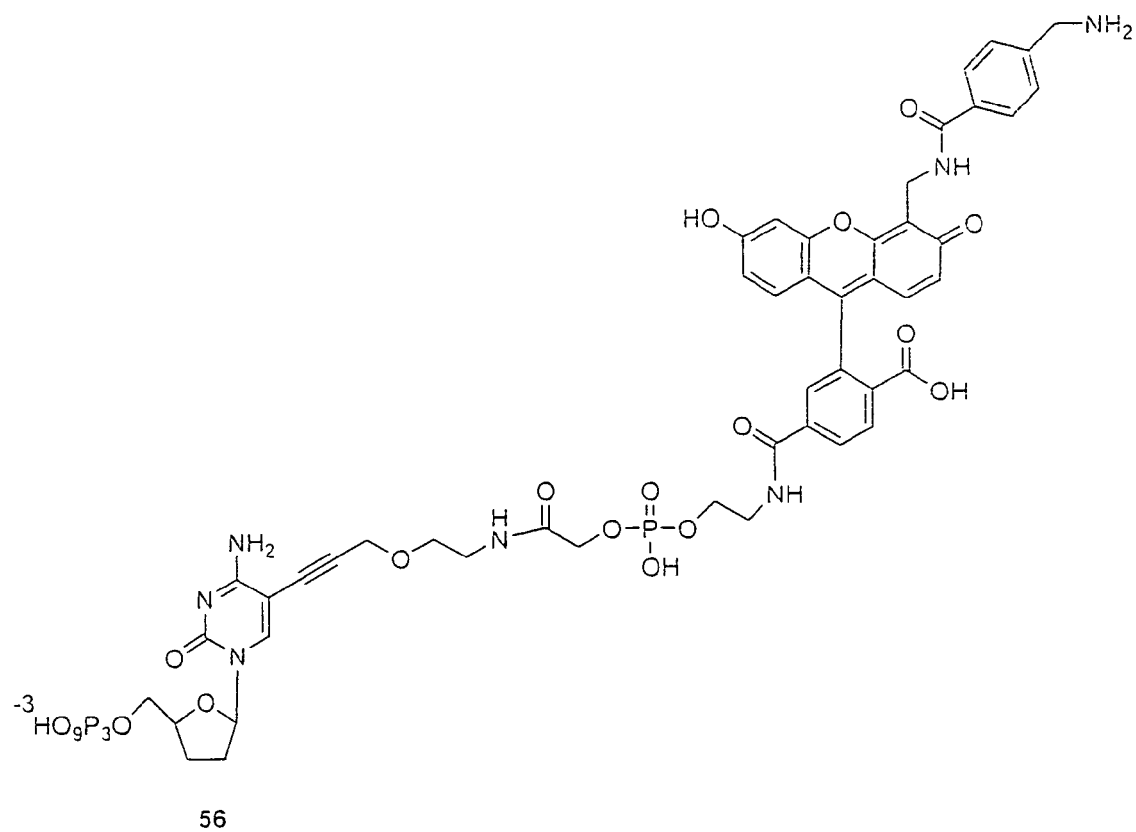
Figure 8C:
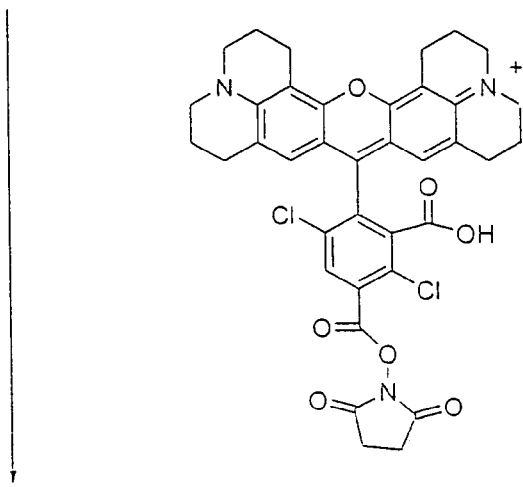
Figure 8D:
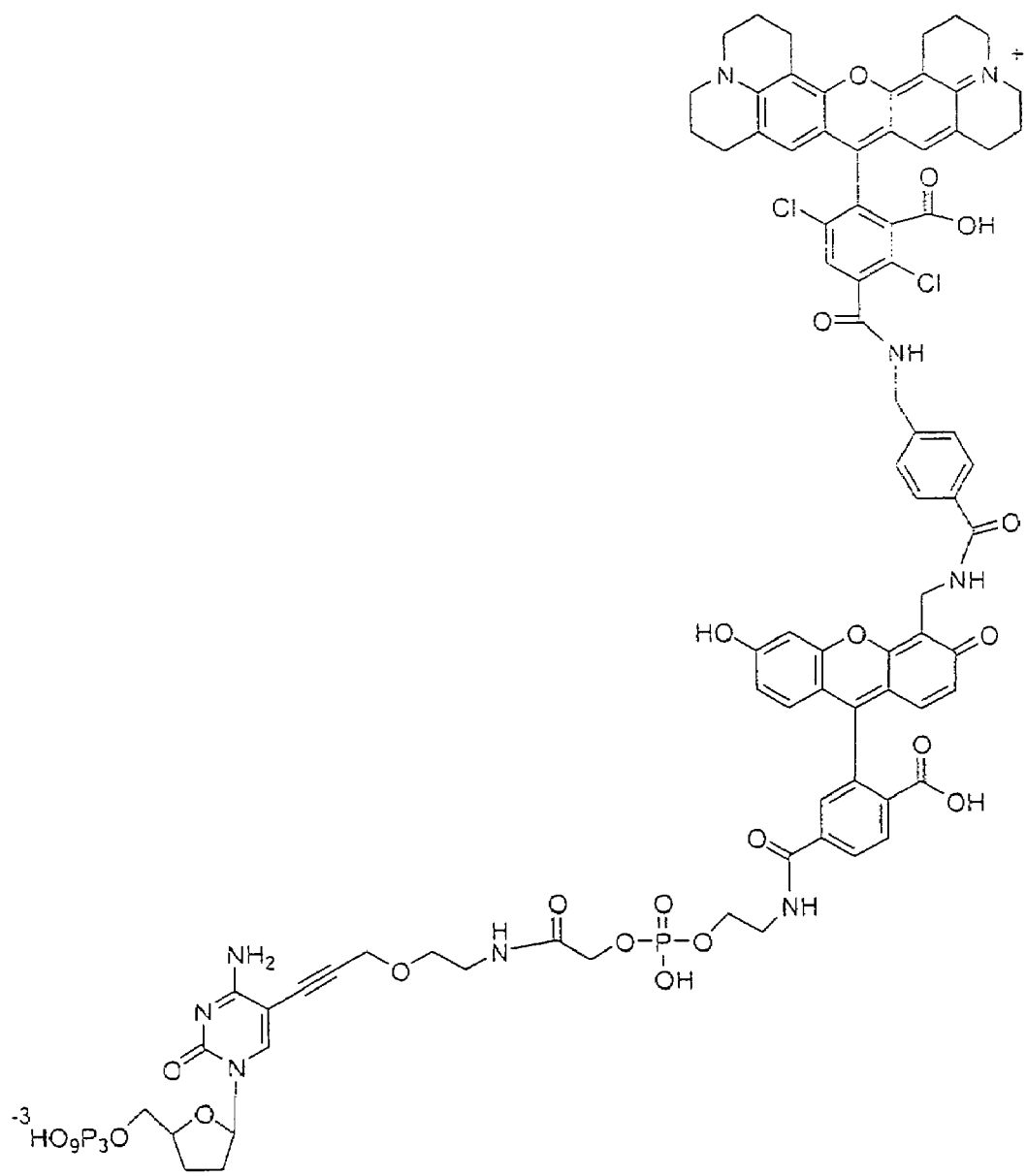
Figure 9A:
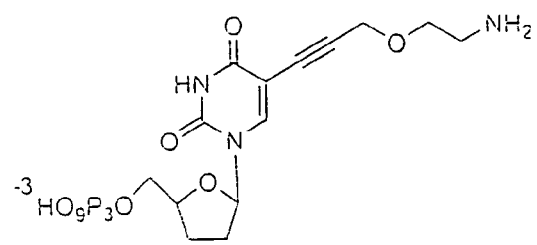
Figure 9A:
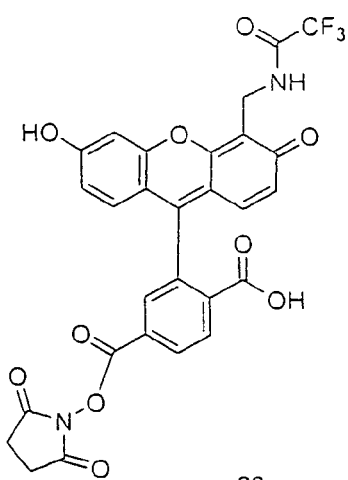
Figure 9A:
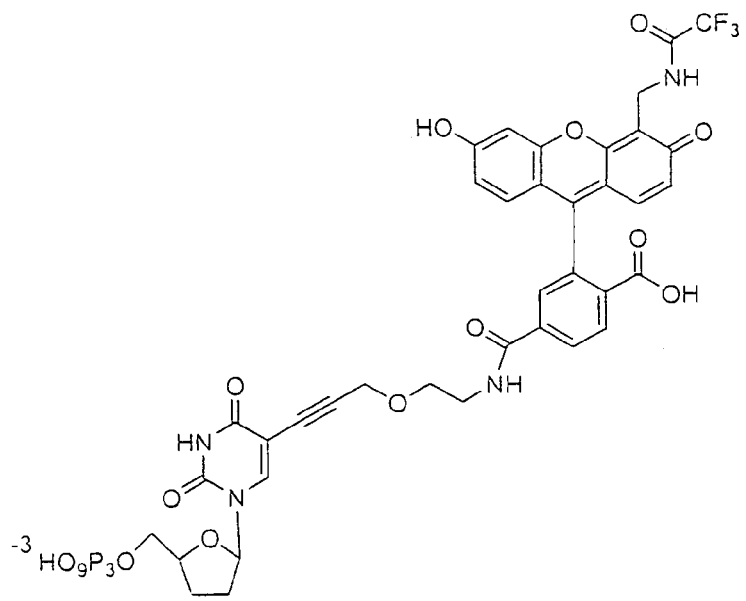
Figure 9B:
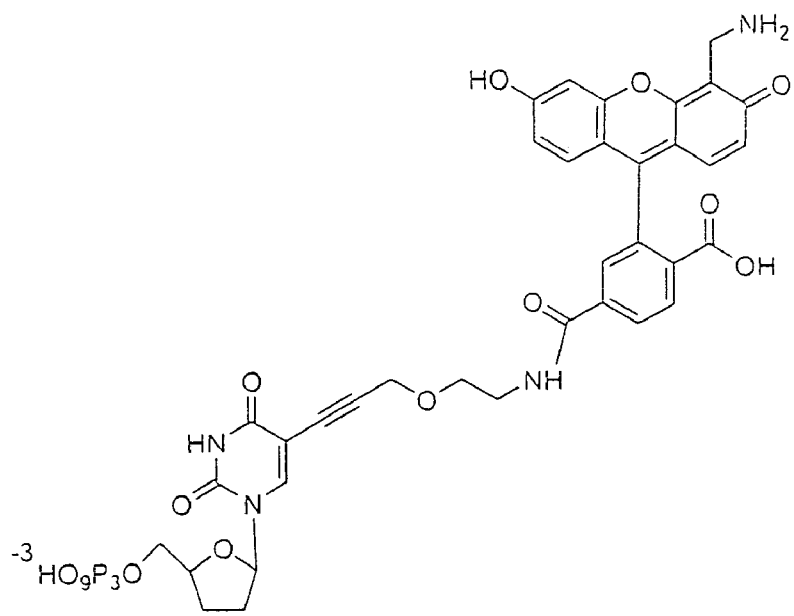
Figure 9B:
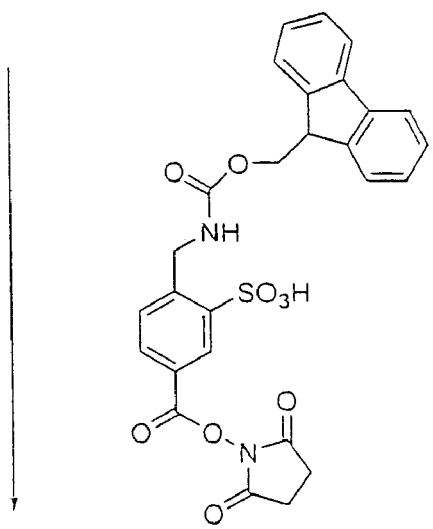
Figure 9C:
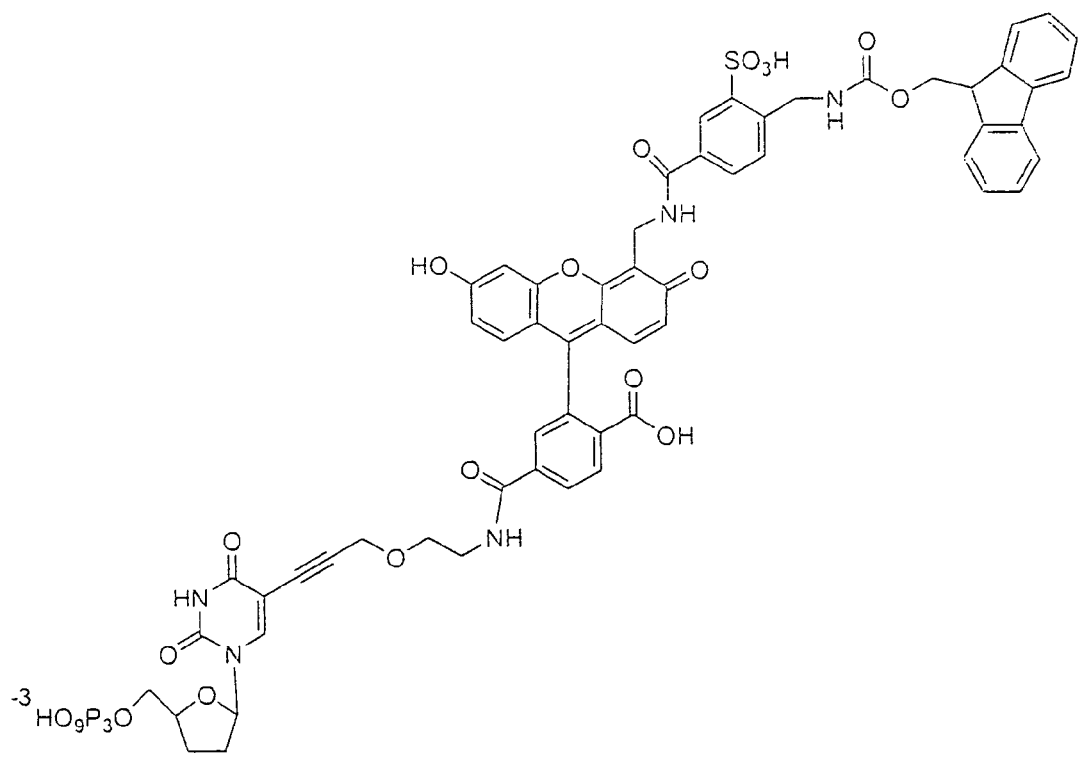
Figure 9C:
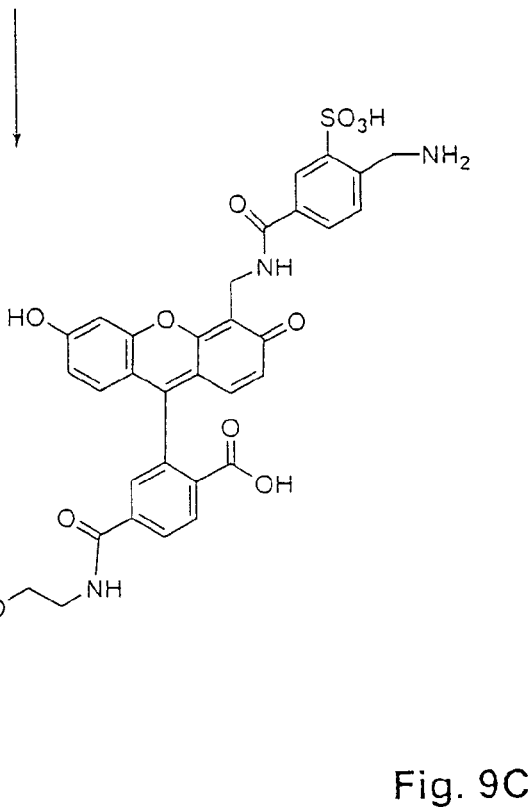
Figure 9D:
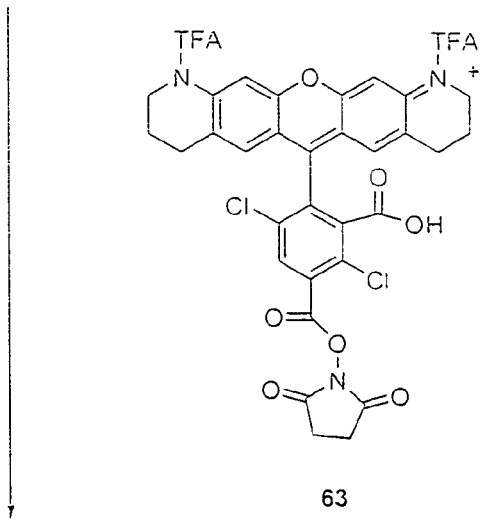
Figure 9D:
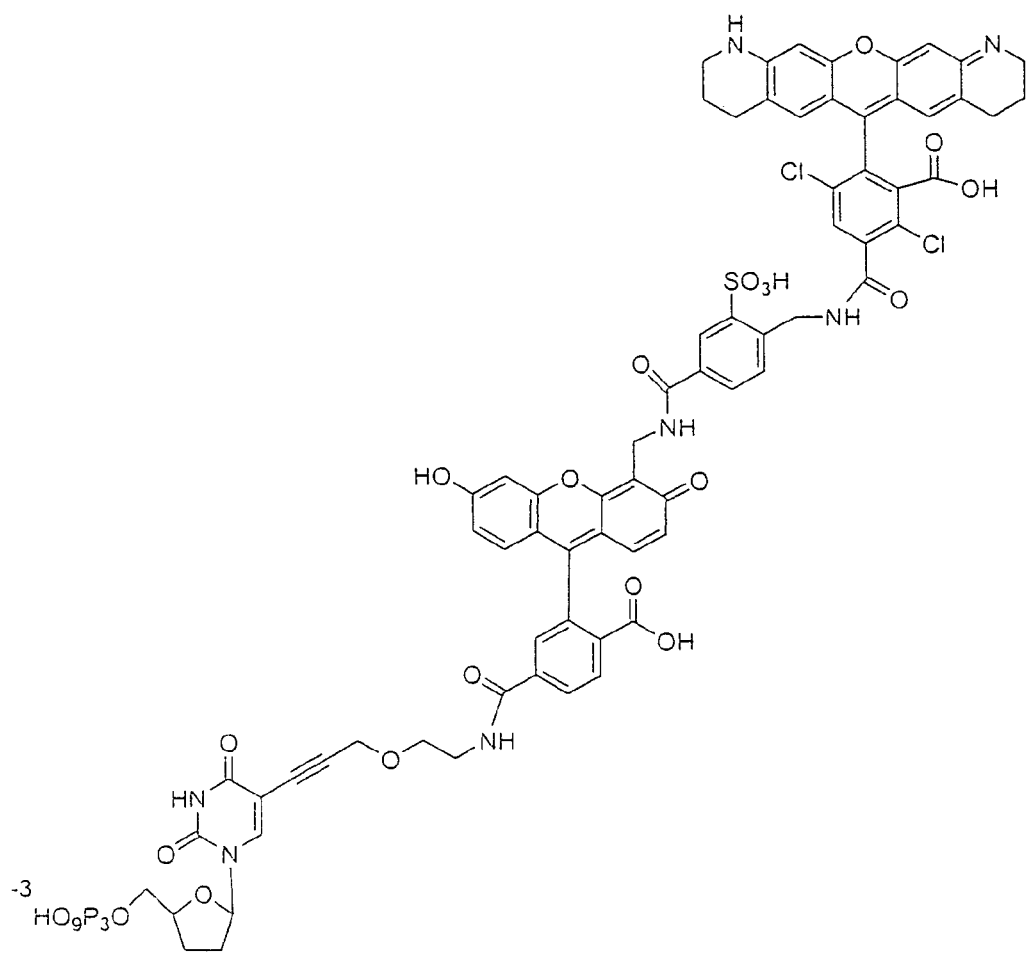
Figure 10A:
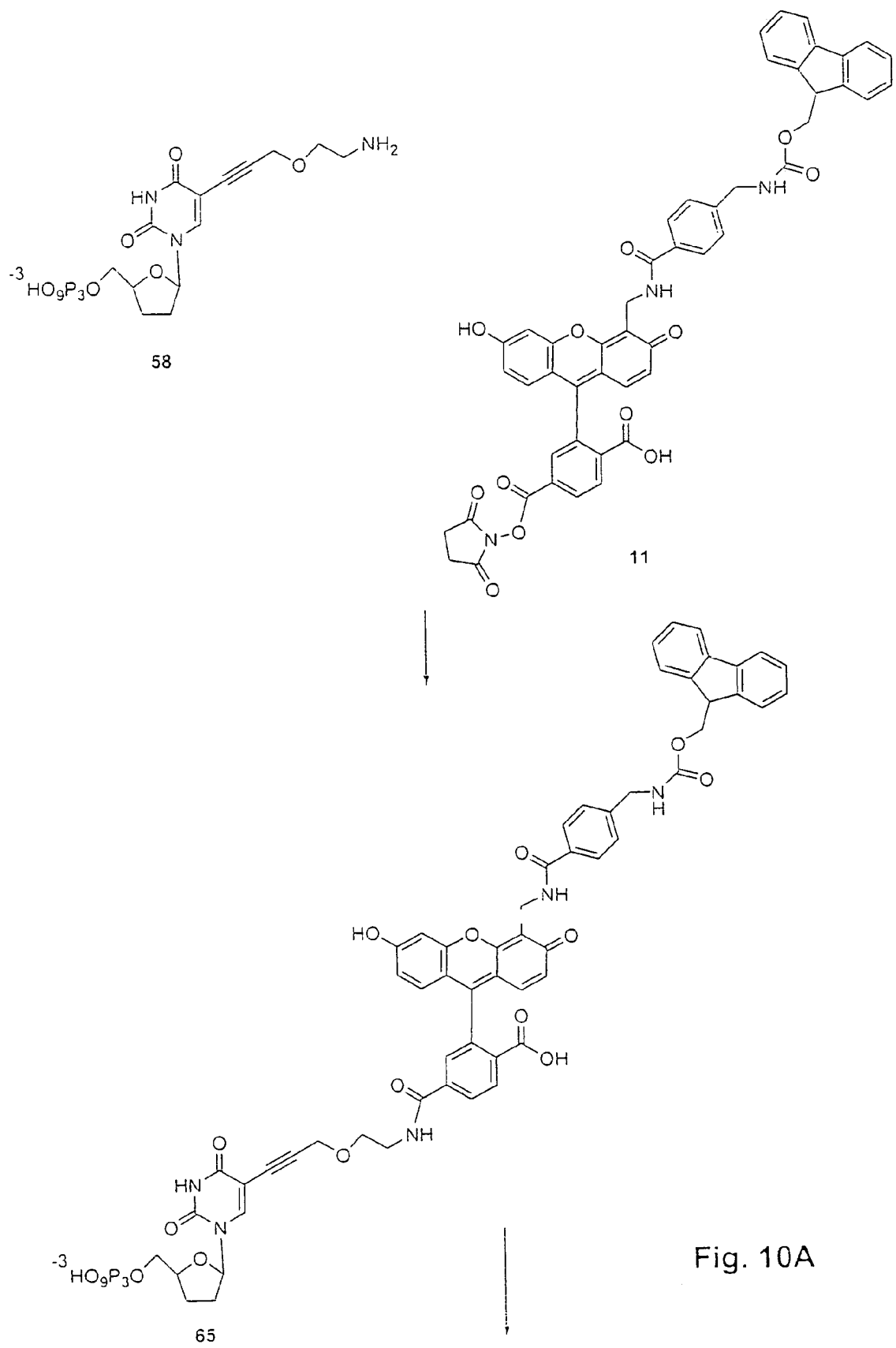
Figure 10B:
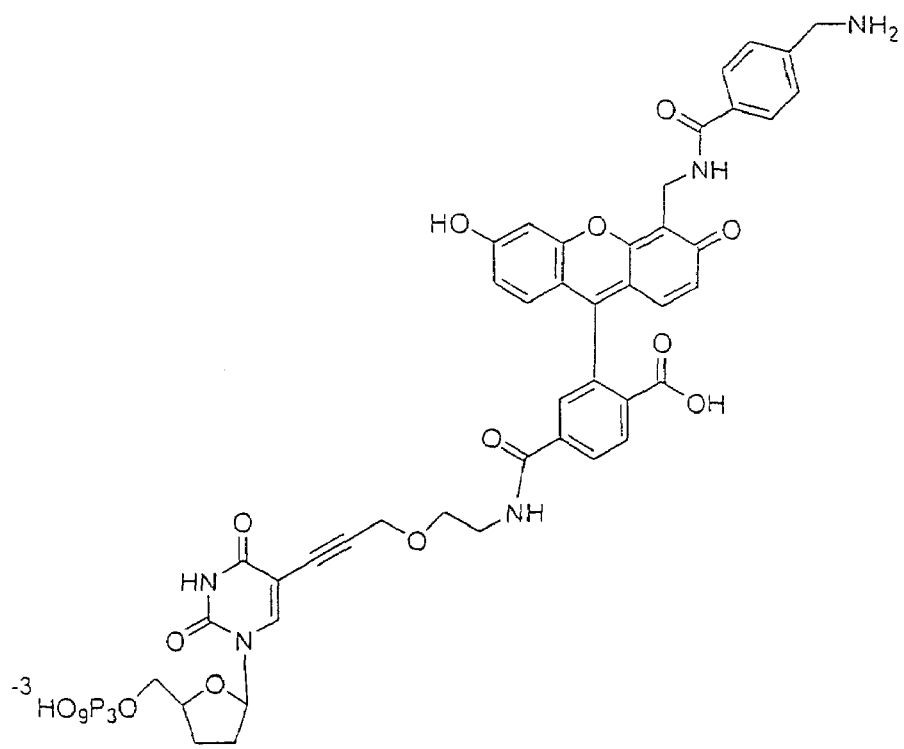
Figure 10B:
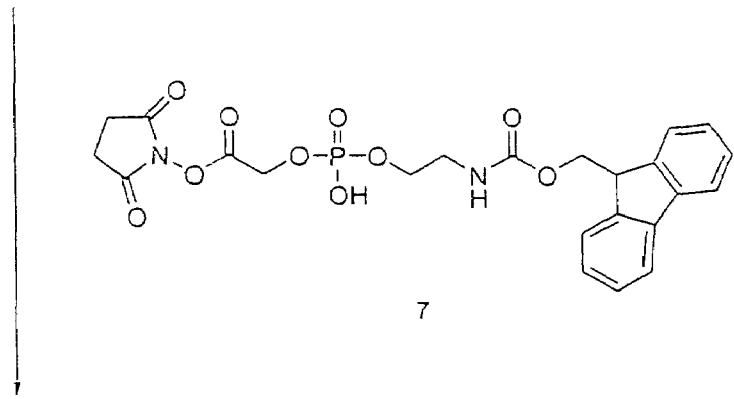
Figure 10C:
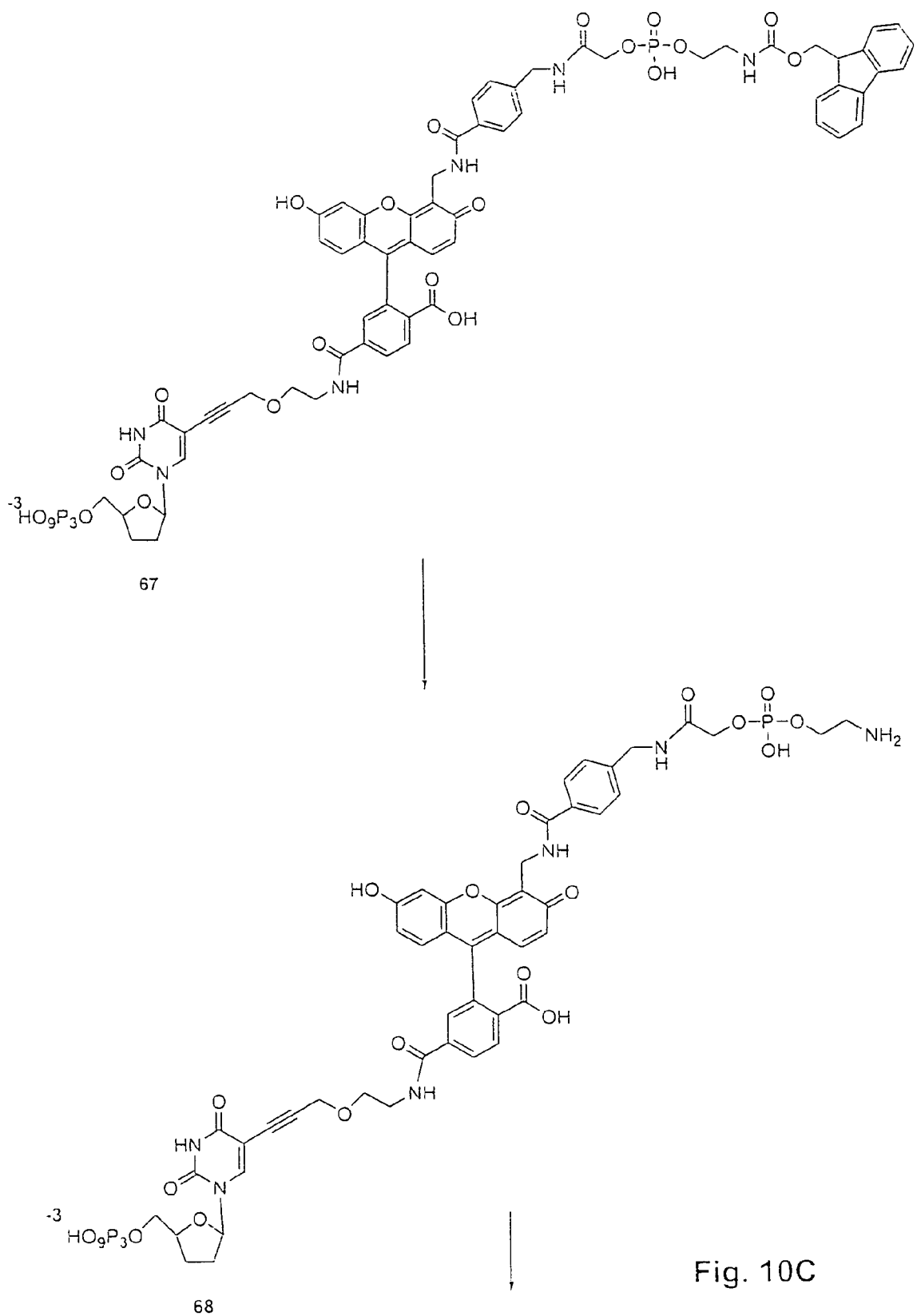
Figure 10D:
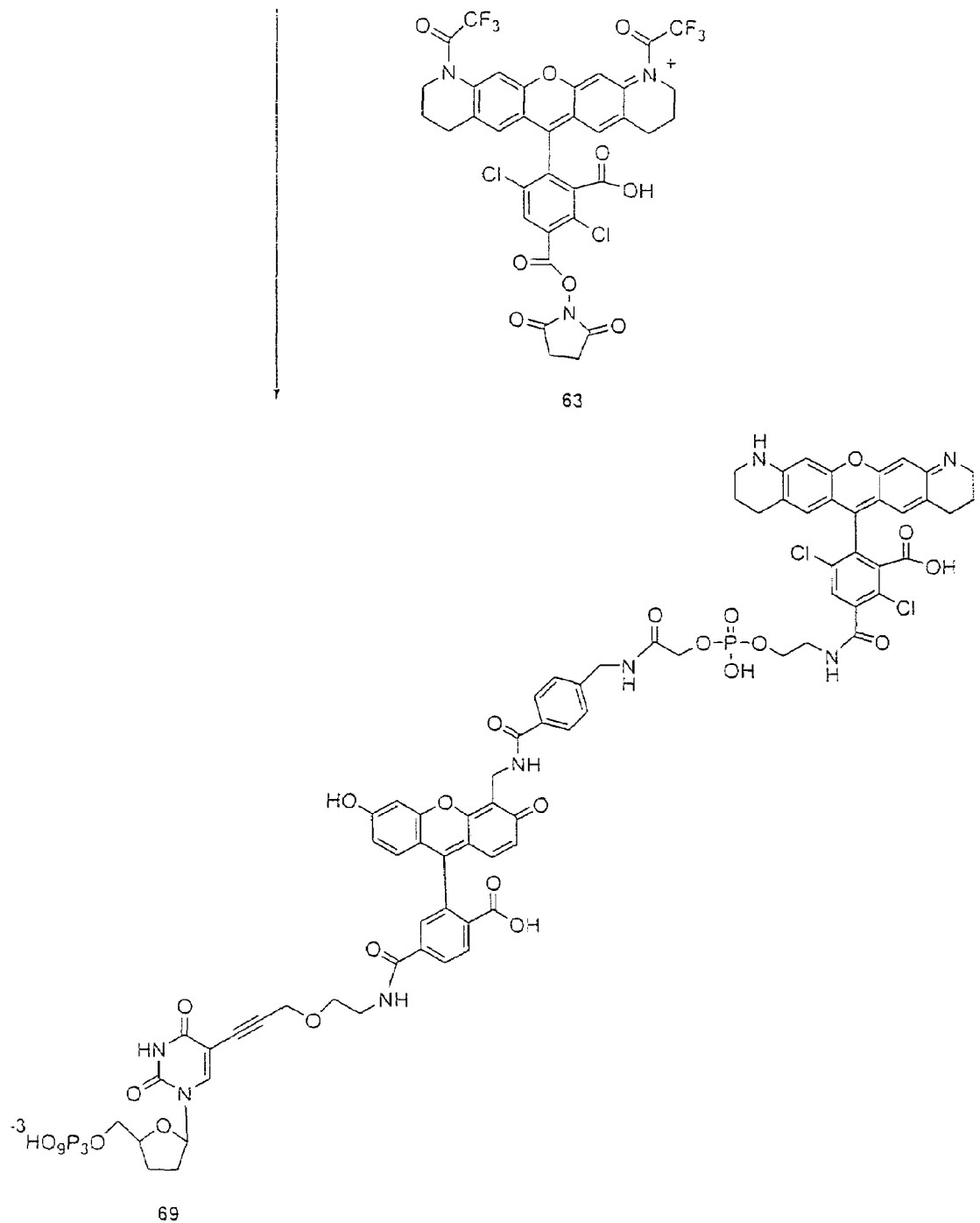
Figure 11A:
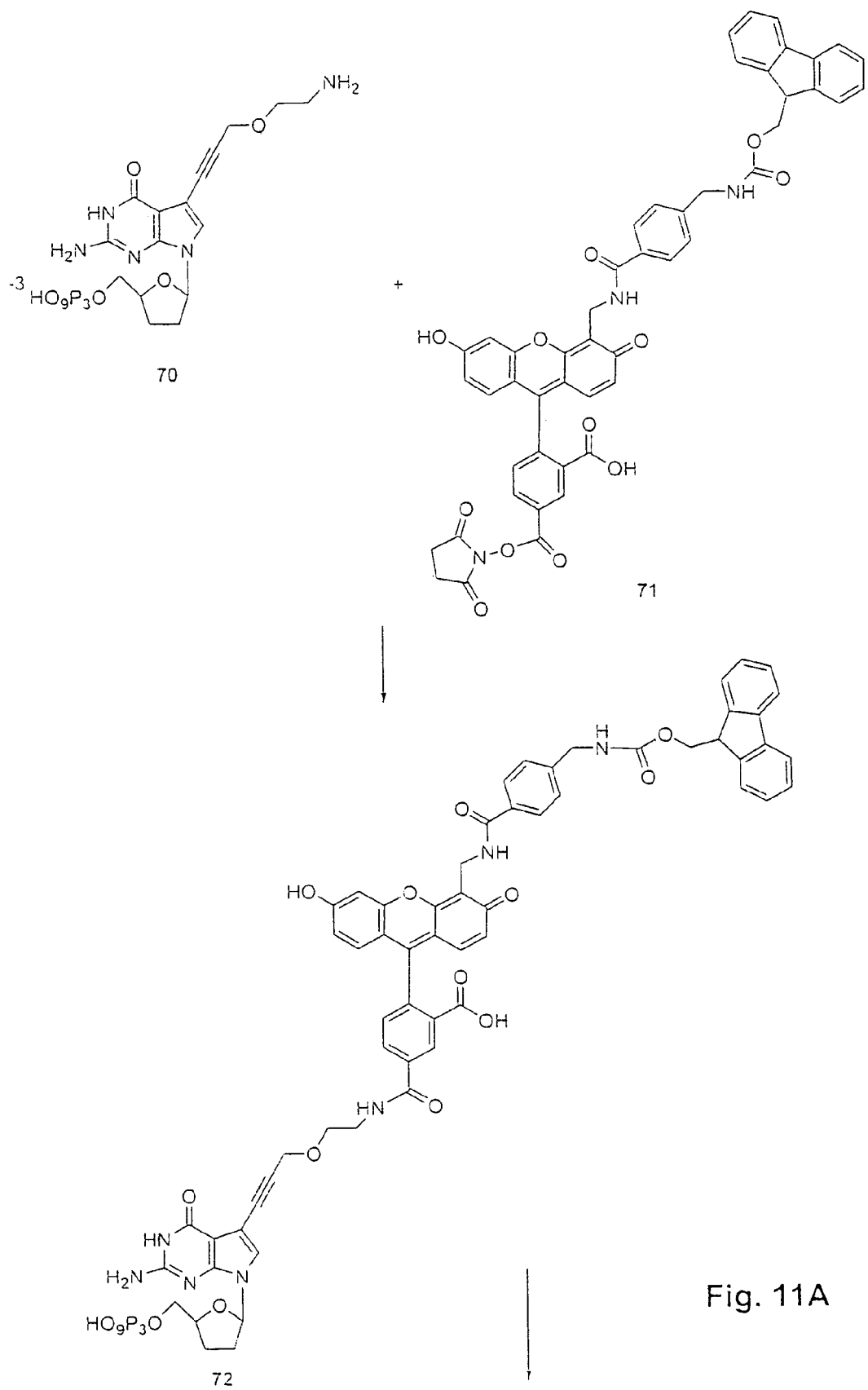
Figure 11B:
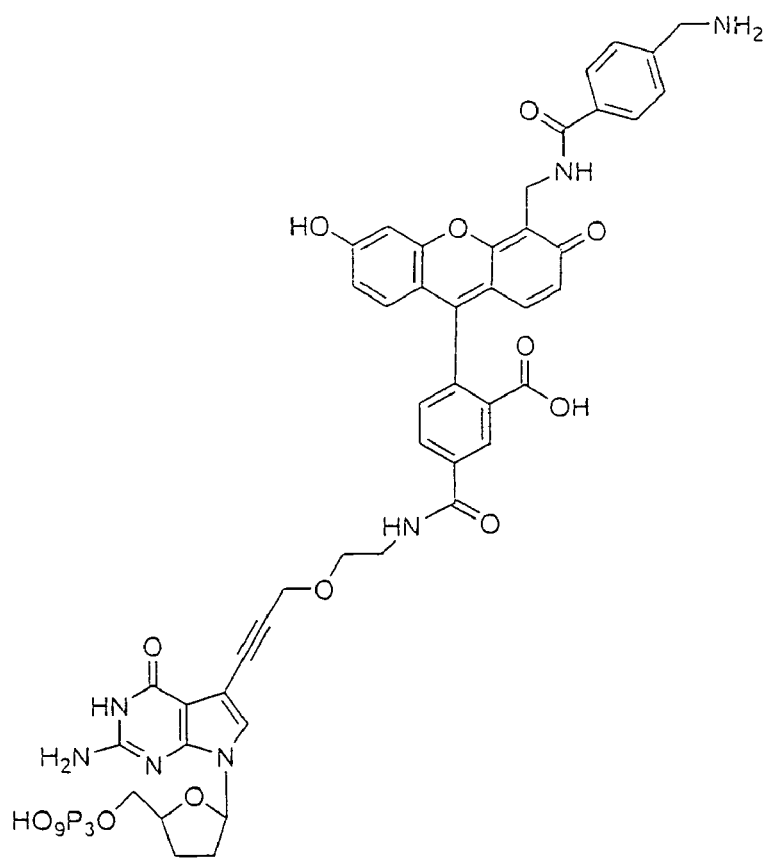
Figure 11B:
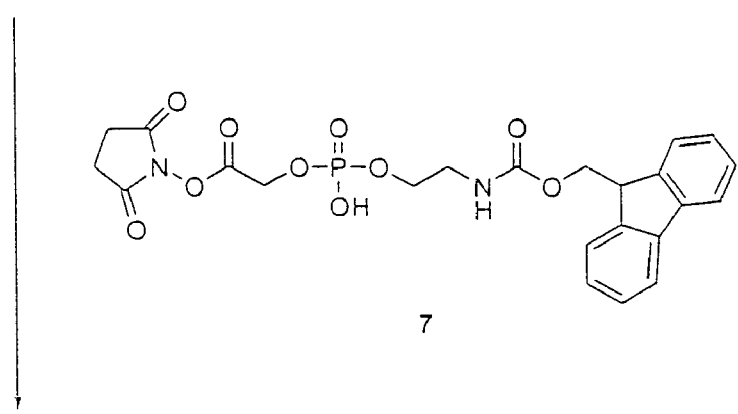
Figure 11C:
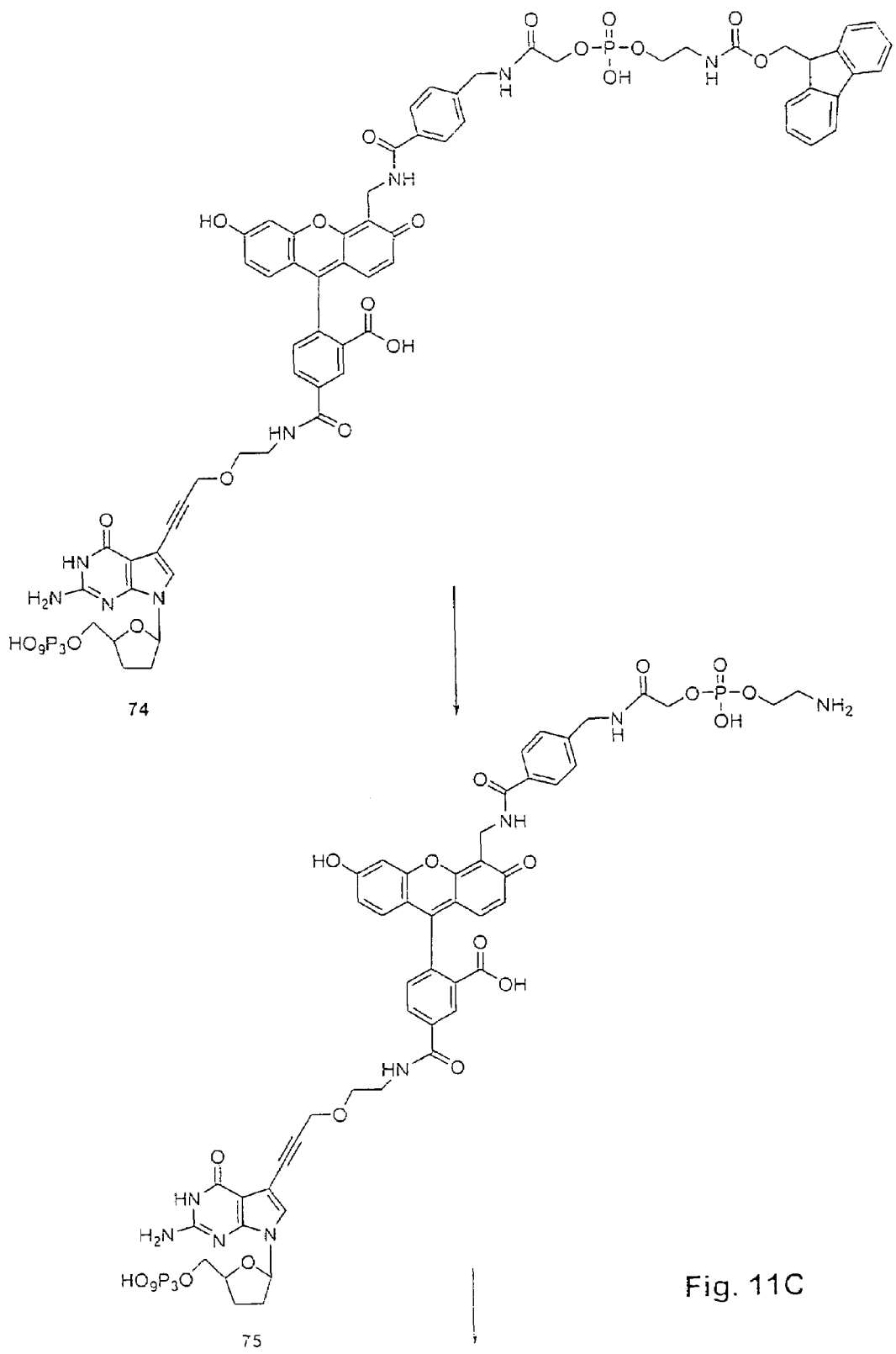
Figure 11D:
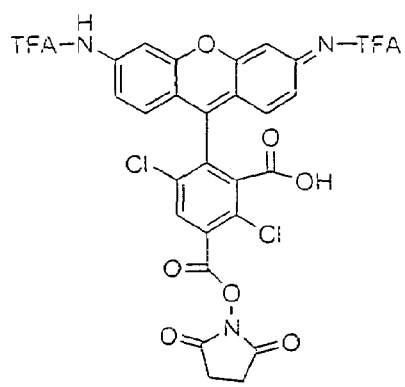
Figure 11D:
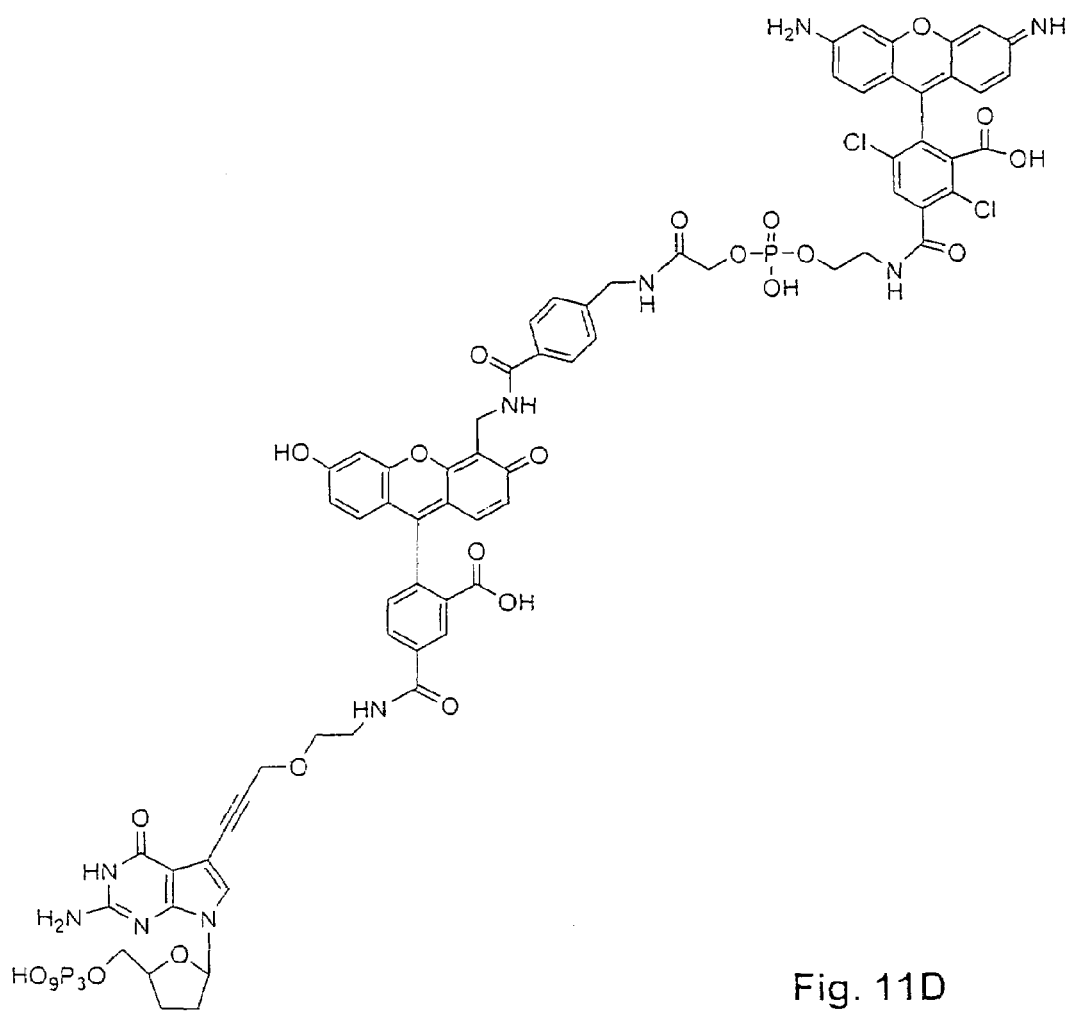
Figure 12A:
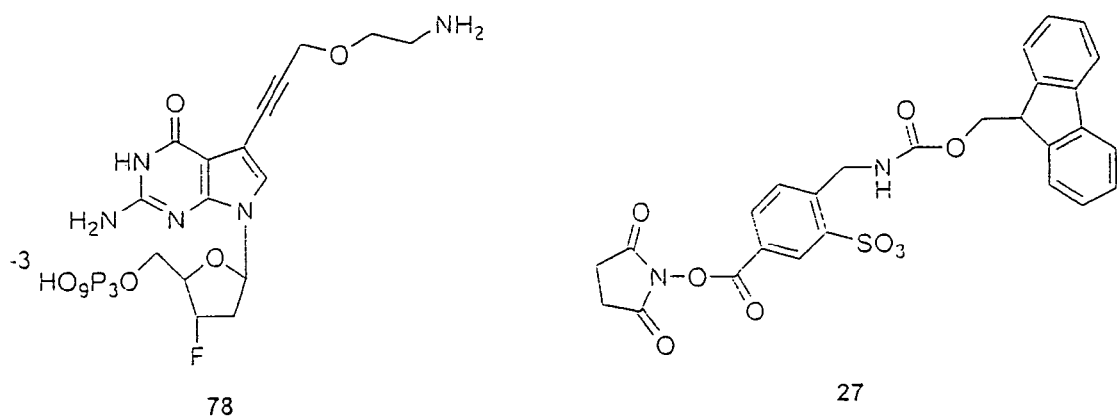
Figure 12A:
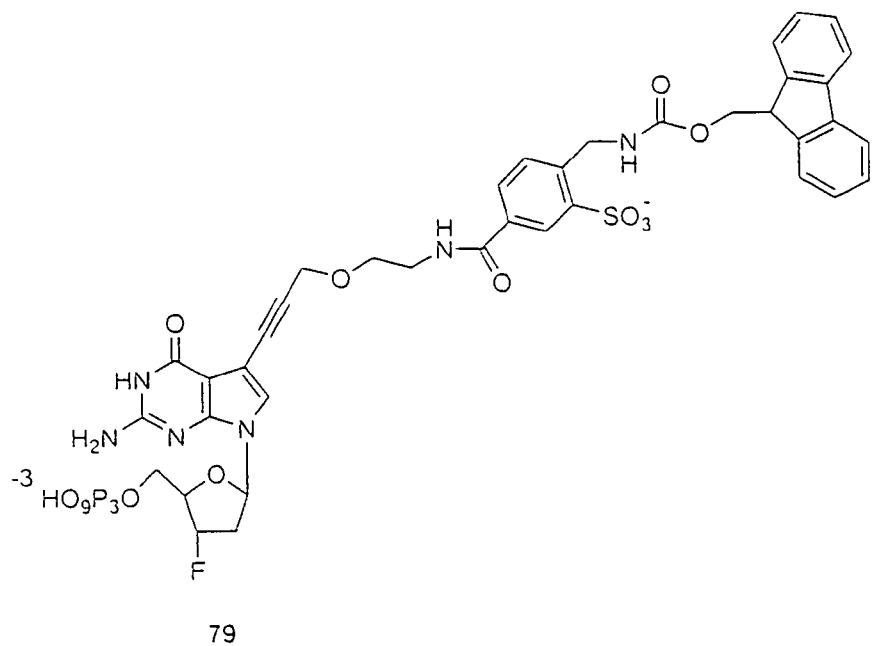
Figure 12B:
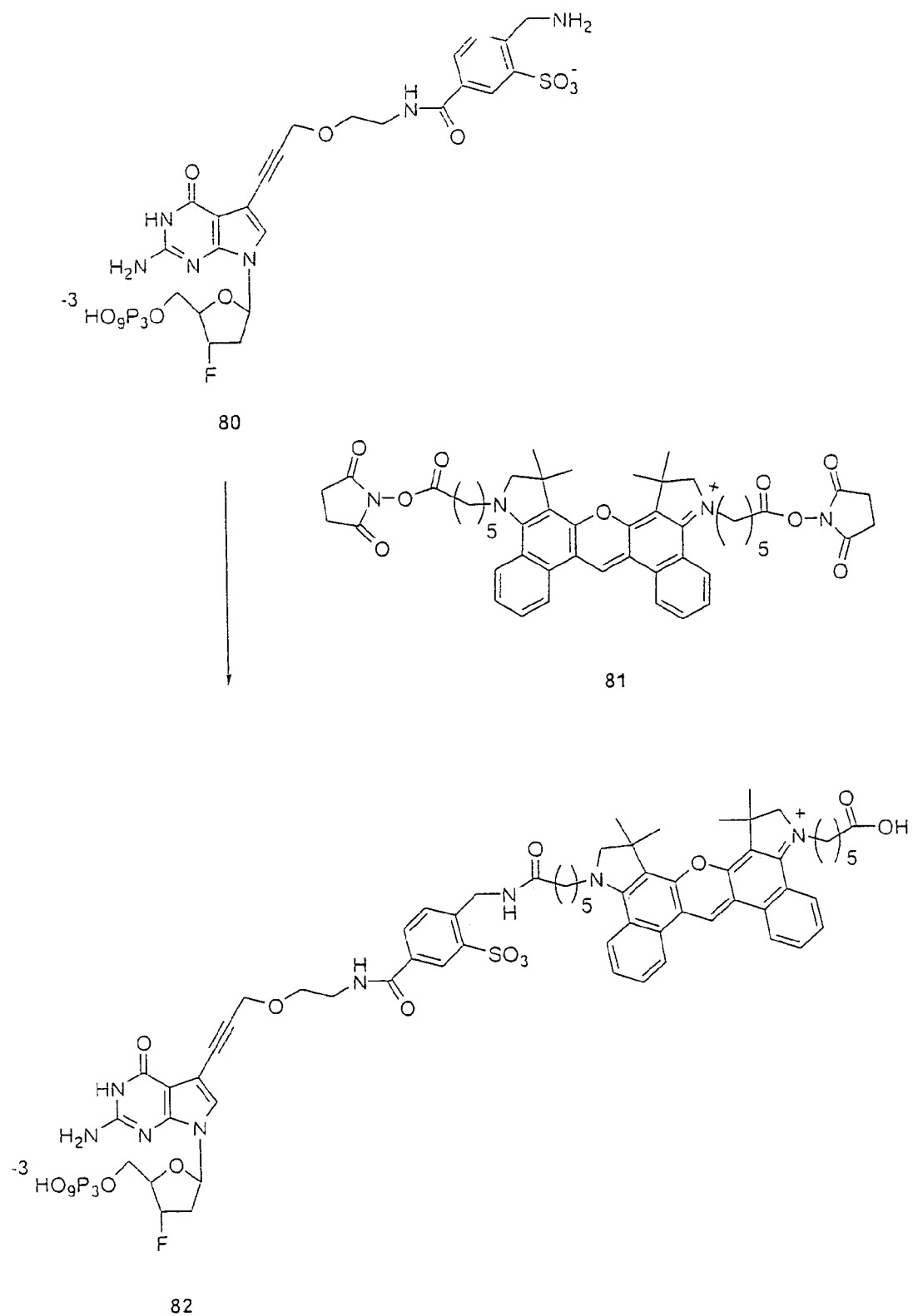
Figure 13A:
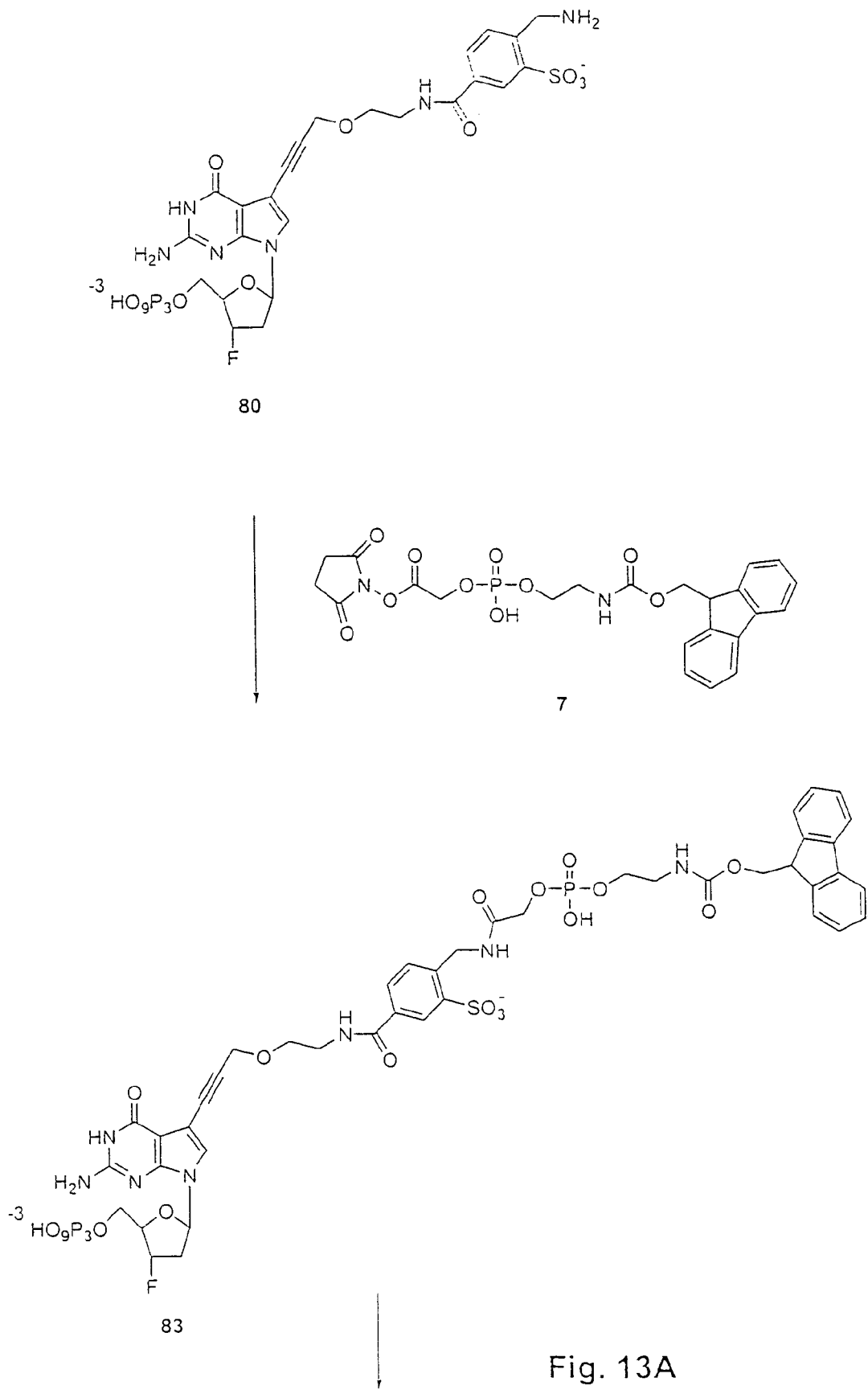
Figure 13B:
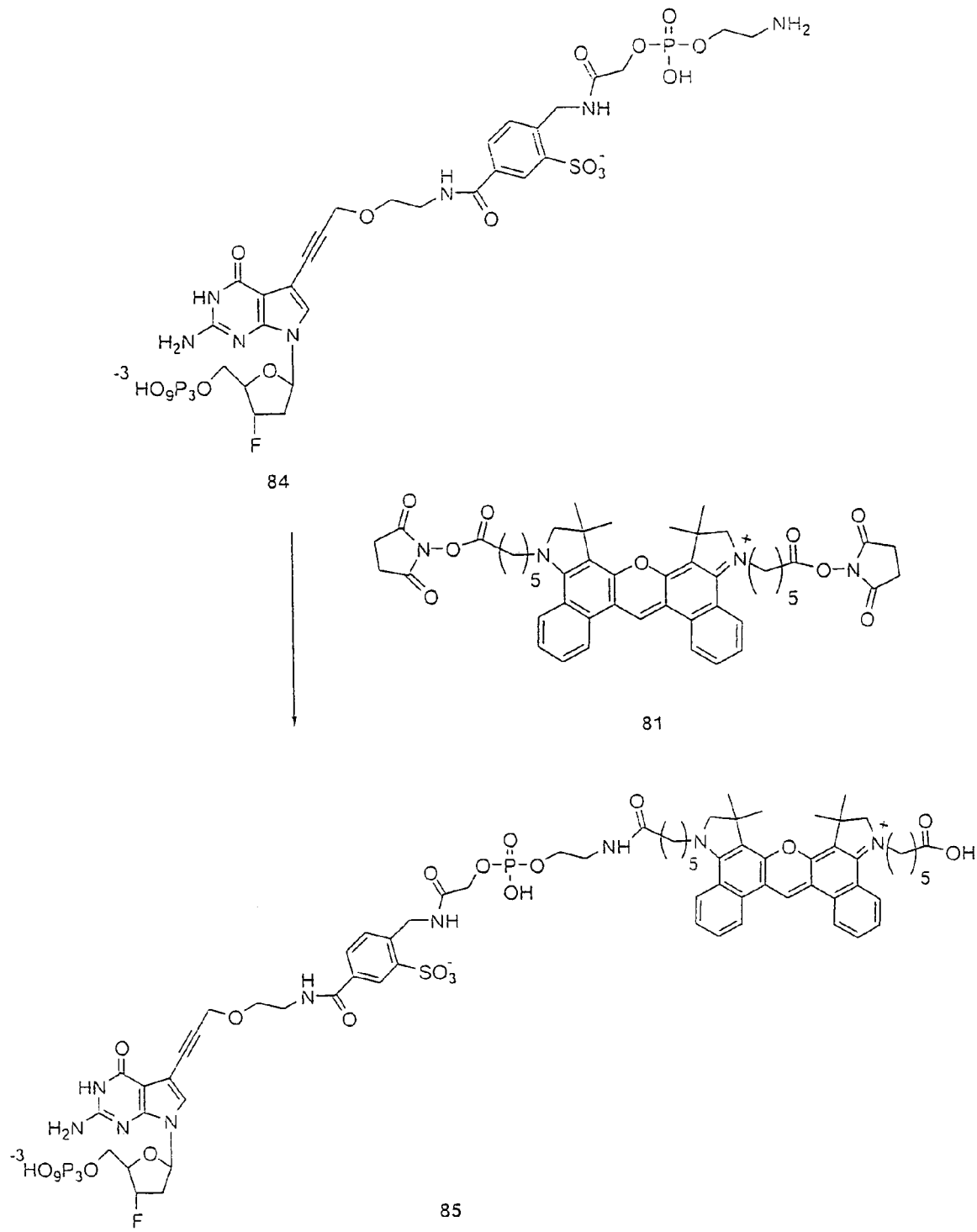
Figure 14A:
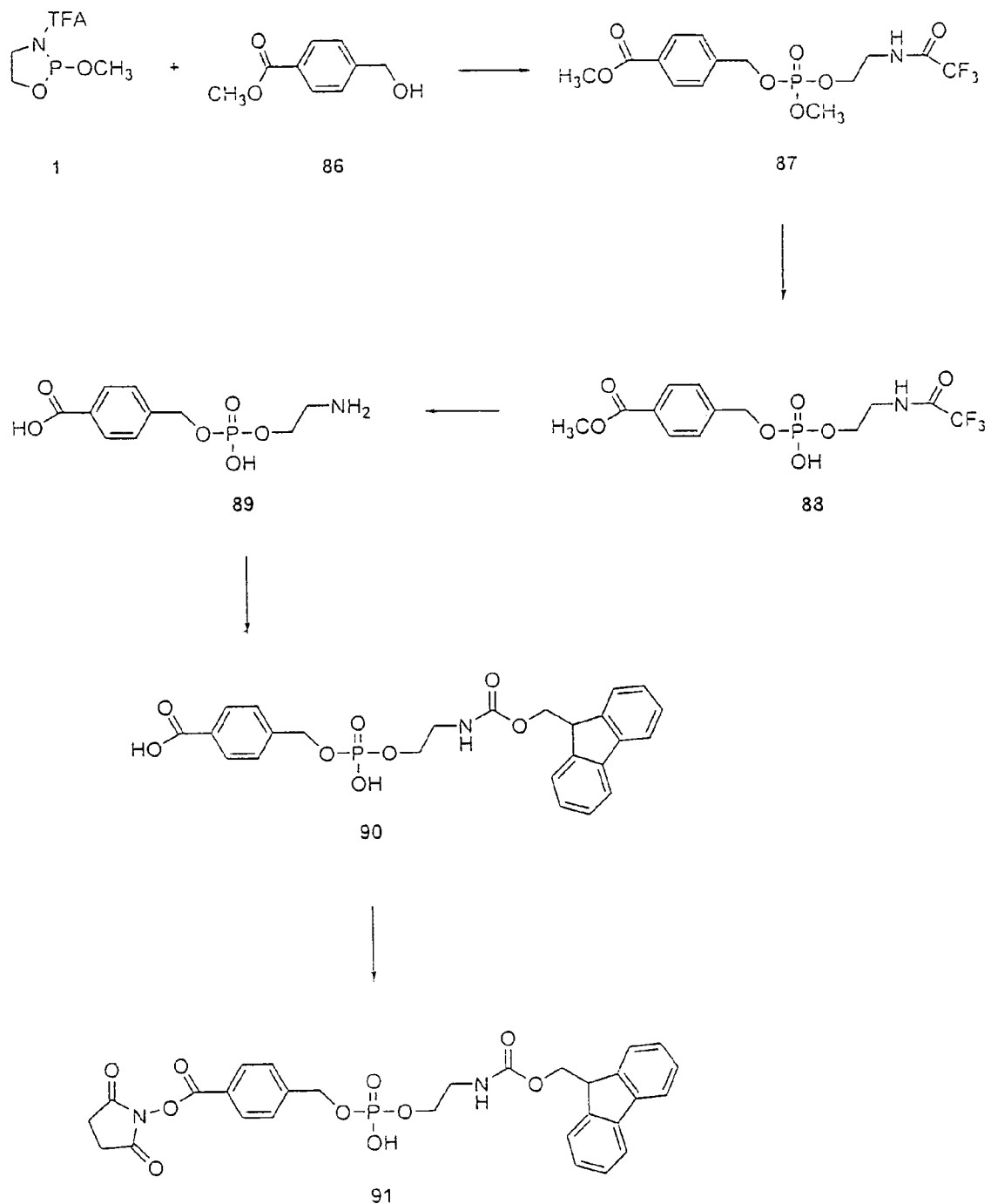
Figure 14B:
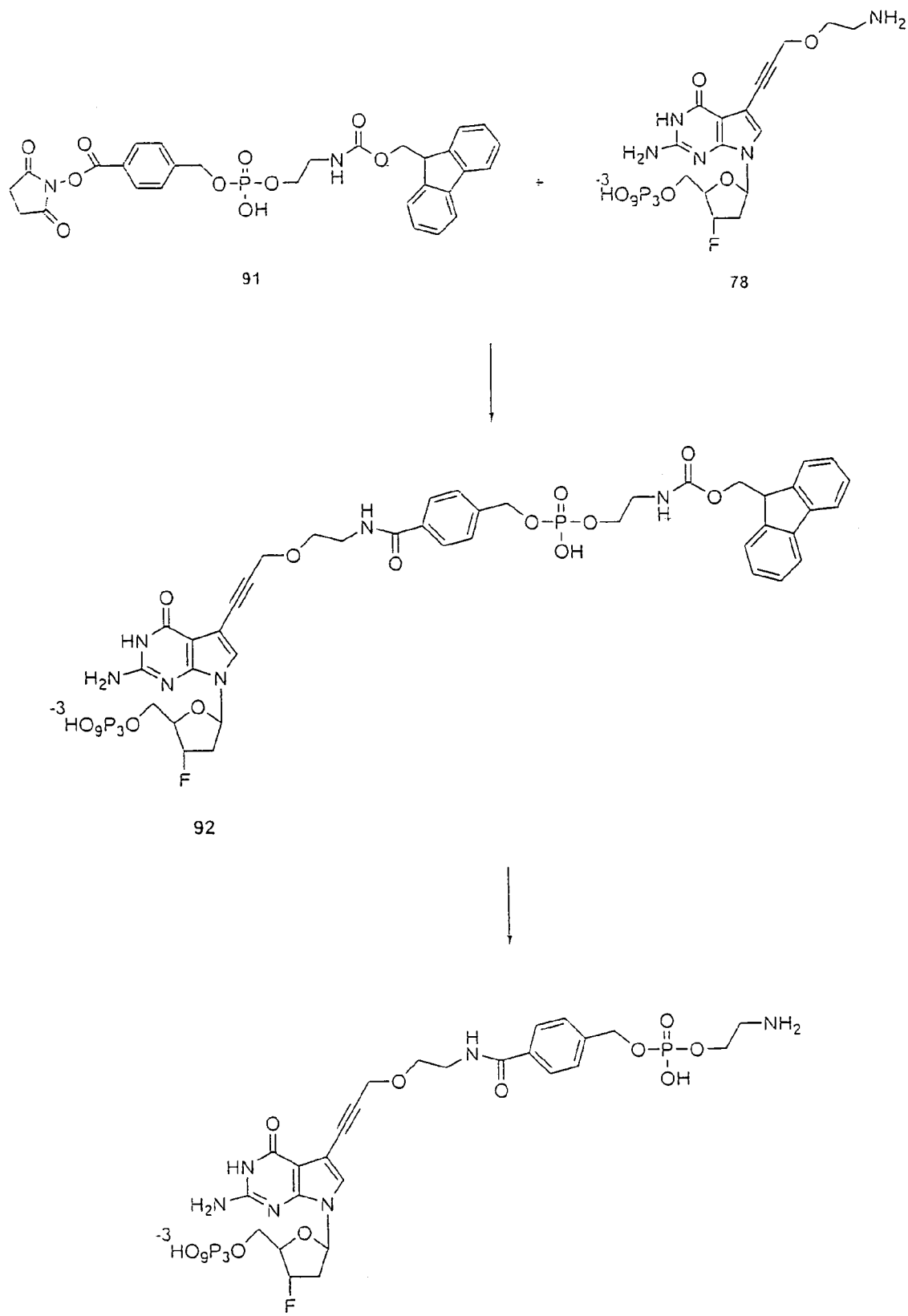
Figure 14C:
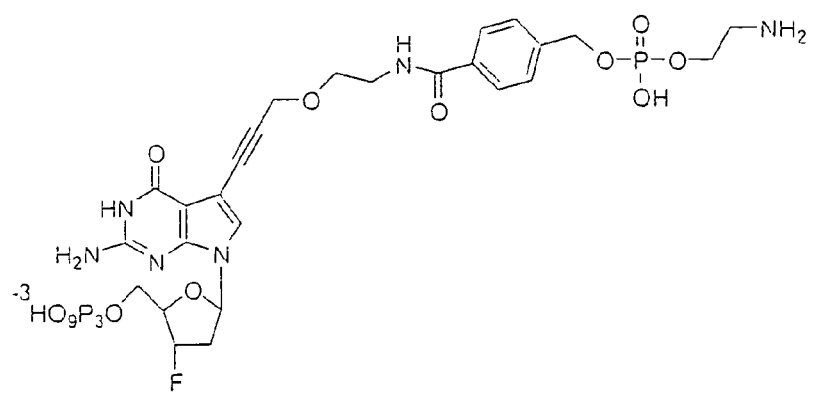
Figure 14C:
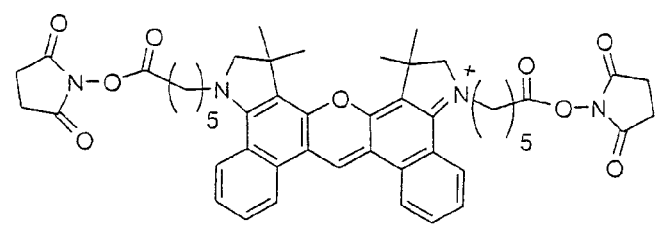
Figure 14C:
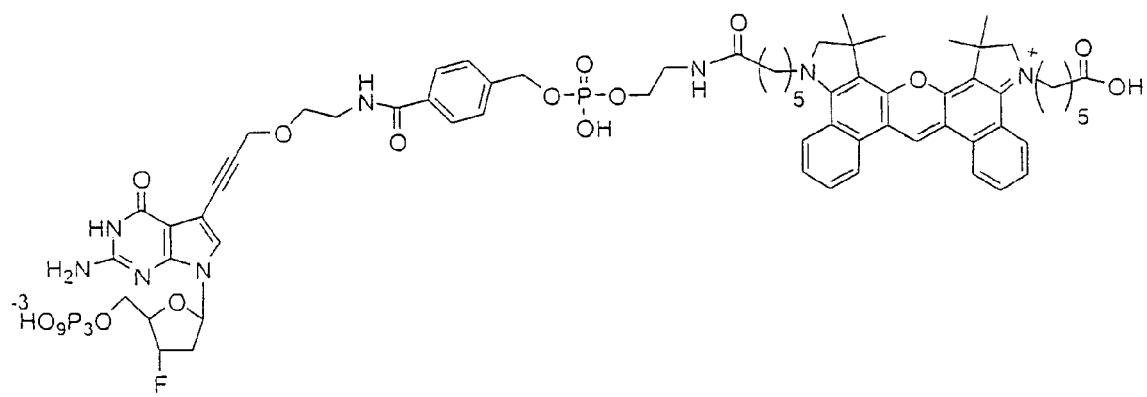
Figure 15A:
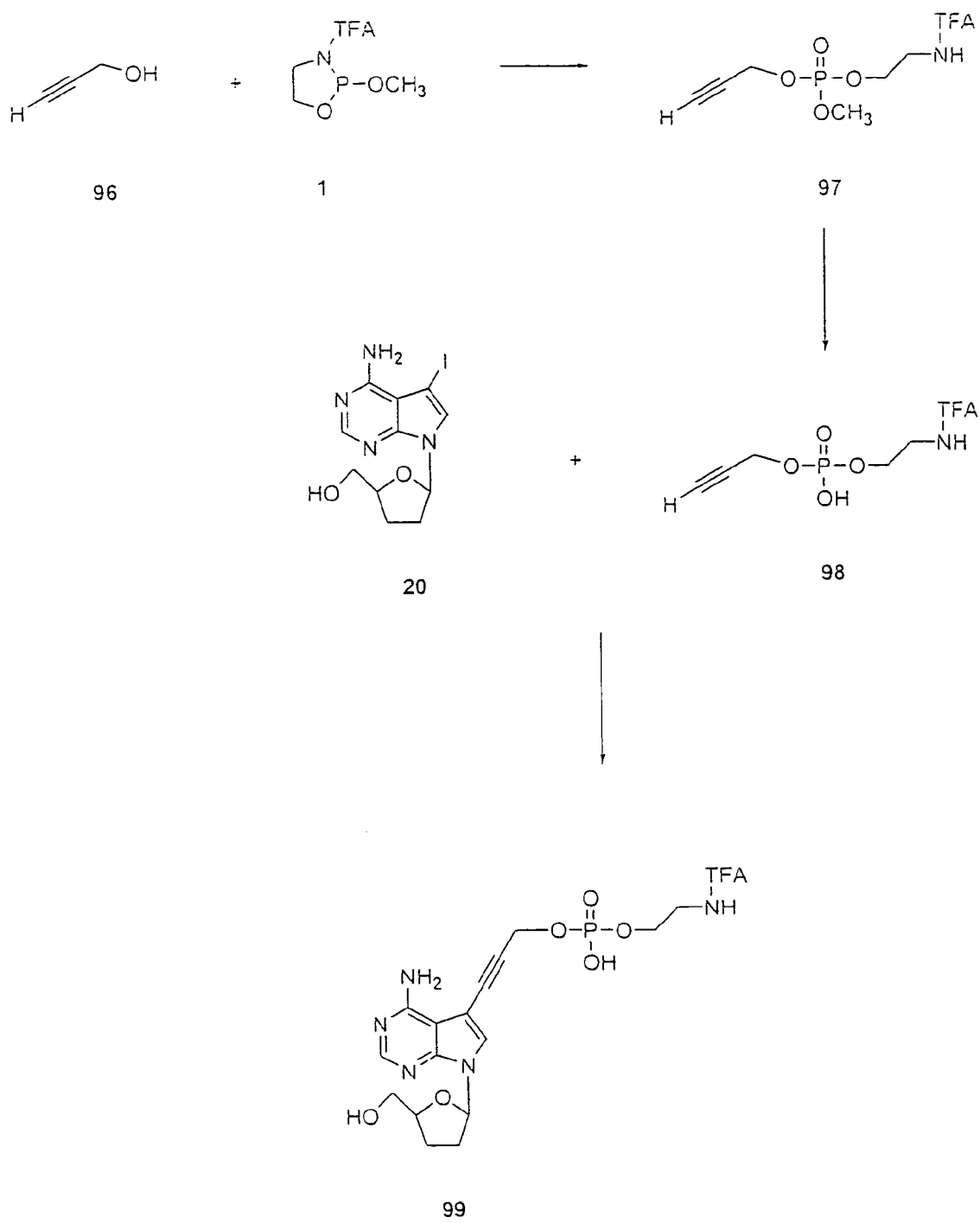
Figure 15B:
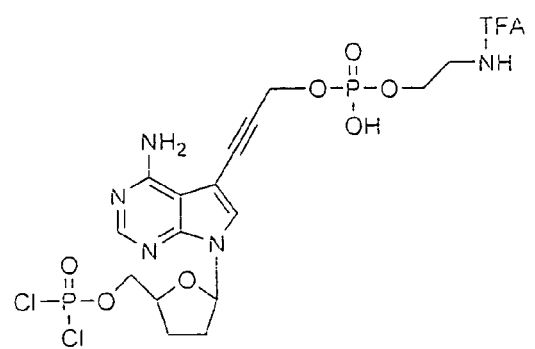
Figure 15B:
Figure 15B:
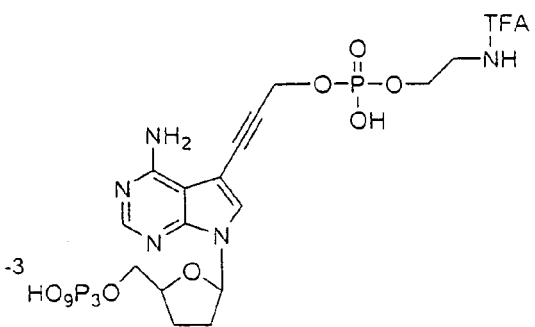
Figure 15B:
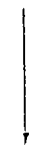
Figure 15B:
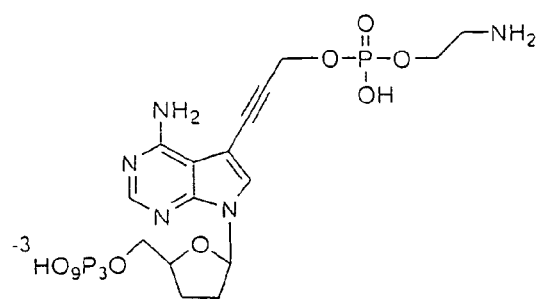
Figure 15C:
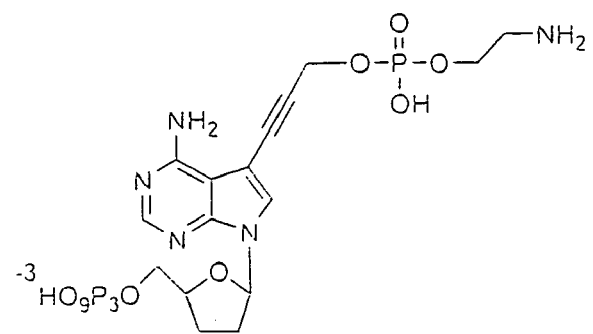
Figure 15C:
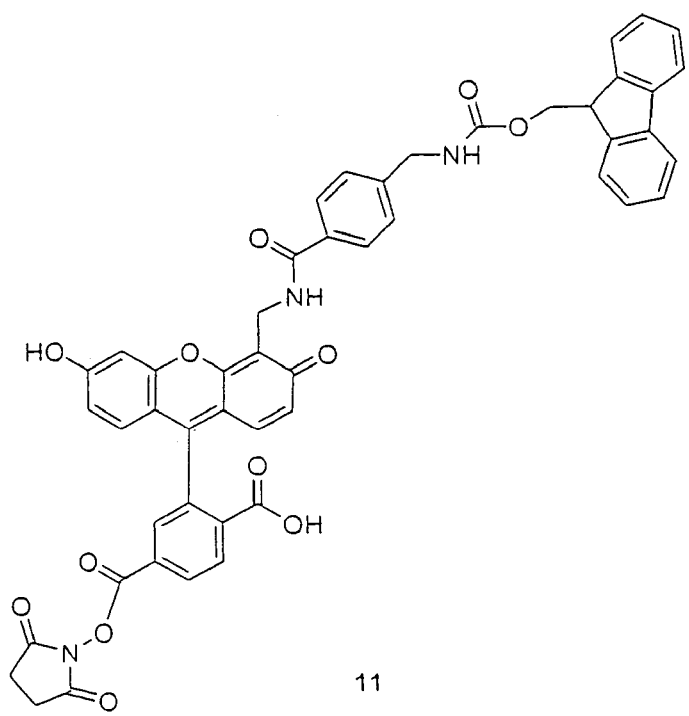
Figure 15C:
Figure 15D:
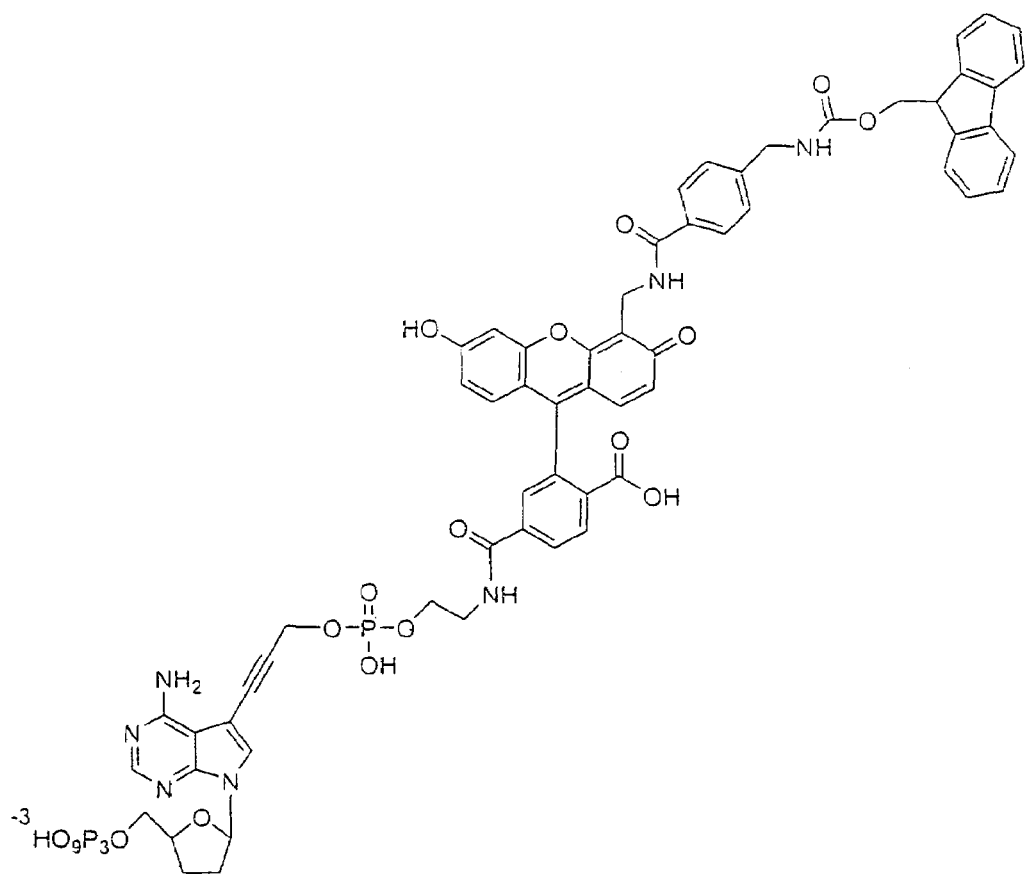
Figure 15D:
Figure 15E:
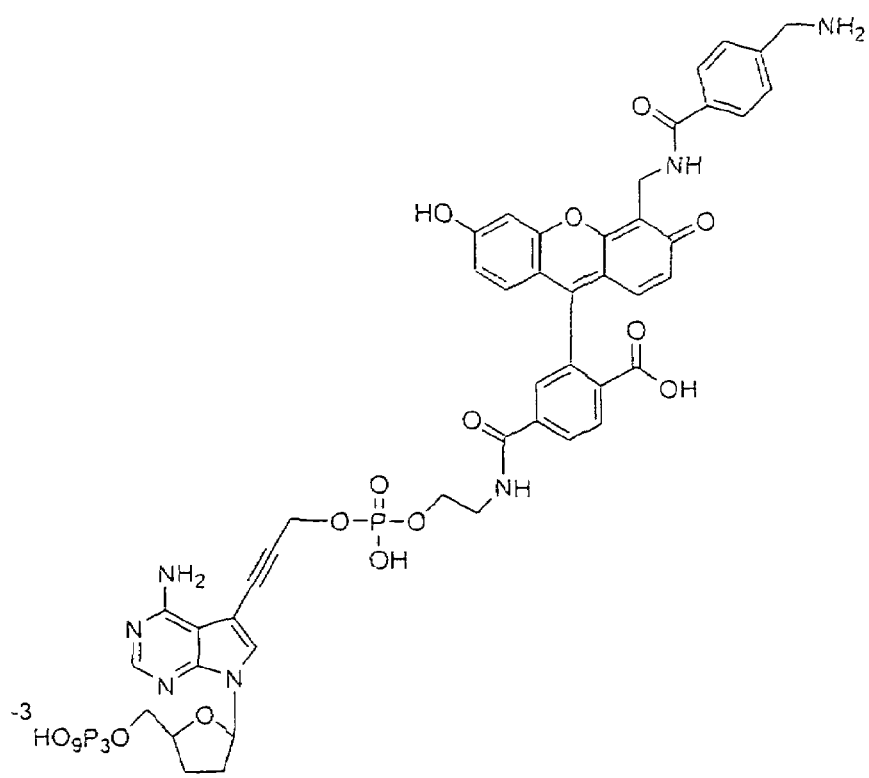
Figure 15E:
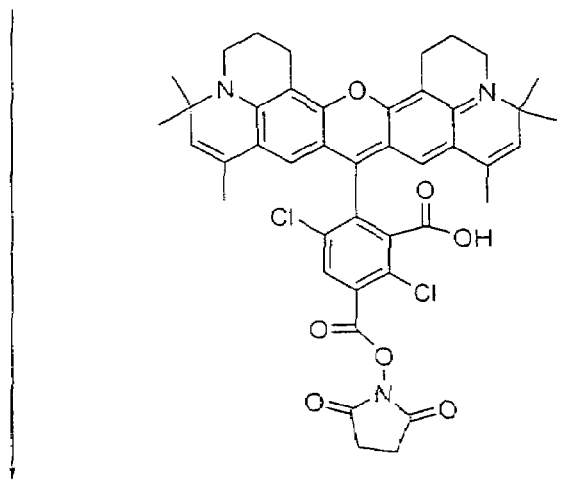
Figure 15F:
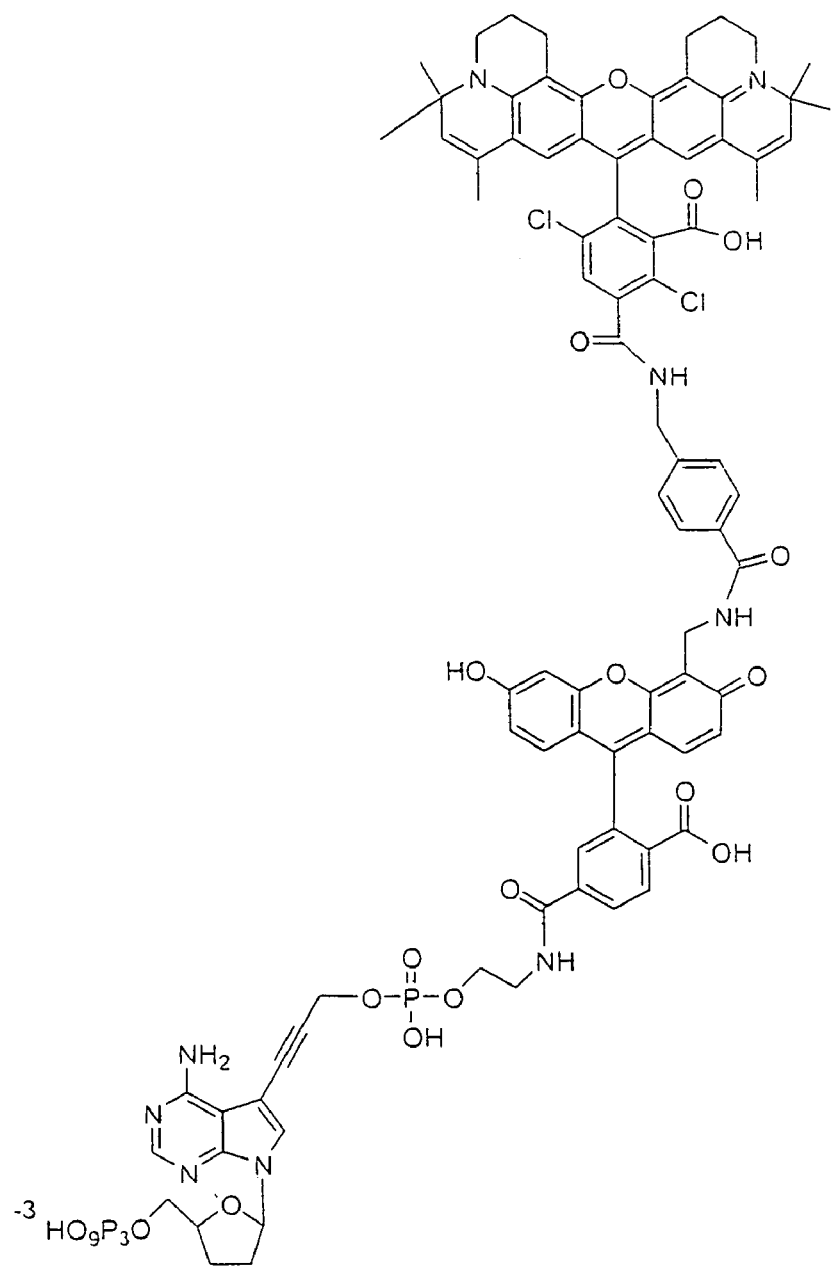
Figure 16A:
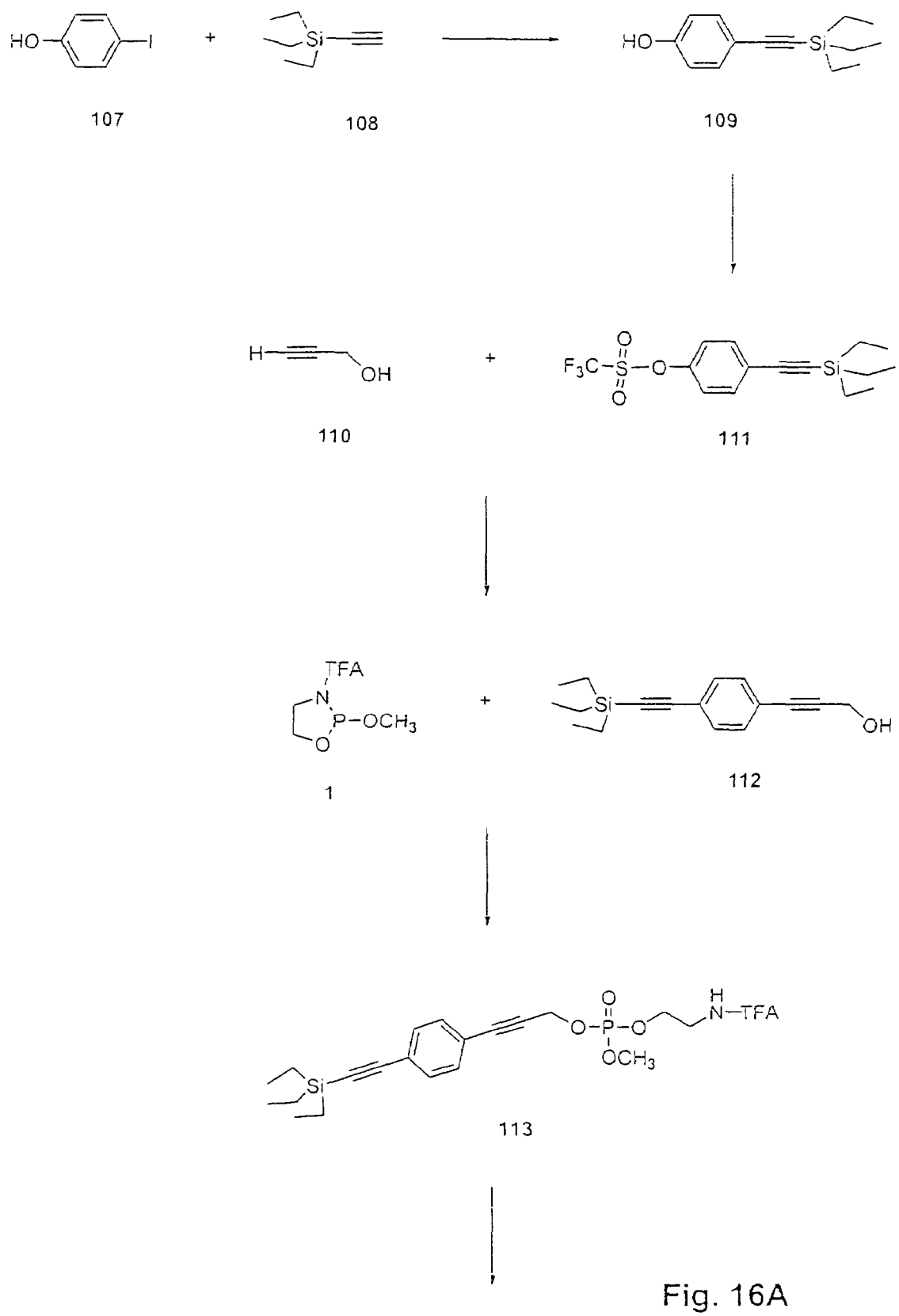
Figure 16B:
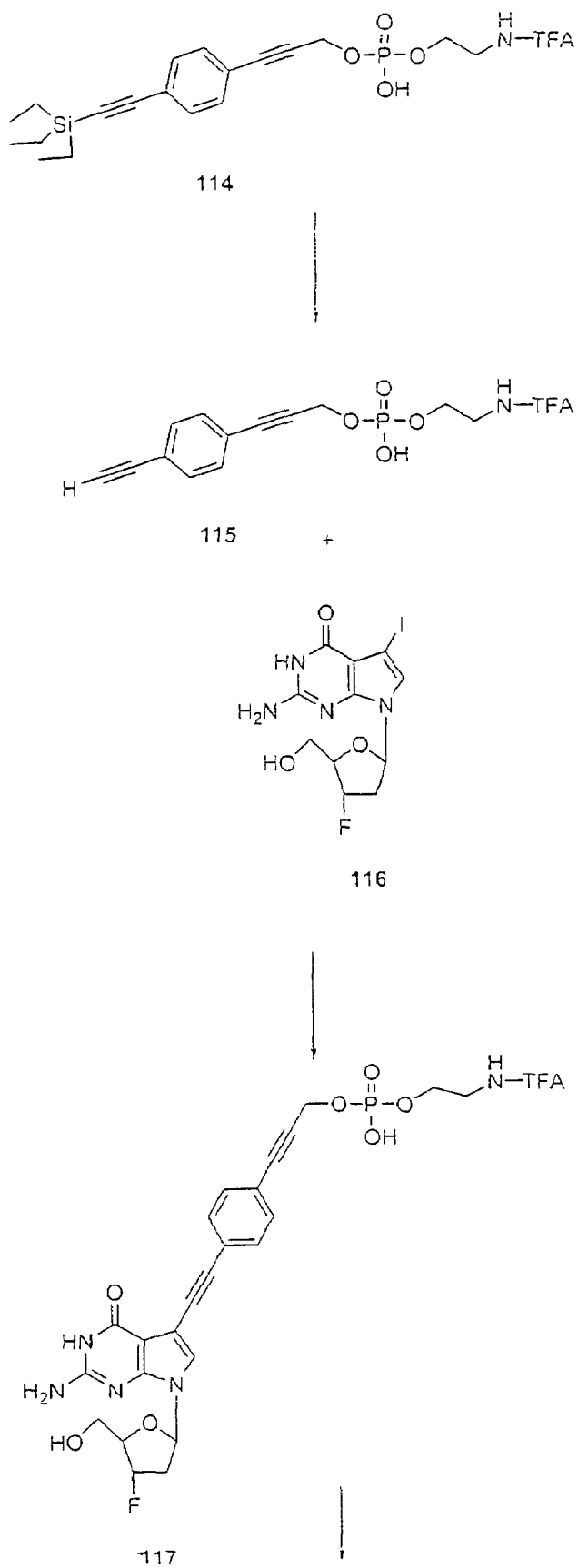
Figure 16C:
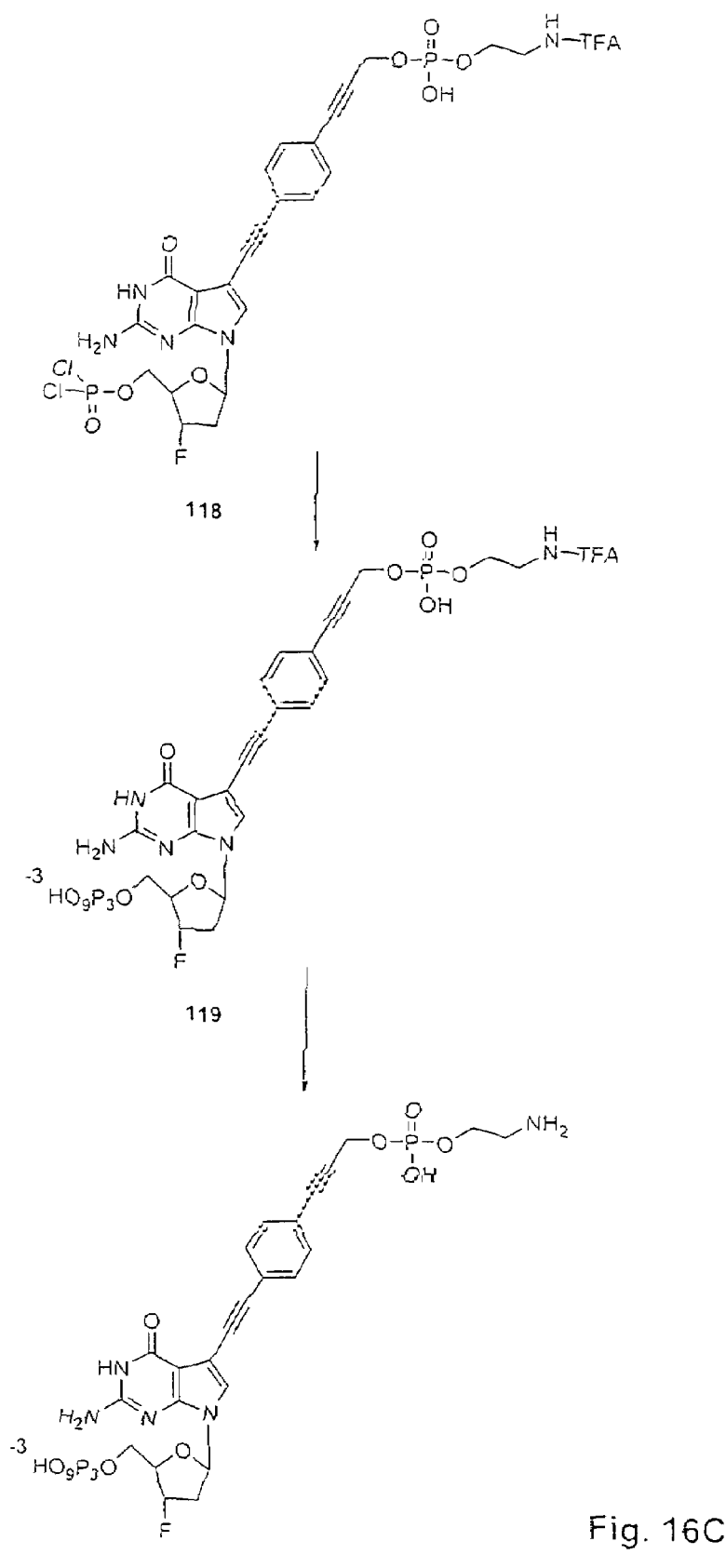
Figure 16D:
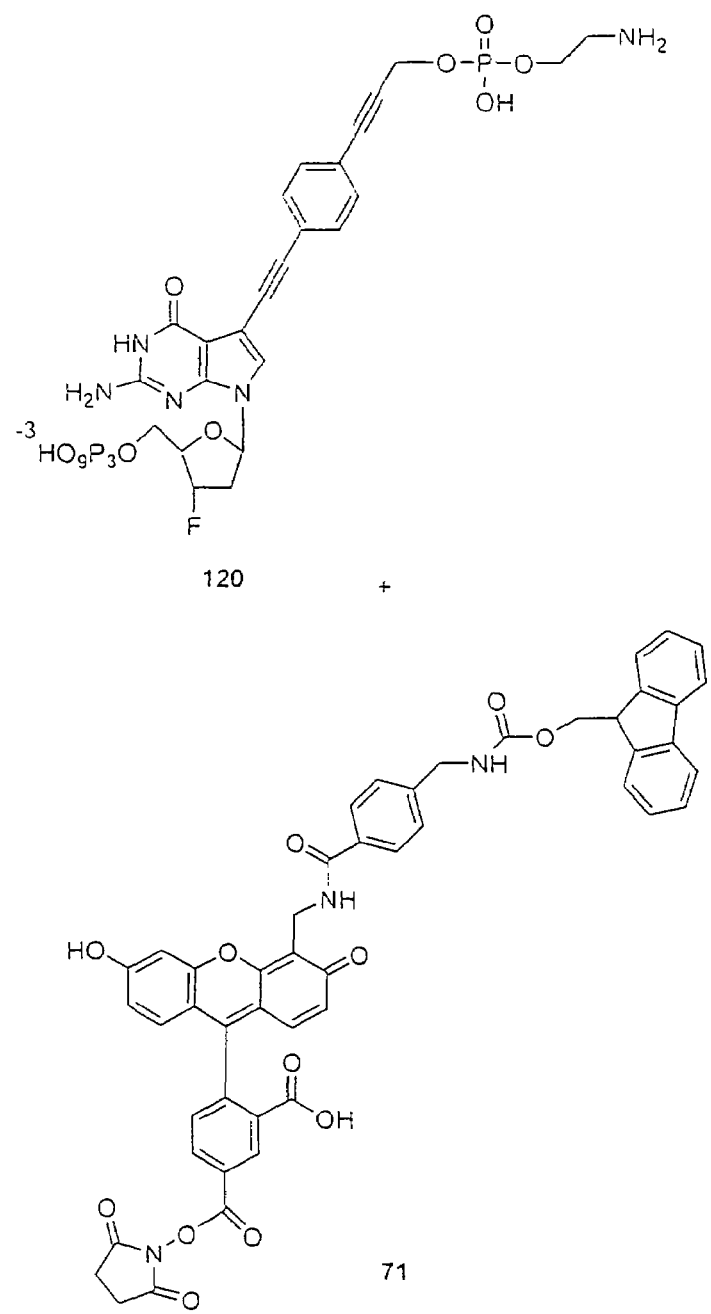
Figure 16D:
Figure 16E:
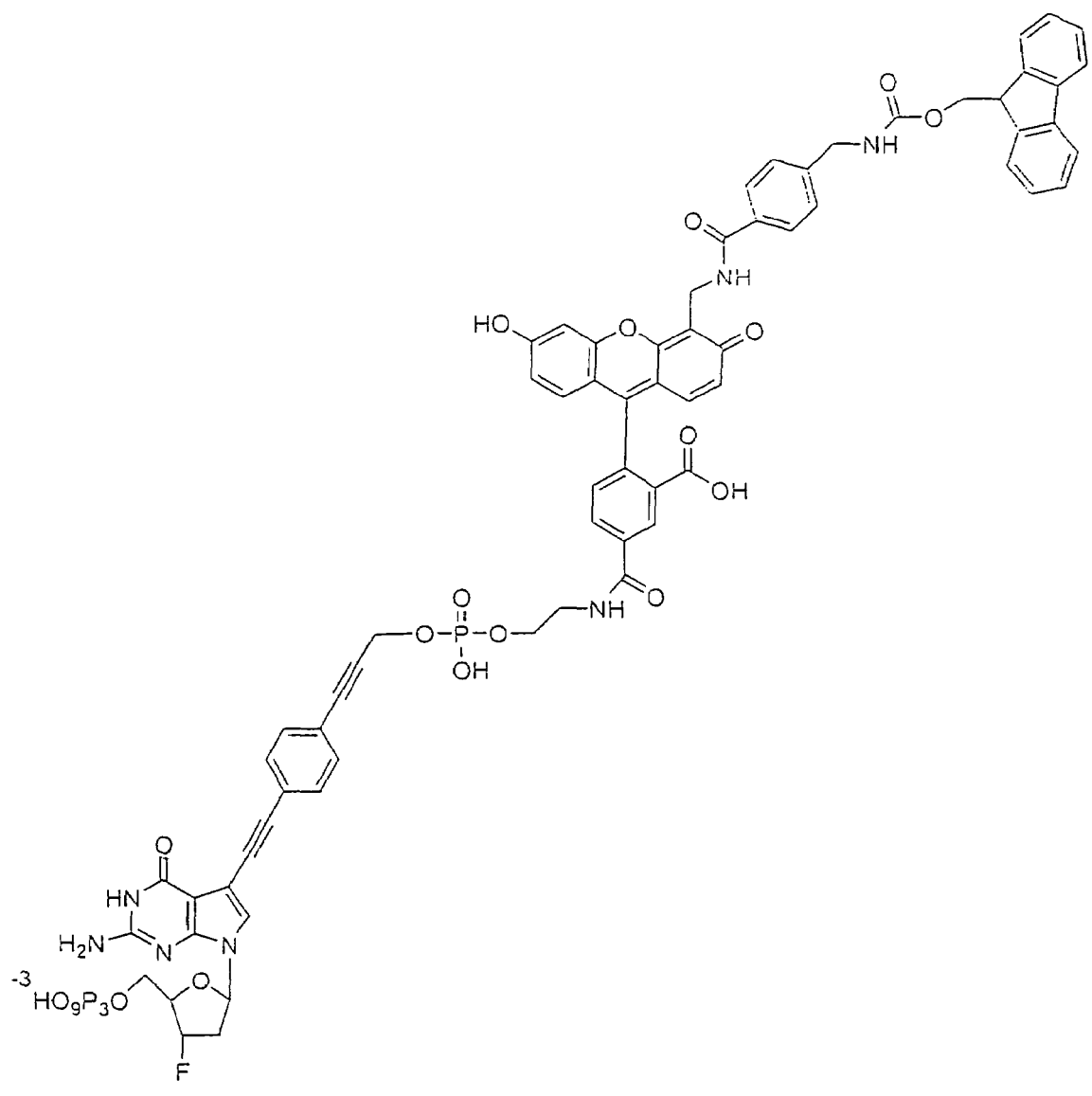
Figure 16F:
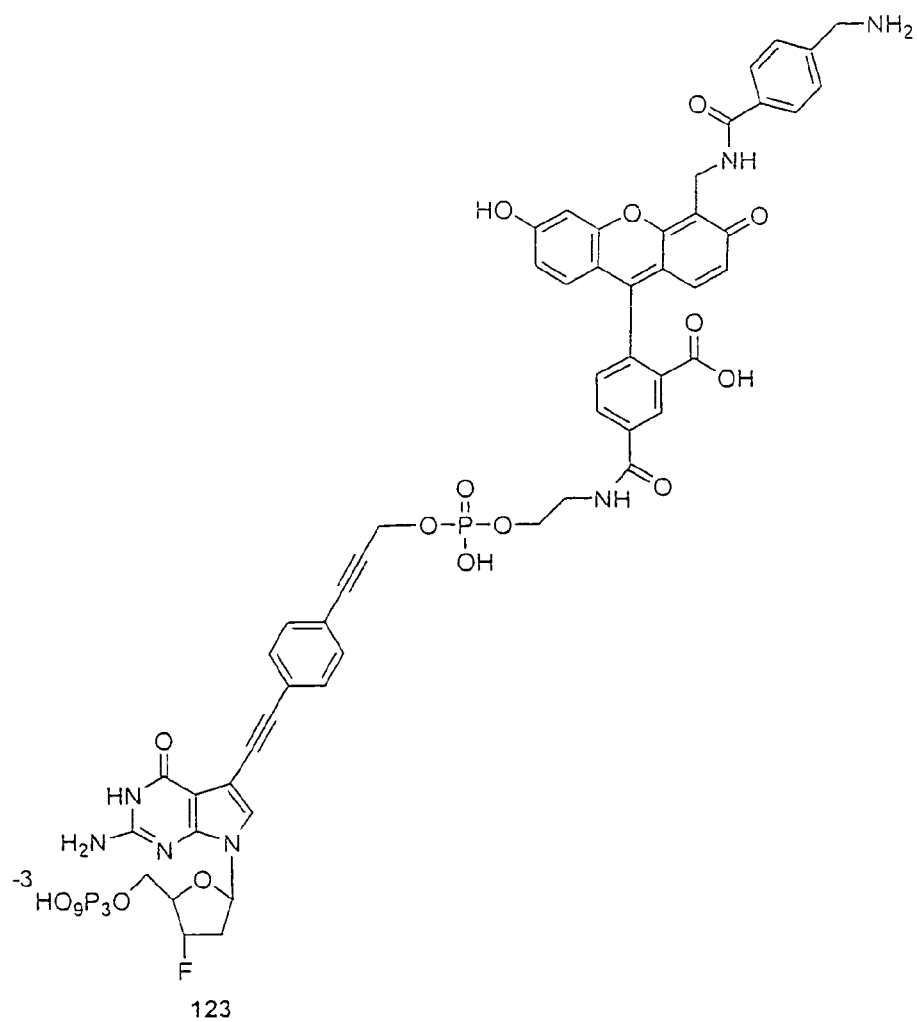
Figure 16F:
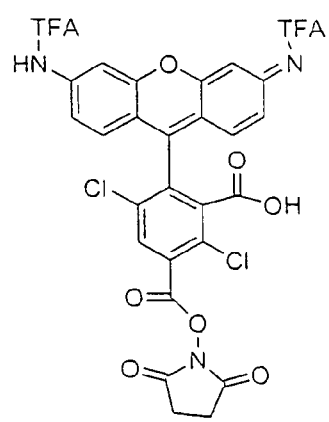
Figure 16G:
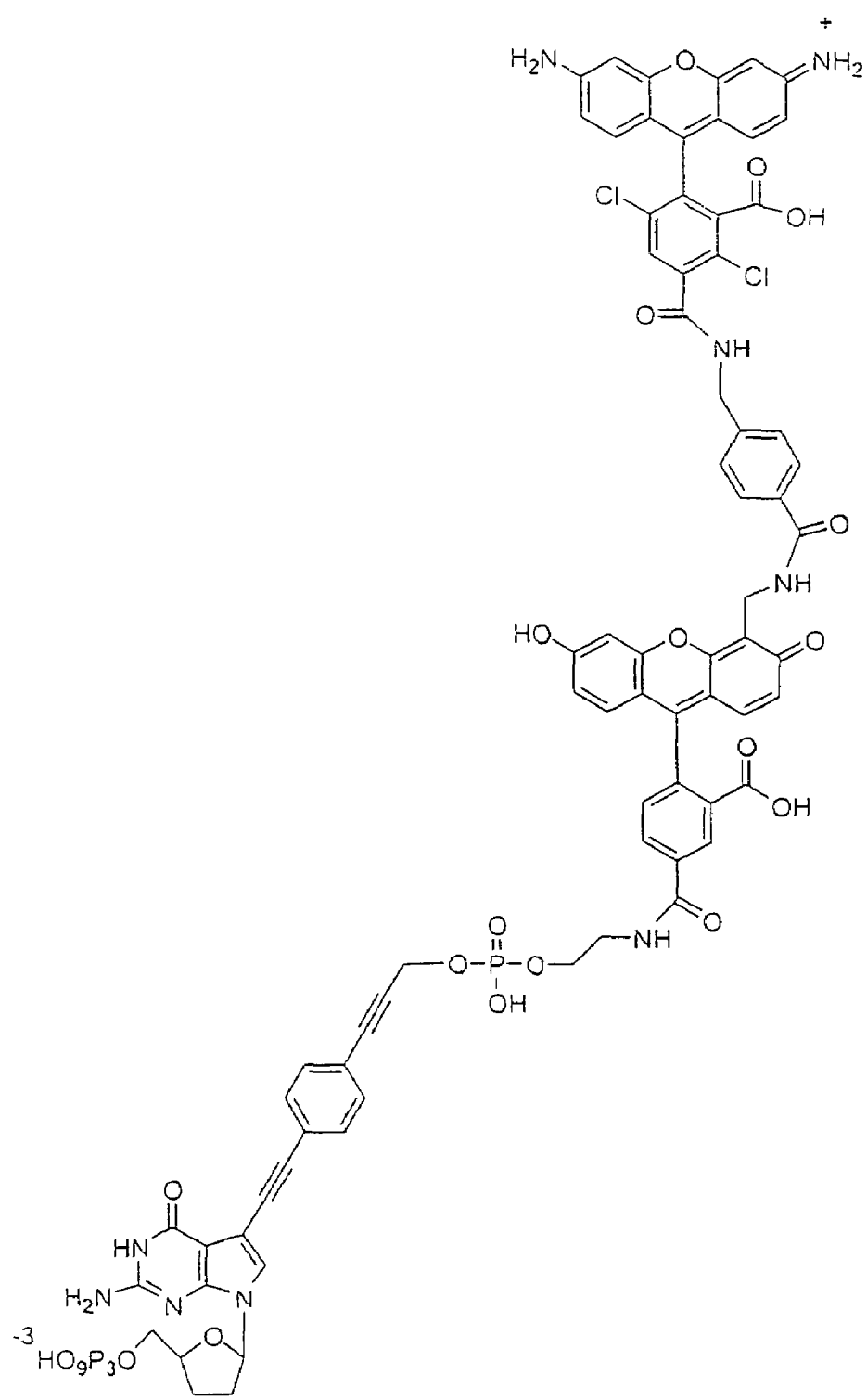
Figure 17A:
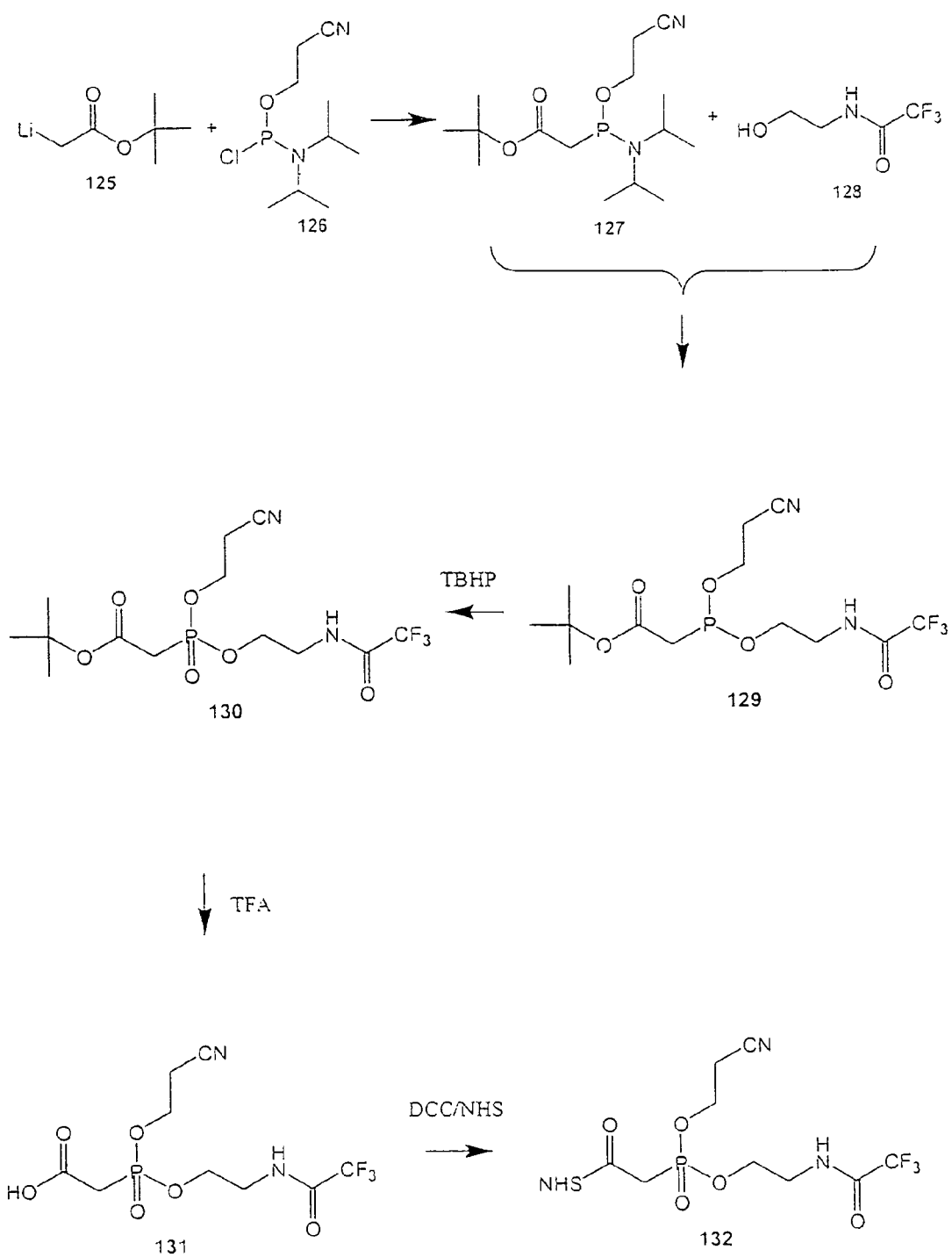
Figure 17B:
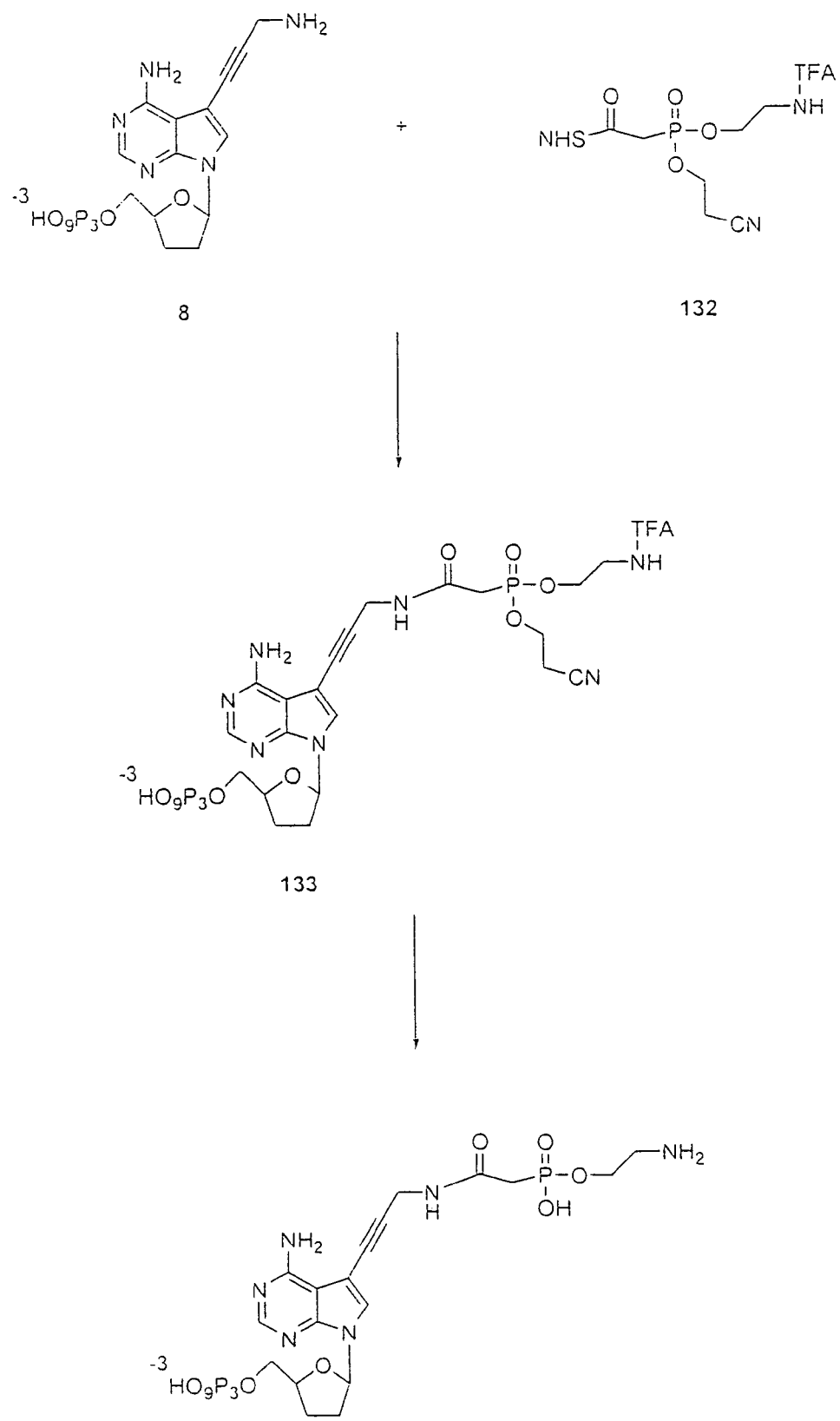
Figure 17C:
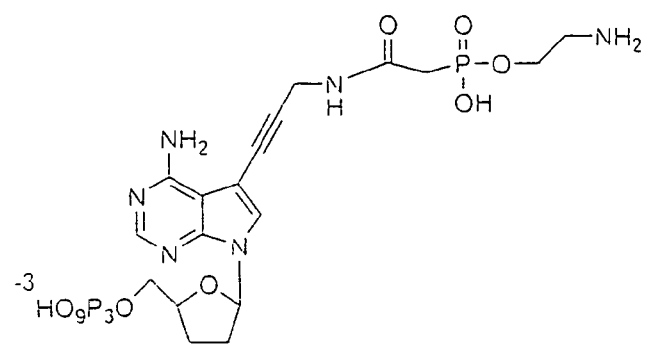
Figure 17C:
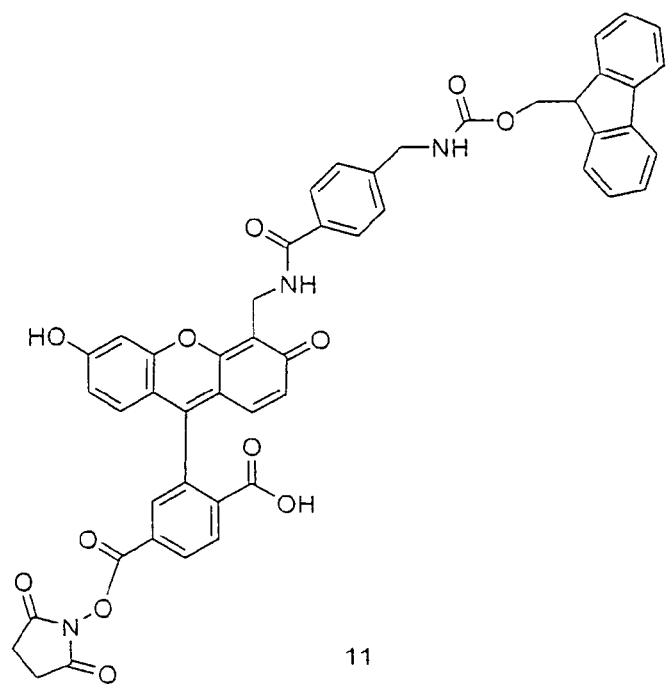
Figure 17C:
Figure 17D:
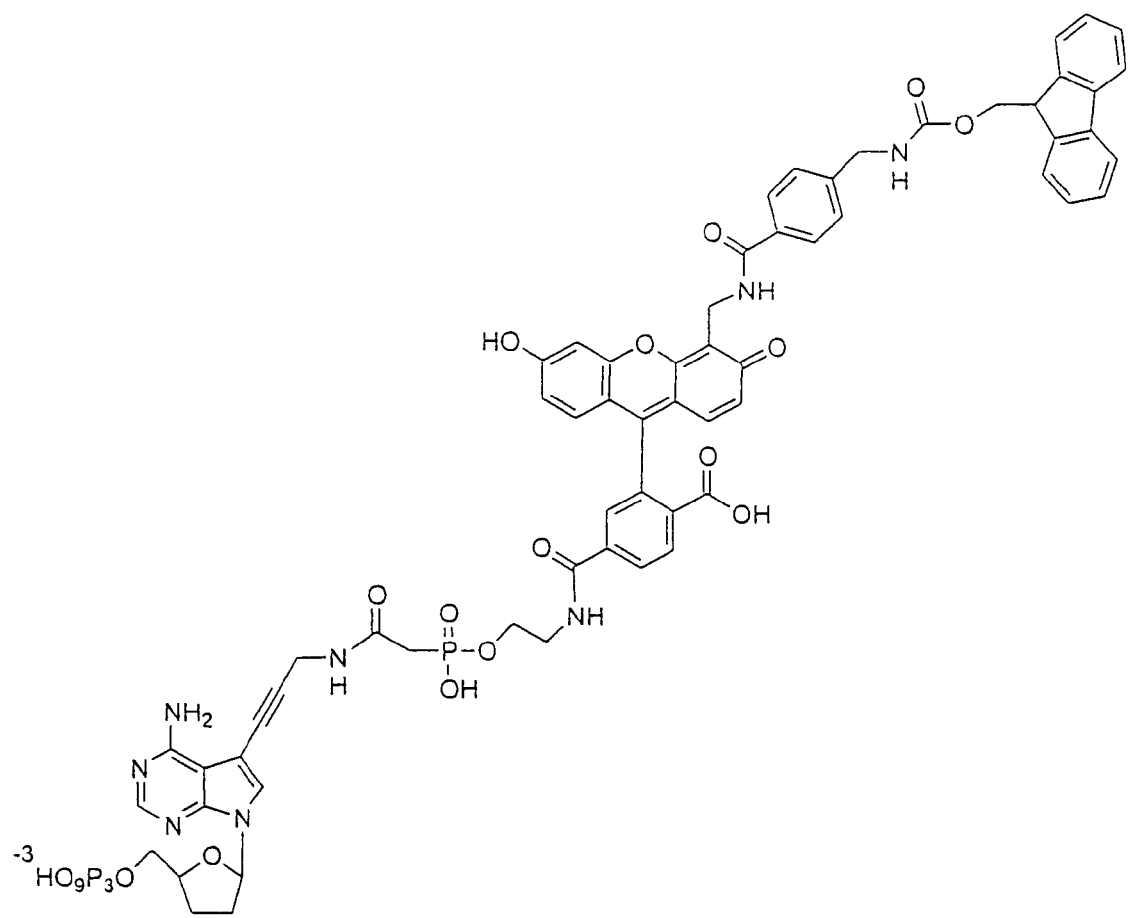
Figure 17D:
Figure 17E:
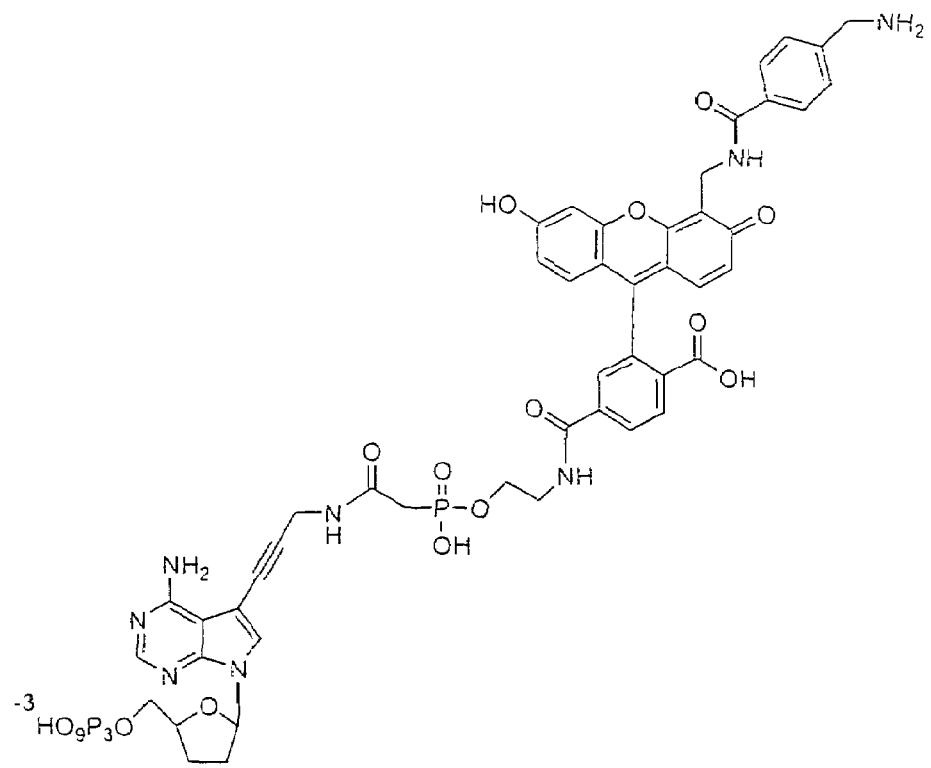
Figure 17E:
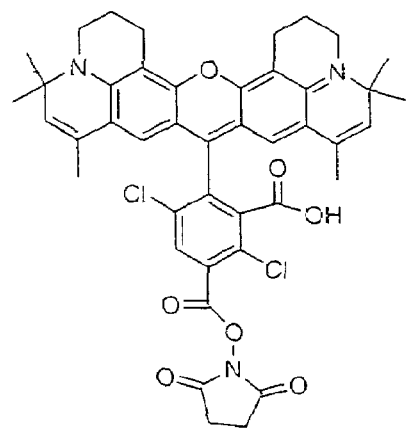
Figure 17F:
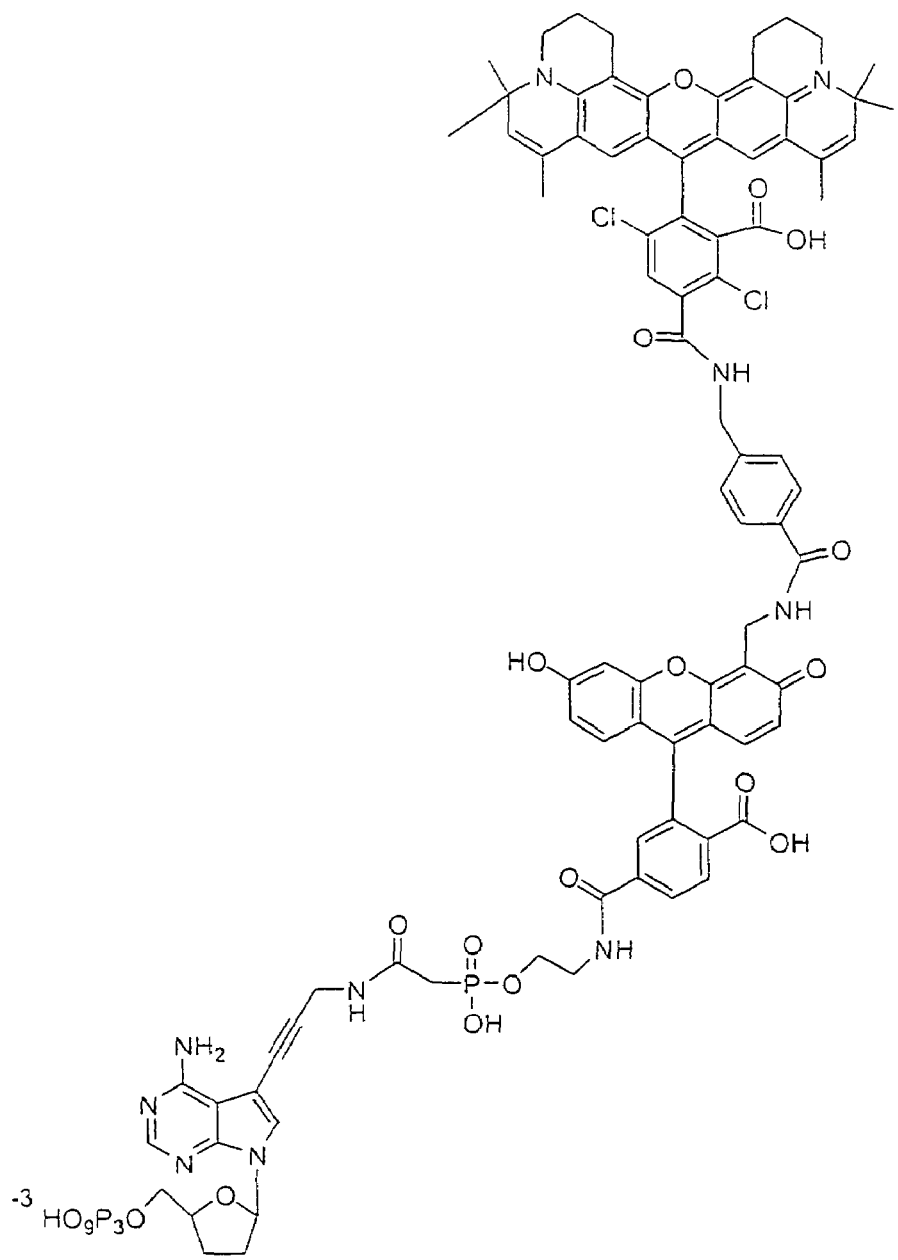
Figure 18A:
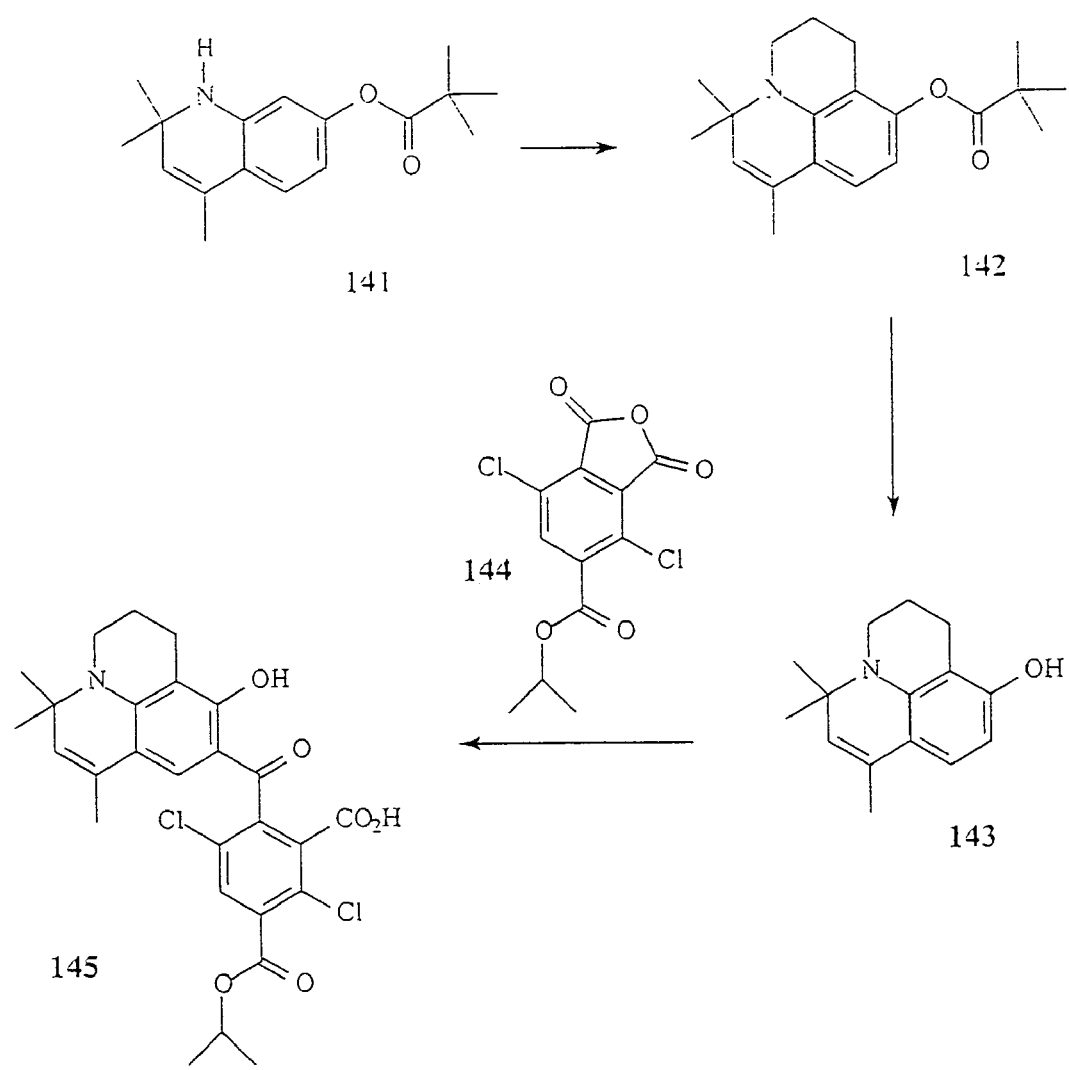
Figure 18B:
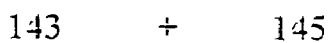
Figure 18B:
Figure 18B:
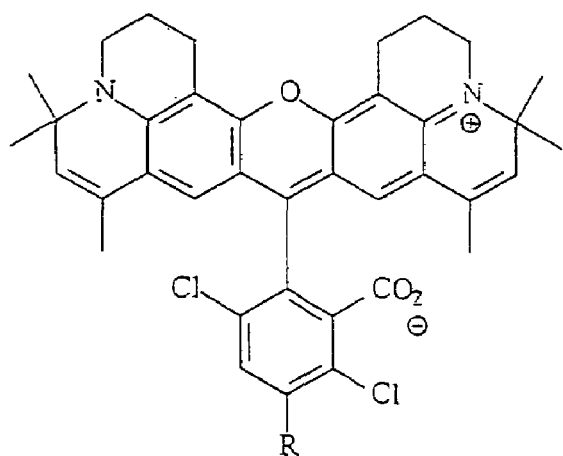
Figure 18B:
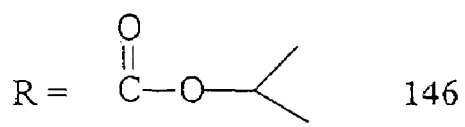
Figure 18B:
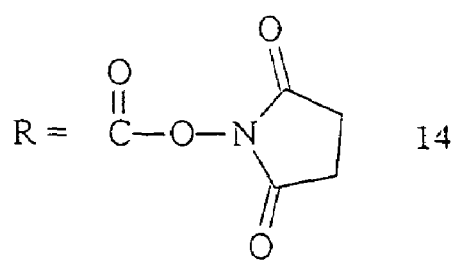

The present invention is directed to novel dye compounds and dye conjugates that have various advantageous properties. The invention has general application in the areas of fluorescent nucleic acid analysis, e.g., automated DNA or RNA sequencing, fragment analysis, detection of nucleic acid amplification products, detection of probe hybridization in hybridization arrays, diagnostic tests, and the like. In one aspect, the invention provides polynucleotides having more consistent size-dependent electrophoretic mobilities, such that sequence-dependent anomalies are reduced or eliminated. The invention finds application in automated sequencing methods which rely on uniform, size-dependent electrophoretic mobilities to determine whether low peak signals should be included or discarded, and whether overlapping peaks represent fragments of the same length. The invention is also useful in sequencing methods that involve the formation of 3' dye-labeled sequencing fragments. In addition, the invention can be used in polynucleotide detection and identification methods that rely on absolute or relative migration times or migration distances for polynucleotide identification.

I. Definitions

Unless stated otherwise, the following terms and phrases used herein are intended to have the following meanings:

"Alkyl" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. In preferred embodiments, the alkyl groups are ($C_1$-$C_6$) alkyl.

"Alkanyl" refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butyanyls such as butan-1-yl, butan-2-yl (sec-butyl), 2-methyl-propan-1-yl (isobutyl), 2-methyl-propan-2-yl (t-butyl), cyclobutan-1-yl, etc.; and the like. In preferred embodiments, the alkanyl groups are ($C_1$-$C_6$) alkanyl.

"Alkenyl" refers to an unsaturated branched, straight-chain or cyclic alkyl radical having at least one carbon-carbon double bond derived by the removal of one hydrogen atom from a single carbon atom of a parent alkene. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In preferred embodiments, the alkenyl group is ($C_2$-$C_6$) alkenyl.

"Alkynyl" refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. In preferred embodiments, the alkynyl group is ($C_2$-$C_6$) alkynyl.

"Alkyldiyl" refers to a saturated or unsaturated, branched, straight-chain or cyclic divalent hydrocarbon radical derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyls include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. In preferred embodiments, the alkyldiyl group is ($C_1$-$C_6$) alkyldiyl. Also preferred are saturated acyclic alkanyldiyl radicals in which the radical centers are at the terminal carbons, e.g., methandiyl (methano); ethan-1,2-diyl (ethano); propan-1,3-diyl (propano); butan-1,4-diyl (butano); and the like (also referred to as alkylenos, defined infra).

"Alkyleno" refers to a straight-chain alkyldiyl radical having two terminal monovalent radical centers derived by the removal of one hydrogen atom from each of the two terminal carbon atoms of straight-chain parent alkane, alkene or alkyne. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, but[1,3]diyno, etc.; and the like. Where specific levels of saturation are intended, the nomenclature alkano, alkeno and/or alkyno is used. In preferred embodiments, the alkyleno group is ($C_1$-$C_6$) alkyleno.

"Heteroalkyl, Heteroalkanyl, Heteroalkenyl, Heteroalkanyl, Heteroalkyldiyl and Heteroalkyleno" refer to alkyl, alkanyl, alkenyl, alkynyl, alkyldiyl and alkyleno radicals, respectively, in which one or more of the carbon atoms are each independently replaced with the same or different heteroatomic groups. Typical heteroatomic groups which can be included in these radicals include, but are not limited to, —O—, —S—, —O—O—, —S—S—, —O—S—, —NR'—, =N—N=, —N=N—, —N(O)N—, —N=N—NR'—, —PH—, —P(O)$_2$—, —O—P(O)$_2$—, —SH$_2$—, —S(O)$_2$—, —SnH$_2$— an the like, where each R' is independently hydrogen, alkyl, alkanyl, alkenyl, alkynyl, aryl, arylaryl, arylalkyl, heteroaryl, heteroarylalkyl or heteroaryl-heteroaryl as defined herein.

"Acyclic Heteroatomic Bridge" refers to a divalent bridge in which the backbone atoms are exclusively heteroatoms. Typical acyclic heteroatomic bridges include, but are not limited to, any of the various heteroatomic groups listed above, either alone or in combinations.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Aryl" refers to a monovalent aromatic hydrocarbon radical derived by the removal of one hydrogen atom from a single carbon atom of a parent aromatic ring system. Typical aryl groups include, but are not limited to, radicals derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In preferred embodiments, the aryl group is ($C_5$-$C_{14}$) aryl, with ($C_5$-$C_{10}$) being even more preferred. Particularly preferred aryls are phenyl and naphthyl.

"Aryldiyl" refers to a divalent aromatic hydrocarbon radical derived by the removal of one hydrogen atom from each of two different carbon atoms of a parent aromatic ring system or by the removal of two hydrogen atoms from a single carbon atom of a parent aromatic ring system. The two monovalent radical centers or each valency of the divalent center can form bonds with the same or different atom(s). Typical aryldiyl groups include, but are not limited to, divalent radicals derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In preferred embodiments, the aryldiyl group is ($C_5$-$C_{14}$) aryldiyl, with ($C_5$-$C_{10}$) being even more preferred. The most preferred aryldiyl groups are divalent radicals derived from benzene and naphthalene, especially phena-1,4-diyl, naphtha-2,6-diyl and naphtha-2,7-diyl.

"Aryleno" refers to a divalent bridge radical having two adjacent monovalent radical centers derived by the removal of one hydrogen atom from each of two adjacent carbon atoms of a parent aromatic ring system. Attaching an aryleno bridge radical, e.g. benzeno, to a parent aromatic ring system, e.g. benzene, results in a fused aromatic ring system, e.g. naphthalene. The bridge is assumed to have the maximum number of non-cumulative double bonds consistent with its attachment to the resultant fused ring system. In order to avoid double-counting carbon atoms, when an aryleno substituent is formed by taking together two adjacent substituents on a structure that includes alternative substituents, the carbon atoms of the aryleno bridge replace the bridging carbon atoms of the structure. As an example, consider the following structure

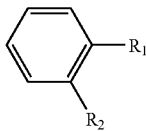

Wherein $R^1$, when taken alone is hydrogen, or when taken together with $R^2$ is ($C_5$-$C_{14}$) aryleno; and $R^2$, when taken alone is hydrogen, or when taken together with $R^1$ is ($C_5$-$C_{14}$) aryleno.

When $R^1$ and $R^2$ are each hydrogen, the resultant compound is benzene. When $R^1$ taken together with $R^2$ is $C_6$ aryleno (benzeno), the resultant compound is naphthalene. When $R^1$ taken together with $R^2$ is $C_{10}$ aryleno (naphthaleno), the resultant compound is anthracene or phenanthrene. Typical aryleno groups include, but are not limited to, aceanthryleno, acenaphthyleno, acephenanthryleno, anthraceno, azuleno, benzeno (benzo), chryseno, coroneno, fluorantheno, fluoreno, hexaceno, hexapheno, hexaleno, as-indaceno, s-indaceno, indeno, naphthaleno (naphtho), octaceno, octapheno, octaleno, ovaleno, penta-2,4-dieno, pentaceno, pentaleno, pentapheno, peryleno, phenaleno, phenanthreno, piceno, pleiadeno, pyreno, pyranthreno, rubiceno, triphenyleno, trinaphthaleno, and the like. Where a specific connectivity is intended, the involved bridging carbon atoms (of the aryleno bridge) are denoted in brackets, e.g., [1,2]benzeno ([1,2]benzo), [1,2]naphthaleno, [2,3]naphthaleno, etc. Thus, in the above example, when $R^1$ taken together with $R^2$ is [2,3]naphthaleno, the resultant compound is anthracene. When $R^1$ taken together with $R^2$ is [1,2]naphthaleno, the resultant compound is phenanthrene. In a preferred embodiment, the aryleno group is ($C_5$-$C_{14}$), with ($C_5$-$C_{10}$) being even more preferred.

"Arylaryl" refers to a monovalent hydrocarbon radical derived by the removal of one hydrogen atom from a single carbon atom of a ring system in which two or more identical or non-identical parent aromatic ring systems are joined directly together by a single bond, where the number of such direct ring junctions is one less than the number of parent aromatic ring systems involved. Typical arylaryl groups include, but are not limited to, biphenyl, triphenyl, phenylnaphthyl, binaphthyl, biphenyl-naphthyl, and the like. When the number of carbon atoms comprising an arylaryl group is specified, the numbers refer to the carbon atoms comprising each parent aromatic ring. For example, ($C_5$-$C_{14}$) arylaryl is an arylaryl group in which each aromatic ring comprises from 5 to 14 carbons, e.g., biphenyl, triphenyl, binaphthyl, phenylnaphthyl, etc. Preferably, each parent aromatic ring system of an arylaryl group is independently a ($C_5$-$C_{14}$) aromatic, more preferably a ($C_5$-$C_{10}$) aromatic. Also preferred are arylaryl groups in which all of the parent aromatic ring systems are identical, e.g., biphenyl, triphenyl, binaphthyl, trinaphthyl, etc.

"Biaryl" refers to an arylaryl radical having two identical parent aromatic systems joined directly together by a single bond. Typical biaryl groups include, but are not limited to, biphenyl, binaphthyl, bianthracyl, and the like. Preferably, the aromatic ring systems are ($C_5$-$C_{14}$) aromatic rings, more preferably ($C_5$-$C_{10}$) aromatic rings. A particularly preferred biaryl group is biphenyl.

"Arylalkyl" refers to an acyclic alkyl radical in which one of the hydrogen atoms bonded to a carbon atom, typically a terminal or sp³ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. In preferred embodiments, the arylalkyl group is ($C_6$-$C_{20}$) arylalkyl, e.g., the alkanyl, alkenyl or alkynyl moiety of the arylalkyl group is ($C_1$-$C_6$) and the aryl moiety is ($C_5$-$C_{14}$). In particularly preferred embodiments the arylalkyl group is ($C_6$-$C_{13}$), e.g., the alkanyl, alkenyl or alkynyl moiety of the arylalkyl group is ($C_1$-$C_3$) and the aryl moiety is ($C_5$-$C_{10}$).

"Parent Heteroaromatic Ring System" refers to a parent aromatic ring system in which one or more carbon atoms (and any necessary associated hydrogen atoms) are each independently replaced with the same or different heteroatom. Typical heteratoms to replace the carbon atoms include, but are not limited to, N, P, O, S, Si, etc. Specifically included within the definition of "parent heteroaromatic ring systems" are fused ring systems in which one or more rings are aromatic and one or more of the rings are saturated or unsaturated, such as, for example, arsindole, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl" refers to a monovalent heteroaromatic radical derived by the removal of one hydrogen atom from a single atom of a parent heteroaromatic ring system. Typical heteroaryl groups include, but are not limited to, radicals derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In preferred embodiments, the heteroaryl group is a 5-14 membered heteroaryl, with 5-10 membered heteroaryl being particularly preferred. The most preferred heteroaryl radicals are those derived from parent heteroaromatic ring systems in which any ring heteroatoms are nitrogens, such as imidazole, indole, indazole, isoindole, naphthyridine, pteridine, isoquinoline, phthalazine, purine, pyrazole, pyrazine, pyridazine, pyridine, pyrrole, quinazoline, quinoline, etc.

"Heteroaryldiyl" refers to a divalent heteroaromatic radical derived by the removal of one hydrogen atom from each of two different atoms of a parent heteroaromatic ring system or by the removal of two hydrogen atoms from a single atom of a parent heteroaromatic ring system. The two monovalent radical centers or each valency of the single divalent center can form bonds with the same or different atom(s). Typical heteroaryldiyl groups include, but are not limited to, divalent radicals derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In preferred embodiments, the heteroaryldiyl group is 5-14 membered heteroaryldiyl, with 5-10 membered being particularly preferred. The most preferred heteroaryldiyl groups are divalent radicals derived from parent heteroaromatic ring systems in which any ring heteroatoms are nitrogens, such as imidazole, indole, indazole, isoindole, naphthyridine, pteridine, isoquinoline, phthalazine, purine, pyrazole, pyrazine, pyridazine, pyridine, pyrrole, quinazoline, quinoline, etc.

"Heteroaryleno" refers to a divalent bridge radical having two adjacent monovalent radical centers derived by the removal of one hydrogen atom from each of two adjacent atoms of a parent heteroaromatic ring system. Attaching a heteroaryleno bridge radical, e.g. pyridino, to a parent aromatic ring system, e.g. benzene, results in a fused heteroaromatic ring system, e.g., quinoline. The bridge is assumed to have the maximum number of non-cumulative double bonds consistent with its attachment to the resultant fused ring system. In order to avoid double-counting ring atoms, when a heteroaryleno substituent is formed by taking together two adjacent substituents on a structure that includes alternative substituents, the ring atoms of the heteroaryleno bridge replace the bridging ring atoms of the structure. As an example, consider the following structure

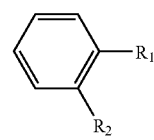

wherein $R^1$, when taken alone is hydrogen, or when taken together with $R^2$ is 5-14 membered heteroaryleno; and $R^2$, when taken alone is hydrogen, or when taken together with $R^1$ is 5-14 membered heteroaryleno.

When $R^1$ and $R^2$ are each hydrogen, the resultant compound is benzene. When $R^1$ taken together with $R^2$ is a 6-membered heteroaryleno (e.g., pyridino), the resultant compound is isoquinoline, quinoline or quinolizine. When $R^1$ taken together with $R^2$ is a 10-membered heteroaryleno (e.g., isoquinolino), the resultant compound is, e.g., acridine or phenanthridine. Typical heteroaryleno groups include, but are not limited to, acridino, carbazolo, β-carbolino, chromeno, cinnolino, furano, imidazolo, indazoleno, indoleno, indolizino, isobenzofurano, isochromeno, isoindoleno, isoquinolino, isothiazoleno, isoxazoleno, naphthyridino, oxadiazoleno, oxazoleno, perimidino, phenanthridino, phenanthrolino, phenazino, phthalazino, pteridino, purino, pyrano, pyrazino, pyrazoleno, pyridazino, pyridino, pyrimidino, pyrroleno, pyrrolizino, quinazolino, quinolino, quinolizino, quinoxalino, tetrazoleno, thiadiazoleno, thiazoleno, thiopheno, triazoleno, xantheno, and the like. Where a specific connectivity is intended, the involved bridging atoms (of the heteroaryleno bridge) are denoted in brackets, e.g., [1,2]pyridino, [2,3]pyridino, [3,4]pyridino, etc. Thus, in the above example, when $R^1$ taken together with $R^2$ is [1,2]pyridino, the resultant compound is quinolizine. When $R^1$ taken together with $R^2$ is [2,3]pyridino, the resultant compound is quinoline. When $R^1$ taken together with $R^2$ is [3,4]pyridino, the resultant compound is isoquinoline. In preferred embodiments, the heteroaryleno group is 5-14 membered heteroaryleno, with 5-10 membered being even more preferred. The most preferred heteroaryleno radicals are those derived from parent heteroaromatic ring systems in which any ring heteroatoms are nitrogens, such as imidazolo, indolo, indazolo, isoindolo, naphthyridino, pteridino, isoquinolino, phthalazino, purino, pyrazolo, pyrazino, pyridazino, pyridino, pyrrolo, quinazolino, quinolino, etc.

"Heteroaryl-Heteroaryl" refers to a monovalent heteroaromatic radical derived by the removal of one hydrogen atom from a single atom of a ring system in which two or more identical or non-identical parent heteroaromatic ring systems are joined directly together by a single bond, where the number of such direct ring junctions is one less than the number of parent heteroaromatic ring systems involved. Typical heteroaryl-heteroaryl groups include, but are not limited to, bipyridyl, tripyridyl, pyridylpurinyl, bipurinyl, etc. When the number of ring atoms are specified, the numbers refer to the number of atoms comprising each parent heteroatomic ring systems. For example, 5-14 membered heteroaryl-heteroaryl is a heteroaryl-heteroaryl group in which each parent heteroaromatic ring system comprises from 5 to 14 atoms, e.g., bipyridyl, tripyridyl, etc. Preferably, each parent heteroaromatic ring system is independently a 5-14 membered heteroaromatic, more preferably a 5-10 membered heteroaromatic. Also preferred are heteroaryl-heteroaryl groups in which all of the parent heteroaromatic ring systems are identical. The most preferred heteroaryl-heteroaryl radicals are those in which each heteroaryl group is derived from parent heteroaromatic ring systems in which any ring heteroatoms are nitrogens, such as imidazole, indole, indazole, isoindole, naphthyridine, pteridine, isoquinoline, phthalazine, purine, pyrazole, pyrazine, pyridazine, pyridine, pyrrole, quinazoline, quinoline, etc.

"Biheteroaryl" refers to a heteroaryl-heteroaryl radical having two identical parent heteroaromatic ring systems joined directly together by a single bond. Typical biheteroaryl groups include, but are not limited to, bipyridyl, bipurinyl, biquinolinyl, and the like. Preferably, the heteroaromatic ring systems are 5-14 membered heteroaromatic rings, more preferably 5-10 membered heteroaromatic rings. The most preferred biheteroaryl radicals are those in which the heteroaryl groups are derived from a parent heteroaromatic ring system in which any ring heteroatoms are nitrogens, such as biimidazolyl, biindolyl, biindazolyl, biisoindolyl, binaphthyridinyl, bipteridinyl, biisoquinolinyl, biphthalazinyl, bipurinyl, bipyrazolyl, bipyrazinyl, bipyridazinyl, bipyridinyl, bipyrrolyl, biquinazolinyl, biquinolinyl, etc.

"Heteroarylalkyl" refers to an acyclic alkyl radical in which one of the hydrogen atoms bonded to a carbon atom, typically a terminal or $sp^3$ carbon atom, is replaced with a heteroaryl radical. Where specific alkyl moieties are intended, the nomenclature heteroarylalkanyl, heteroarylakenyl and/or heterorylalkynyl is used. In preferred embodiments, the heteroarylalkyl group is a 6-20 membered heteroarylalkyl, e.g., the alkanyl, alkenyl or alkynyl moiety of the heteroarylalkyl is 1-6 membered and the heteroaryl moiety is a 5-14-membered heteroaryl. In particularly preferred embodiments, the heteroarylalkyl is a 6-13 membered heteroarylalkyl, e.g., the alkanyl, alkenyl or alkynyl moiety is 1-3 membered and the heteroaryl moiety is a 5-10 membered heteroaryl.

"Substituted" refers to a radical in which one or more hydrogen atoms are each independently replaced with the same or different substituent(s). Typical substituents include, but are not limited to, —X, —R, —O⁻, =O, —OR, —SR, —S⁻, =S, —NRR, =NR, perhalo ($C_1$-$C_6$) alkyl, —$CX_3$, —$CF_3$, —CN, —OCN, —SCN, —NCO, —NCS, —NO, —$NO_2$, =$N_2$, —$N_3$, —S(O)$_2$O⁻, —S(O)$_2$OH, —S(O)$_2$R, —C(O)R, —C(O)X, —C(S)R, —C(S)X, —C(O)OR, —C(O)O⁻, —C(S)OR, —C(O)SR, —C(S)SR, —C(O)NRR, —C(S)NRR and —(NR)NRR, where each X is independently a halogen (preferably —F or —Cl) and each R is independently hydrogen, alkyl, alkanyl, alkenyl, alkynyl, aryl, arylalkyl, arylaryl, heteroaryl, heteroarylalkyl or heteroaryl-heteroaryl, carboxyl, acetyl, sulfonyl, sulfinyl, sulfone, phosphate, or phosphonate, as defined herein. The actual substituent substituting any particular group will depend upon the identity of the group being substituted.

"Nucleobase" means a nitrogen-containing heterocyclic moiety capable of forming Watson-Crick type hydrogen bonds with a complementary nucleobase or nucleobase analog, e.g. a purine, a 7-deazapurine, or a pyrimidine. Typical nucleobases are the naturally occurring nucleobases adenine, guanine, cytosine, uracil, thymine, and analogs of naturally occurring nucleobases, e.g. 7-deazaadenine, 7-deaza-8-azaadenine, 7-deazaguanine, 7-deaza-8-azaguanine, inosine, nebularine, nitropyrrole, nitroindole, 2-amino-purine, 2,6-diamino-purine, hypoxanthine, pseudouridine, pseudocytidine, pseudoisocytidine, 5-propynyl-cytidine, isocytidine, isoguanine, 2-thiopyrimidine, 6-thioguanine, 4-thiothymine, 4-thiouracil, $O^6$-methylguanine, $N^6$-methyl-adenine, $O^4$-methylthymine, 5,6-dihydrothymine, 5,6-dihydrouracil, 4-methylindole, and ethenoadenine (Fasman, *Practical Handbook of Biochemistry and Molecular Biology*, pp. 385-394, CRC Press, Boca Raton, Fla. (1989)).

"Nucleoside" means a compound comprising a nucleobase linked to a C-1' carbon of a ribose sugar or analog thereof. The ribose or analog may be substituted or unsubstituted. Substituted ribose sugars include, but are not limited to, those riboses in which one or more of the carbon atoms, preferably the 3'-carbon atom, is substituted with one or more of the same or different substituents such as —R, —OR, —NRR or halogen (e.g., fluoro, chloro, bromo, or iodo), where each R group is independently —H, $C_1$-$C_6$ alkyl or $C_3$-$C_{14}$ aryl. Particularly preferred riboses are ribose, 2'-deoxyribose, 2',3'-dideoxyribose, 3'-haloribose (such as 3'-fluororibose or 3'-chlororibose) and 3'-alkylribose. Typically, when the nucleobase is A or G, the ribose sugar is attached to the $N^9$-position of the nucleobase. When the nucleobase is C, T or U, the pentose sugar is attached to the $N^1$-position of the nucleobase (Kornberg and Baker, *DNA Replication*, $2^{nd}$ Ed., Freeman, San Francisco, Calif., (1992)). Examples of ribose analogs include arabinose, 2'-O-methyl ribose, and locked nucleoside analogs (e.g., WO 99/14226), for example, although many other analogs are also known in the art.

"Nucleotide" means a phosphate ester of a nucleoside, either as an independent monomer or as a subunit within a polynucleotide. Nucleotide triphosphates are sometimes denoted as "NTP", "dNTP" (2'-deoxypentose) or "ddNTP" (2',3'-dideoxypentose) to particularly point out the structural features of the ribose sugar. "Nucleotide 5'-triphosphate" refers to a nucleotide with a triphosphate ester group at the 5' position. The triphosphate ester group may include sulfur substitutions for one or more phosphate oxygen atoms, e.g. α-thionucleotide 5'-triphosphates.

"Polynucleotide" and "oligonucleotide", which are used interchangeably herein, refer to linear polymers of natural nucleotide monomers or analogs thereof, including for example, double- and single-stranded deoxyribonucleotides, ribonucleotides, α-anomeric forms thereof, and the like. A polynucleotide may be composed entirely of deoxyribonucleotides, ribonucleotides, or analogs thereof, or may contain blocks or mixtures of two or more different monomer types. Usually nucleoside monomers are linked by phosphodiester linkages. However, polynucleotides and oligonucleotides containing non-phosphodiester linkages are also contemplated. "Polynucleotide" and "oligonucleotide" also encompass polymers that contain one or more non-naturally occurring monomers and/or intersubunit linkages, such as peptide nucleic acids (PNAs, e.g., polymers comprising a backbone of amide-linked N-(2-aminoethyl)-glycine subunits to which nucleobases are attached via the non-amide backbone nitrogens. See Nielsen et al., Science 254:1497-1500 (1991)). Polynucleotides typically range in size from a few monomeric units, e.g. 8-40, to several thousand monomeric units. Whenever a polynucleotide is represented by a sequence of letters, such as "ATGCCTG," it will be understood that the nucleotides are in 5'->3' order from left to right and that "A" denotes deoxyadenosine, "C" denotes deoxycytidine, "G" denotes deoxyguanosine, and "T" denotes thymidine, unless otherwise noted.

"Nucleotide subunit" or "polynucleotide subunit" refers to a single nucleotide or nucleotide analog within a polynucleotide or polynucleotide analog.

"Phosphate analog" refers to an analog of phosphate wherein one or more of the oxygen atoms is replaced with a non-oxygen moiety. Exemplary phosphate analogs including phosphorothioate, phosphorodithioate, phosphoroselenoate, phosphorodiselenoate, phosphoro-anilothioate, phosphotriester, phosphoranilidate, phosphoramidate, alkylphosphonates such as methylphosphonates, boronophosphates.

"Linker" refers to a moiety that links a dye to a substrate such as an oligonucleotide, or links one dye to another dye (e.g., links a donor to an acceptor dye).

"Enzymatically incorporatable" means that a nucleotide is capable of being enzymatically incorporated onto the terminus, e.g. 3' terminus, of a polynucleotide chain, or internally through nick-translation of a polynucleotide chain, through action of a template-dependent or template-independent polymerase enzyme. A nucleotide-5'-triphosphate is an example of an enzymatically incorporatable nucleotide.

"Enzymatically extendable" or "3' extendable" means a nucleotide or polynucleotide that is capable of being appended to a nucleotide or polynucleotide by enzyme action. A polynucleotide containing a 3' hydroxyl group is an example of an enzymatically extendable polynucleotide.

"Terminator" means an enzymatically incorporatable nucleotide which prevents subsequent incorporation of nucleotides to the resulting polynucleotide chain and thereby halts polymerase-mediated extension. Typical terminators lack a 3'-hydroxyl substituent and include 2',3'-dideoxyribose, 2',3'-didehydroribose, and 2',3'-dideoxy-3'-haloribose, e.g. 3'-deoxy-3'-fluoro-ribose or 2',3'-dideoxy-3'-fluororibose, for example. Alternatively, a ribofuranose analog can be used, such as 2',3'-dideoxy-β-D-ribofuranosyl, β-D-arabinofuranosyl, 3'-deoxy-β-D-arabinofuranosyl, 3'-amino-2',3'-dideoxy-β-D-ribofuranosyl, and 2',3'-dideoxy-3'-fluoro-β-D-ribofuranosyl (see, for example, Chidgeavadze et al., Nucleic Acids Res., 12: 1671-1686 (1984), and Chidgeavadze et al. FEB. Lett., 183: 275-278 (1985)). Nucleotide terminators also include reversible nucleotide terminators (Metzker et al. Nucleic Acids Res., 22(20):4259 (1994)).

"Nonextendable" or "3' nonextendable" refers to the fact that a terminator is incapable, or substantially incapable, of being extended in the 3' direction by a template-dependent DNA or RNA polymerase.

"Spectrally resolvable" means that two or more dyes have emission bands that are sufficiently distinct, i.e., sufficiently non-overlapping, that they can be distinguished on the basis of a unique fluorescent signal generated by each dye.

Generally, whenever a compound mentioned in this disclosure contains a positive or negative charge, it should be understood that such compound may also be accompanied by a suitable counterion that balances the positive or negative charge. Exemplary positively charged counterions include, without limitation, $H^+$, $NH_4^+$, $Na^+$, $K^+$, $Mg^{2+}$, trialkylammonium (such as triethylammonium), tetraalkylammonium (such as tetraethylammonium), and the like. Exemplary negatively charged counterions include, without limitation, carbonate, bicarbonate, acetate, chloride, and phosphate, for example. Also, although particular resonance structures may be shown herein, such structures are intended to include all other possible resonance structures.

II. Conjugates

In one aspect, the present invention provides compositions that comprise at least one dye-labeled nucleobase of the type described herein. Such compositions include not only nucleobase-dye conjugates as independent molecules, but also as nucleosides, nucleotides and polynucleotides containing such conjugates.

In one embodiment, a dye-labeled nucleobase of the invention has the form B-L-D, wherein B is a nucleobase, L is an anionic linker, and D is a fluorescent dye.

Nucleobase B may be any moiety capable of forming Watson-Crick hydrogen bonds with a complementary nucleobase or nucleobase analog, as set forth in the Definition section above. Typically, B is a nitrogen-containing heterocyclic moiety such as a 7-deazapurine, purine, or pyrimidine nucleotide base. In certain embodiments, B is uracil, cytosine, 7-deazaadenine, or 7-deazaguanosine. When B is a purine, the linker is usually attached to the 8-position of the purine. When B is a 7-deazapurine, the linker to the dye is usually attached to the 7-position of the 7-deazapurine. When B is pyrimidine, the linker is usually attached to the 5-position of the pyrimidine.

Fluorescent dye D may be any fluorescent dye which is suitable for the purposes of the invention. Typically, the fluorescent dye comprises a resonance-delocalized system or aromatic ring system that absorbs light at a first wavelength and emits fluorescent light at a second wavelength in response to the absorption event. A wide variety of such dye molecules are known in the art. For example, fluorescent dyes can be selected from any of a variety of classes of fluorescent compounds, such as xanthenes, rhodamines, fluoresceins, cyanines, phthalocyanines, squaraines, and bodipy dyes.

In one embodiment, the dye is a xanthene-type dye, which contains a fused three-ring system of the form:

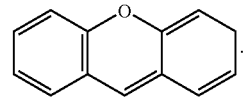

This parent xanthene ring may be unsubstituted (i.e., all substituents are H) or may be substituted with one or more of a variety of the same or different substituents, such as described below.

In one embodiment, the dye contains a parent xanthene ring having the general structure:

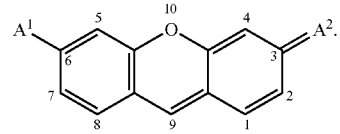

In the parent xanthene ring depicted above, $A^1$ is OH or $NH_2$ and $A^2$ is O or $NH_2^+$. When $A^1$ is OH and $A^2$ is O, the parent xanthene ring is a fluorescein-type xanthene ring. When $A^1$ is $NH_2$ and $A^2$ is $NH_2^+$, the parent xanthene ring is a rhodamine-type xanthene ring. When $A^1$ is $NH_2$ and $A^2$ is O, the parent xanthene ring is a rhodol-type xanthene ring. In the parent xanthene ring depicted above, one or both nitrogens of $A^1$ and $A^2$ (when present) and/or one or more of the carbon atoms at positions C1, C2, C4, C5, C7, C8 and C9 can be independently substituted with a wide variety of the same or different substituents. In one embodiment, typical substituents include, but are not limited to, —X, —R, —OR, —SR, —NRR, perhalo ($C_1$-$C_6$) alkyl, —$CX_3$, —$CF_3$, —CN, —OCN, —SCN, —NCO, —NCS, —NO, —$NO_2$, —$N_3$, —$S(O)_2O^-$, —$S(O)_2OH$, —$S(O)_2R$, —C(O)R, —C(O)X, —C(S)R, —C(S)X, —C(O)OR, —$C(O)O^-$, —C(S)OR, —C(O)SR, —C(S)SR, —C(O)NRR, —C(S)NRR and —C(NR)NRR, where each X is independently a halogen (preferably —F or Cl) and each R is independently hydrogen, ($C_1$-$C_6$) alkyl, ($C_1$-$C_6$) alkanyl, ($C_1$-$C_6$) alkenyl, ($C_1$-$C_6$) alkynyl, ($C_5$-$C_{20}$) aryl, ($C_6$-$C_{26}$) arylalkyl, ($C_5$-$C_{20}$) arylaryl, heteroaryl, 6-26 membered heteroarylalkyl 5-20 membered heteroaryl-heteroaryl, carboxyl, acetyl, sulfonyl, sulfinyl, sulfone, phosphate, or phosphonate. Moreover, the C1 and C2 substituents and/or the C7 and C8 substituents can be taken together to form substituted or unsubstituted buta[1,3]dieno or ($C_5$-$C_{20}$) aryleno bridges. Generally, substituents which do not tend to quench the fluorescence of the parent xanthene ring are preferred, but in some embodiments quenching substituents may be desirable. Substituents that tend to quench fluorescence of parent xanthene rings are electron-withdrawing groups, such as —$NO_2$, —Br, and —I. In one embodiment, C9 is unsubstituted. In another embodiment, C9 is substituted with a phenyl group. In another embodiment, C9 is substituted with a substituent other than phenyl.

When $A^1$ is $NH_2$ and/or $A^2$ is $NH_2^+$, these nitrogens can be included in one or more bridges involving the same nitrogen atom or adjacent carbon atoms, e.g., ($C_1$-$C_{12}$) alkyldiyl, ($C_1$-$C_{12}$) alkyleno, 2-12 membered heteroalkyldiyl and/or 2-12 membered heteroalkyleno bridges.

Any of the substituents on carbons C1, C2, C4, C5, C7, C8, C9 and/or nitrogen atoms at C3 and/or C6 (when present) can be further substituted with one or more of the same or different substituents, which are typically selected from —X, —R', =O, —OR', —SR', =S, —NR'R', =NR', —$CX_3$, —CN, —OCN, —SCN, —NCO, —NCS, —NO, —$NO_2$, =$N_2$, —$N_3$, —NHOH, —$S(O)_2O^-$, —$S(O)_2OH$, —$S(O)_2R'$, —$P(O)(O^-)_2$, —$P(O)(OH)_2$, —C(O)R', —C(O)X, —C(S)R', —C(S)X, —C(O)OR', —$C(O)O^-$, —C(S)OR', —C(O)SR', —C(S)SR', —C(O)NR'R', —C(S)NR'R' and —C(NR)NR'R', where each X is independently a halogen (preferably —F or —Cl) and each R' is independently hydrogen, ($C_1$-$C_6$) alkyl, 2-6 membered heteroalkyl, ($C_5$-$C_{14}$) aryl or heteroaryl, carboxyl, acetyl, sulfonyl, sulfinyl, sulfone, phosphate, or phosphonate.

Exemplary parent xanthene rings include, but are not limited to, rhodamine-type parent xanthene rings and fluorescein-type parent xanthene rings.

In one embodiment, the dye contains a rhodamine-type xanthene dye that includes the following ring system:

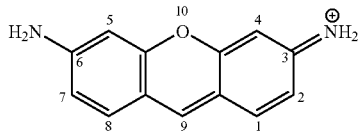

In the rhodamine-type xanthene ring depicted above, one or both nitrogens and/or one or more of the carbons at positions C1, C2, C4, C5, C7 or C8 can be independently substituted with a wide variety of the same or different substituents, as described above for the parent xanthene rings, for example. Exemplary rhodamine-type xanthene dyes include, but are not limited to, the xanthene rings of the rhodamine dyes described in U.S. Pat. Nos. 5,936,087, 5,750,409, 5,366,860, 5,231,191, 5,840,999, 5,847,162, and 6,080,852 (Lee et al.), PCT Publications WO 97/36960 and WO 99/27020, Sauer et al., J Fluorescence 5(3):247-261 (1995), Arden-Jacob, Neue Lanwellige Xanthen-Farbstoffe für Fluoreszenzsonden und Farbstoff Laser, Verlag Shaker, Germany (1993), and Lee et al., Nucl. Acids Res. 20:2471-2483 (1992). Also included within the definition of "rhodamine-type xanthene ring" are the extended-conjugation xanthene rings of the extended rhodamine dyes described in U.S. application Ser. No. 09/325,243 filed Jun. 3, 1999.

In another embodiment, the dye comprises a fluorescein-type parent xanthene ring having the structure:

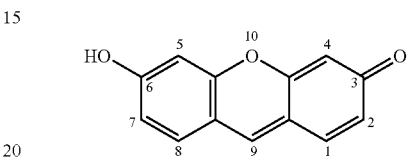

In the fluorescein-type parent xanthene ring depicted above, one or more of the carbons at positions C1, C2, C4, C5, C7, C8 and C9 can be independently substituted with a wide variety of the same or different substituents, as described above for the parent xanthene rings. Exemplary fluorescein-type parent xanthene rings include, but are not limited to, the xanthene rings of the fluorescein dyes described in U.S. Pat. Nos. 4,439,356, 4,481,136, 5,188,934, 5,654,442, and 5,840,999, WO 99/16832, and EP 050684. Also included within the definition of "fluorescein-type parent xanthene ring" are the extended xanthene rings of the fluorescein dyes described in U.S. Pat. Nos. 5,750,409 and 5,066,580.

In another embodiment, the dye comprises a rhodamine dye, which comprises a rhodamine-type xanthene ring in which the C9 carbon atom is substituted with an orthocarboxy phenyl substituent (pendent phenyl group). Such compounds are also referred to herein as orthocarboxyfluoresceins. A particularly preferred subset of rhodamine dyes are 4,7,-dichlororhodamines. Typical rhodamine dyes include, but are not limited to, rhodamine B, 5-carboxyrhodamine, rhodamine X (ROX), 4,7-dichlororhodamine X (dROX), rhodamine 6G (R6G), 4,7-dichlororhodamine 6G, rhodamine 110 (R110), 4,7-dichlororhodamine 110 (dR110), tetramethyl rhodamine (TAMRA) and 4,7-dichloro-tetramethyl-rhodamine (dTAMRA). Additional rhodamine dyes can be found, for example, in U.S. Pat. No. 5,366,860 (Bergot et al.), U.S. Pat. No. 5,847,162 (Lee et al.), U.S. Pat. No. 6,017,712 (Lee et al.), U.S. Pat. No. 6,025,505 (Lee et al.), U.S. Pat. No. 6,080,852 (Lee et al.), U.S. Pat. No. 5,936,087 (Benson et al.), U.S. Pat. No. 6,111,116 (Benson et al.), U.S. Pat. No. 6,051,719 (Benson et al.), U.S. Pat. Nos. 5,750,409, 5,366,860, 5,231,191, 5,840,999, and 5,847,162, U.S. application Ser. No. 09/325,243 filed Jun. 3, 1999, PCT Publications WO 97/36960 and WO 99/27020, Sauer et al., 1995, J. Fluorescence 5(3):247-261, Arden-Jacob, 1993, Neue Lanwellige Xanthen-Farbstoffe für Fluoresenzsonden und Farbstoff Laser, Verlag Shaker, Germany, and Lee et al., Nucl. Acids Res. 20(10):2471-2483 (1992), Lee et al., Nucl. Acids Res. 25:2816-2822 (1997), and Rosenblum et al., Nucl. Acids Res. 25:4500-4504 (1997), for example. In one embodiment, the dye is a 4,7-dichloro-orthocarboxyrhodamine.

In another embodiment, the dye comprises a fluorescein dye, which comprises a fluorescein-type xanthene ring in which the C9 carbon atom is substituted with an orthocarboxy phenyl substituent (pendent phenyl group). A preferred subset of fluorescein-type dyes are 4,7,-dichlorofluoresceins. Typical fluorescein dyes include, but are not limited to, 5-carboxyfluorescein (5-FAM), 6-carboxyfluorescein (6-FAM). Additional typical fluorescein dyes can be found, for example, in U.S. Pat. Nos. 5,750,409, 5,066,580, 4,439,356, 4,481,136, 5,188,934 (Menchen et al.), U.S. Pat. No. 5,654,442 (Menchen et al.), U.S. Pat. No. 6,008,379 (Benson et al.), and U.S. Pat. No. 5,840,999, PCT publication WO 99/16832, and EPO Publication 050684. In one embodiment, the dye is a 4,7-dichloro-orthocarboxyfluorescein.

In other embodiments, the dye can be a cyanine, phthalocyanine, squaraine, or bodipy dye, such as described in the following references and references cited therein: U.S. Pat. No. 5,863,727 (Lee et al.), U.S. Pat. No. 5,800,996 (Lee et al.), U.S. Pat. No. 5,945,526 (Lee et al.), U.S. Pat. No. 6,080,868 (Lee et al.), U.S. Pat. No. 5,436,134 (Haugland et al.), U.S. Pat. No. 5,863,753 (Haugland et al.), U.S. Pat. No. 6,005,113 (Wu et al.), and WO 96/04405 (Glazer et al.).

Sometimes, the designation -1 or -2 is placed after an abbreviation of a particular dye, e.g., HEX-1. The "-1" and "-2" designations indicate that a particular 5- or 6-carboxy dye isomer being used. The 1 and 2 isomers are defined by order of elution (the 1 isomer elutes before the 2 isomer) of free dye in a reverse-phase chromatographic separation system utilizing a C-8 column and an elution gradient of 15% acetonitrile/85% 0.1 $\underline{M}$ triethylammonium acetate to 35% acetonitrile/65% 0.1 $\underline{M}$ triethylammonium acetate.

Anionic linker L is designed to have an overall negative charge. Typically, this negative charge is provided by one or more negatively charged groups in the linker. If the anionic linker contains a positively charged group (e.g., bridging or nonbridging amino groups), then the linker must also contain a sufficient number of negatively charged groups to ensure that the total negative charge in the linker exceeds the total positive charge. In one embodiment, the linker contains no positively charged groups. The linker may contain one, two, or more net negative charges which may be provided by one, two, or more negatively charged groups. In one embodiment, the linker contains a single negative charge. In another specific embodiment, the linker contains two negative charges which may be provided by a single group or two groups. In specific embodiments, the overall charge of the linker at pH 9 can be at least -1, -2, -3, or greater. Preferably, the overall charge of the linker at pH 9 is at least -1. By way of non-limiting examples, such anionic groups include: phosphate monoester ($-OPO_3^{2-}$), phosphodiester of the form $-OP(=O)(O^-)O-$ (in which the phosphorus and two oxygen atoms are linker chain atoms), phosphodiester of the form $-OP(=O)(O^-)(OR)$ (in which R is a masking group such as alkyl, alkenyl, alkynyl, aryl, alkaryl, etc., and the left-most oxygen is bound directly or indirectly to the linker chain), phosphonate monoester of the form $-Y-P(=O)(O^-)O-$ (in which Y is an alkyl carbon, such as $CH_2$, an ethene carbon, an ethyne carbon, or a benzene ring carbon, and preferably $CH_2$), and Y, the phosphorus atom and the right-hand oxygen atom are linker chain atoms), phosphonate monoester of the form $-Y-P(=O)(O^-)(OR)$ or $-OP(=O)(O^-)(Z)$ (wherein Y is as just described, and R and Z are each masking groups as just defined for R, but none of the phosphonate monoester atoms are linker chain atoms), sulfate monoester ($-OSO_3^-$), sulfonic acid (sulfonate, $-SO_3^-$), and carboxylic acid (carboxylate, $-CO_2^-$). In addition, anionic groups can include groups with a $pK_a<10$, such as nitrophenolate, thiolate, phenylthiolate, fluorinated alkyl alcohol (e.g., perfluoro hydroxymethyl or perfluoro hydroxyethyl), sulfonimides, and squarates.

Anionic groups within a linker can be classified in various ways. First, anionic groups can be divided between bridging and non-bridging groups, depending on whether an anionic group is within the chain of linker atoms (a bridging anionic group) or is outside the chain of linker atoms (a non-bridging group). Examples of bridging anionic groups are phosphodiester of the form $-OP(=O)(O^-)O-$, and phosphonate monoester of the form $-CH_2P(=O)(O^-)O-$. Examples of non-bridging anionic groups are phosphate monoester ($-OPO_3^{2-}$), phosphodiester of the form $-OP(=O)(O^-)OR$ (where R is defined as above), phosphonic acid ($-PO_3^{2-}$), phosphonate monoester of the form $-CH_2P(=O)(O^-)(OR)$ or $-OP(=O)(O^-)(Z)$ (where R and Z are defined as above), sulfate monoester, sulfonic acid, and carboxylic acid. Accordingly, the invention contemplates linkers that contain one or more bridging anionic groups, one or more divalent anionic groups, and combinations thereof.

Anionic groups can also be classified by net formal charge. Examples of groups that provide a single negative charge at pH 9 include phosphodiester (both bridging and non-bridging), phosphonate monoester of the form $-CH_2P(=O)(O^-)O-$, $-CH_2P(=O)(O^-)(OR)$, and $-OP(=O)(O^-)(Z)$, sulfate monoester, sulfonic acid, and carboxylic acid. Examples of groups that provide a double negative charge at pH 9 include phosphate monoester (non-bridging) and phosphonic acid of the form ($-CH_2PO_3^{2-}$). Accordingly, the invention contemplates linkers that contain singly charged anionic groups, doubly charged anionic groups, and combinations thereof.

Any of a variety of anionic linkers can be used. Typically, a linker between B and D will have a linker chain length of from about 4 to about 30 linker chain atoms, and typically from 4 to 20 linker chain atoms, although shorter and longer linkers may also be used. Several exemplary anionic linkers are illustrated in the attached Figures and in the compounds prepared in the Examples below.

The junction between a nucleobase B and linker L can be located at any suitable position on the nucleobase. Preferably, the attachment site on the nucleobase is selected so as not to interfere with or eliminate the H-bonding capability of the nucleobase with respect to a complementary nucleobase. When B includes a purine nucleobase, the linker is usually attached to the N-8-position of the purine. When B includes a 7-deazapurine nucleobase, the linker is usually attached to the N-7-position of the 7-deazapurine. When B includes a pyrimidine base, the linkage is attached to the C-5-position of the pyrimidine. In a nucleoside, nucleotide, or polynucleotide subunit, a purine or 7-deazapurine is usually attached to a sugar moiety via the N-9-position of the purine or deazapurine, and a pyrimidine is usually attached to a sugar moiety via the N-1-position of the pyrimidine.

The particular entity by which a linker is connected to a nucleobase can be any chemical group that is suitable for the purposes of the present invention. A variety of suitable chemical groups are known. For example, the terminal chemical group in the linker that is covalently attached to the nucleobase can be an acetylene moiety ($-C\equiv C-$), and often is a propargyl moiety ($-C\equiv CCH_2-$), since such linkage moieties tend to be particularly compatible with a variety of polymerase enzymes used for primer extension. However, non-acetylenic chemical groups are also contemplated. Examples of suitable terminal groups for attachment to a nucleobase can be found in the following exemplary references:

TABLE 1

| | |
|---|---|
| Aminopropargyl | EPO Patent No. 251786B1 (Hobbs et al.) |
| | U.S. Pat. Nos. 5,151,507 and |
| | 5,047,519 (Hobbs et al.) |
| | Hobbs et al., J. Org. Chem., 54: 3420 |
| | (1989). |
| Oxypropargyl or | U.S. Pat. No. 5,821,356 (Khan et al.) |
| aminoethyloxypropargyl | U.S. Pat. No. 5,770,716 (Khan et al.) |
| | U.S. Pat. No. 5,936,087 (Benson et al.) |
| —(C≡C)$_n$—Ar$_o$—C≡C$_p$— | U.S. Pat. No. 5,948,648 (Khan et al.) |
| and variants thereof | U.S. Pat. No. 6,096,875 (Khan et al.) |
| Acylethenyl | U.S. Pat. No. 6,080,852 (Lee et al.) |
| —C≡C—C$_6$H$_4$— | U.S. Pat. No. 6,080,852 (Lee et al.) |
| Other | U.S. Pat. No. 6,008,379 (Benson et al.) |

The junction between linker L and dye moiety D can be located at any suitable position on the dye moiety, preferably so that the fluorescent properties of the dye are not adversely affected. For a xanthene-type ring, the linker can be joined to any available carbon atom, or to one of the nitrogen atoms in a rhodamine-type xanthene ring. For a rhodamine dye or fluorescein dye, the substituent positions on the pendent phenyl ring are also available, particularly the positions which are para to C9 of the xanthene ring (5 position), or para to the ortho carboxyl group (6 position). In addition, the particular chemical group by which a linker is connected to a nucleobase can be any chemical group that is suitable for the purposes of the present invention. A variety of chemical groups and points of attachment on various dyes can be found, for example, in U.S. Pat. Nos. 5,654,442 and 5,188,934 (Menchen et al.), U.S. Pat. No. 6,020,481 (Benson et al.), U.S. Pat. No. 5,800,996 (Lee et al.), U.S. Pat. No. 6,025,505 (Lee et al.), U.S. Pat. No. 5,821,356 (Khan et al.), U.S. Pat. No. 5,770,716 (Khan et al.), U.S. Pat. No. 6,088,379 (Benson et al.), U.S. Pat. No. 6,051,719 (Benson et al.), U.S. Pat. No. 6,096,875 (Khan et al.), U.S. Pat. No. 6,080,868 (Lee et al.), U.S. patent application Ser. No. 09/325,243 filed Jun. 3, 1999 (Lam et al.), Ser. No. 09/498,702 filed Feb. 7, 2000 (Upadhya et al.), Ser. No. 09/564,417 filed May 2, 2000 (Menchen et al.), and Ser. No. 09/433,093 filed Nov. 3, 1999 (Lee et al.). In one preferred embodiment, for xanthene derivatives that contain a C9 phenyl group, such as a rhodamine dye or fluorescein dye, the linker is attached to the dye via a 5-carboxyphenyl (para to the xanthene C9 carbon atom) or 6-carboxyphenyl group (meta to the xanthene C9 carbon atom). In another preferred embodiment, for xanthene dyes generally, the linker is preferably attached to a 4-carbon atom or 5-carbon atom on the xanthene ring. In a third preferred embodiment, for rhodamine-type xanthene dyes and rhodamine dyes, the linker is attached to the 3 or 6-nitrogen atom of the xanthene ring. Further guidance for forming conjugates of the invention can be found below with reference to the Examples herein.

The dye-labeled nucleobase of the invention may also have the form B-L1-D1-L2-D2, wherein B is a nucleobase, L1 and L2 are linkers such that at least one of L1 and L2 is an anionic linker, and D1 and D2 are members of a fluorescent donor/acceptor pair. In one embodiment, D1 is a donor dye, and D2 is an acceptor dye. In another embodiment, D2 is a donor dye, and D1 is an acceptor dye. For donor/acceptor pairs, it is understood that the donor dye and acceptor dye have different (non-identical) spectral properties. Thus, although the donor and acceptor may have the same type of aromatic ring structure (e.g., when both the donor and acceptor are fluorescein dyes, or both are rhodamine dyes), different spectral properties can arise for the donor and acceptor due to the nature of the substituents on each one. The donor dye is effective to enhance the intensity of fluorescence emission of the acceptor dye relative to the intensity that would be observed in the absence of the donor dye under the same conditions. Conjugates of this form may be referred to herein as "FRET probes", "FRET-labeled conjugates" or FRET-labeled nucleotides because upon excitation of the donor dye, the conjugate can undergo nonradiative fluorescence resonance energy transfer from the donor to the acceptor, such that the acceptor dye can then emit fluorescent light at a second wavelength in response thereto.

The donor dye and acceptor dye can be any fluorescent dye, and are each preferably fluorescent aromatic dyes. For example, the donor and acceptor dye, taken separately, can be a xanthene, rhodamine, dibenzorhodamine, fluorescein, [8,9] benzophenoxazine, cyanine, phthalocyanine, squaraine, or bodipy dye. Furthermore, the donor and acceptor dyes can be linked together using any of a variety of attachment sites on each dye. For example, if D1 is a fluorescein and D2 is a rhodamine (both of which contain pendent phenyl groups attached to C9 of the xanthene rings), D1 can be linked via its xanthene ring (preferably via C4)) to the pendent phenyl ring of D2 (e.g., via a 5- or 6-carboxy group on the pendent phenyl group). This is referred to as a head to tail arrangement. Alternatively, the positions of the connections can be reversed, such that D2 is linked via its xanthene ring to the pendent phenyl ring of D1 (another example of a head to tail arrangement). In other alternatives, D1 and D2 can be connected tail to tail, via their pendent phenyl rings, or head to head, via their xanthene rings, for example.

As noted above, at least one of L1 and L2 is an anionic linker. The properties of such anionic linkers are generally as discussed for anionic linker L above.

In one embodiment, L1 is an anionic linker and L2 is a non-anionic linker. For L2, any of a variety of non-anionic linkers can be used to connect D1 to D2. General considerations for forming donor-acceptor conjugates are discussed in U.S. Pat. Nos. 5,863,727, 5,800,996, 5,945,526, and 6,008,379, for example. In one set of embodiments, D1-L2-D2 may comprise one of structures (a), (b) or (c) below:

-D1-R$_{21}$Z$_1$C(O)R$_{22}$R$_{28}$-D2     (a)

-D1-R$_{28}$R$_{22}$C(O)Z$_1$R$_{21}$-D2     (b)

-D1-R$_{28}$R$_{22}$R$_{28}$-D2     (c)

wherein: R$_{21}$ is C$_1$-C$_5$ alkyldiyl, Z$_1$, is NH, S, or O, R$_{22}$ is an alkene, diene, alkyne, or a 5- or 6-membered ring having at least one unsaturated bond or a fused ring structure, and R$_{28}$ is a bond or spacer group. Details and examples of such inter-dye linkers can be found in U.S. Pat. No. 5,800,996, for example. In certain embodiments, R$_{22}$ is ethenediyl, ethynediyl, 1,3-butadienediyl, or 1,3-butadiynediyl.

In another embodiment, L1 is a non-anionic linker and L2 is an anionic linker. In this case, any of a variety of non-anionic linkers can be used to connect B to D1. Descriptions of exemplary nonanionic linkers can be found in the references in Table 1 above. For example, L1 can be or contain any of the following non-limiting examples:

—C≡CCH$_2$NH—

—C≡CCH$_2$OCH$_2$CH$_2$NH—

—C≡CCH$_2$OCH$_2$CH$_2$OCH$_2$CH$_2$NH—

—C≡CCH$_2$NHC(O)(CH$_2$)$_5$NH—

—C≡CC(O)NH(CH$_2$)$_5$NH—

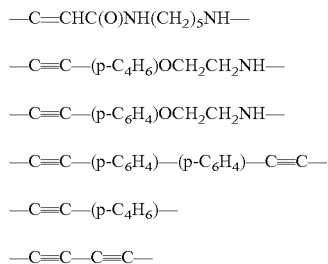

wherein the left-hand ethene or ethyne moiety is linked to the nucleobase, and the right hand bond is typically linked directly to the dye or is linked indirectly to the dye through a carbonyl group. Additional nonanionic linkers are shown in the exemplary compounds in the attached Figures.

More generally, non-anionic linkers encompass linkers that are either charge-neutral or are positively charged. Charge-neutral linkers refer to linkers that either contain no charged groups at pH 7 (i.e., has no charged group having a pKa between 6 and 8), or contain equal numbers of positively and negatively charged groups which cancel to provide a net charge of zero. A positively charged linker is positively charged at pH 7, e.g., due to the presence of an ammonium ion or imidazole ion, for example. Preferably, a non-anionic linker is a charge-neutral linker. Preferably, the charge-neutral linker contains no charged groups at pH 7.

When L1 and L2 are both anionic linkers, the structures of L1 and L2 can be the same or different, and the anionic group(s) in the linkers can also be the same or different. Further guidance regarding conjugate structures in accordance with the invention is provided below.

Compounds of the invention may be prepared by any suitable synthetic method. Typically, conjugates of the invention are formed using a modular approach in which a nucleobase (which may be provided in the form of a nucleoside or nucleotide containing the nucleobase, for example), a first dye, a second dye (if present), and one or more linkers or linker precursors, are combined in serial and/or parallel steps to produce the desired labeled product. Several exemplary approaches are illustrated in the Examples below, which describe syntheses of several different dye-labeled nucleotides containing linkers of various lengths and compositions.

Example 1 describes a synthetic method for preparing a labeled nucleotide in accordance with the invention, which contains a (i) first dye linked via C-8 of a 7-deazaadenine nucleobase by an anionic linker that contains a phosphate diester moiety within the chain of linker atoms, and (ii) a second dye linked to the first dye by a charge-neutral (non-anionic) linker. The linker between the nucleobase and the first dye contains 13 linker chain atoms. The linker between the first and second dyes contains 10 linker atoms. In this example, a bifunctional linker moiety 7 is formed in several steps by first reacting a cyclic phosphoramidite 1 with methyl glycolate 2, followed by oxidation, to form phosphate compound 3. After removal of a methyl group from the phosphate to produce 4, and deprotection of the amino and carboxyl groups to produce compound 5, an Fmoc protecting group is attached to the amine to produce carboxylic acid 6. Activation of the carboxylic acid with N-hydroxysuccinimide (NHS) produces ester 7, which is a versatile linker synthon. Ester 7 is then reacted with 7-aminopropargyl-7-deazaadenosine triphosphate 8 to form compound 9. For reaction with compound 9, dye compound 11 was prepared by reacting p-aminomethylbenzoic acid with Fmoc acid chloride to form Fmoc protected p-aminomethylbenzoic acid. After activation of the benzoic acid with NHS, the NHS ester product was reacted with 4'-aminomethyl-6-carboxyfluorescein to produce the expected amide adduct. The 6-carboxyl group was then reacted with NHS to produce dye compound 11. Reaction of compounds 10 and 11 produced adduct 12, in which an anionic (phosphate-containing) linker is formed fully between the fluorescein dye and the nucleobase. After removal of the Fmoc group, the resultant free amine compound 13 was reacted with rhodamine NHS ester 14 to form dye-labeled nucleotide 15.

An alternative method for preparing compound 10 used in Example 1 is provided in Example 2. This Example describes a synthetic approach in which a linker synthon 19 containing a phosphate monoester is prepared for reaction with a nucleoside containing an iodinated nucleobase (7-iodo-7-deazaadenine). In brief, 3-amino-1-propyne 16 is reacted with methyl glycolate 2 to form the expected amide product 17. Reaction of 17 with cyclic phosphoramidite 1 followed by oxidation affords phosphate triester 18. After removal of the phosphate group, resultant phosphodiester compound 19 is reacted with iodo-nucleoside 20 to afford adduct 21. The 5'-hydroxyl group of the nucleoside can be converted to a triphosphate group by reaction with phosphorous oxychloride to form dichloromonophosphate 22, followed by addition of pyrophosphate to provide nucleoside triphosphate 23. Removal of the trifluoroacetyl protecting group from the terminal amine nitrogen provides synthon 10.

Example 4 describes synthesis of a synthetic method for preparing a FRET-labeled nucleotide which contains a (i) first dye linked to a 7-deazaadenine nucleobase by a charge-neutral (non-anionic) linker, and (ii) a second dye linked to the first dye by an anionic linker that contains a monoanionic sulfonic acid moiety. The linker between the nucleobase and the first dye contains 5 linker chain atoms. The linker between the first and second dyes contains 10 linker atoms. As detailed in Example 4, p-aminomethylbenzoic acid 24 is reacted with sulfuric acid to form the meta-sulfonated product 25. Reaction with Fmoc-succinimide affords Fmoc protected amine 26, which is then reacted with N-hydroxysuccinimide to form NHS ester 27. For reaction with NHS ester 21, dye-labeled nucleoside triphosphate 30 can be prepared by reacting aminopropargyl nucleoside triphosphate 8 with dye intermediate 28 (a fluorescein dye containing a trifluoroacetyl-protected 4'-aminomethyl group and an NHS ester of a 6-carboxyl group) to afford dye-labeled nucleotide 29, followed by removal of the trifluoroacetyl (TFA) group to afford amine compound 30. Reaction of NHS ester 27 and compound 30 affords Fmoc-protected compound 31. After removal of the Fmoc group, resultant amine compound 32 is reacted with dye NHS ester 14 to afford dye-labeled nucleotide 33. It can be seen that the linker between the first and second dyes contains a sulfonic acid group which is attached to a benzene moiety in the linker chain.

In Example 5, a protocol is described for preparing a labeled nucleotide in which first and second dyes of a donor-acceptor pair are linked by a phosphate-containing linker, and the donor dye is linked to a nucleobase by a charge-neutral linker. This nucleotide product differs from the product of Example 1 since the anionic phosphate linker is located between the first dye and the nucleobase. The product of Example 5 also differs from the product of Example 4 since the anionic linker between the two dyes contains a phosphate monoester in the linker chain, rather than a sulfonic acid group attached to the linker chain. The compounds also differ in the lengths of some of the linkers.

As detailed in Example 5, aminopropargyl nucleotide 8 is combined with dye NHS ester 11 to afford Fmoc-protected compound 34. Following removal of the Fmoc group, resultant amine 35 is reacted with ester 7 to produce Fmoc protected dye-labeled nucleotide 36. After removal of the Fmoc group, resultant amine 37 is reacted with dye NHS ester 14 to afford dye-labeled nucleotide 38.

A method for preparing a FRET-labeled nucleotide containing two anionic linkers is described in Example 6. In particular, the anionic linker between the nucleobase and first dye contains a phosphate diester moiety, and the anionic linker between the first and second dyes contains a sulfonic acid moiety. In the method described in Example 6, nucleotide amine 10 (Examples 1 and 2) is reacted with dye NHS ester 28 to form dye-labeled nucleotide 39, in which the dye and nucleotide are linked by a phosphate-containing linker. Removal of the Fmoc group produces amine compound 40, which is reacted with sulfonate-containing NHS ester 27 to afford Fmoc-protected compound 41. After removal of the Fmoc group, resultant amine 42 is reacted with dye NHS ester 14 to afford dye-labeled nucleotide 43.

Example 7 illustrates how the dye-labeled nucleotide compound 40 from Example 6 can be used to form a conjugate of the invention by an alternative route, relative to the route described in Example 1. In Example 1, the main linker synthon between the first and second dyes is provided as part of compound 11, which contains a first dye (for attachment to the nucleobase) and an Fmoc-protected linker synthon that is attached to the first dye. In the method of Example 7, the linker is provided as part of a compound (44) which contains a linker synthon attached to the second dye. This compound can be reacted with dye-labeled nucleotide 40 to obtain desired product 15. Thus, Example 7 illustrates how the order of connection of various synthons can be varied, if desired, to synthesize a particular compound of the invention.

Examples 8A-8B describe methods for preparing two FRET-labeled nucleotides that are similar to the product of Example 1, except that the nucleobase is cytosine. In Example 8A, the linkers are the same as for the product of Example 1. In Example 8B, the linker between the nucleobase and first dye is longer than the corresponding linker in Example 8A, due to the inclusion of an ethoxy group inserted after the propargyl group.

Examples 9, 10 and 11 describe methods for making additional FRET-labeled nucleobases (thymine) which contain selected anionic linkers between first and second dyes. The method in Example 9 produces a product 64 that has a sulfonate-containing anionic linker between the two dyes, and a charge-neutral linker between the first dye and nucleobase. Product 69 from Example 10 has a phosphate-containing anionic linker between the first and second dyes. This anionic linker is also longer than the linker of Example 9 (18 linker chain atoms versus 10 linker chain atoms). The method in Example 11 produces a product 77 similar to product 69, except that the nucleobase is 7-deazaguanosine, and the attached dye is different.

Methods for preparing several exemplary dye-labeled conjugates of the form B-L-D are provided in Examples 12, 13 and 18. Example 12A describes a method for preparing a dye-labeled conjugate 82 having an anionic linker that contains a sulfonate group, as illustrated by a sulfonated benzene moiety. In Example 12B, dye-labeled conjugate 85 has a dianionic linker (net formal charge of −2) that contains both a sulfonate group and a phosphate group. In Example 13, dye-labeled conjugate 95 has an anionic linker containing a phosphodiester moiety within the linker chain.

Figure 22A:
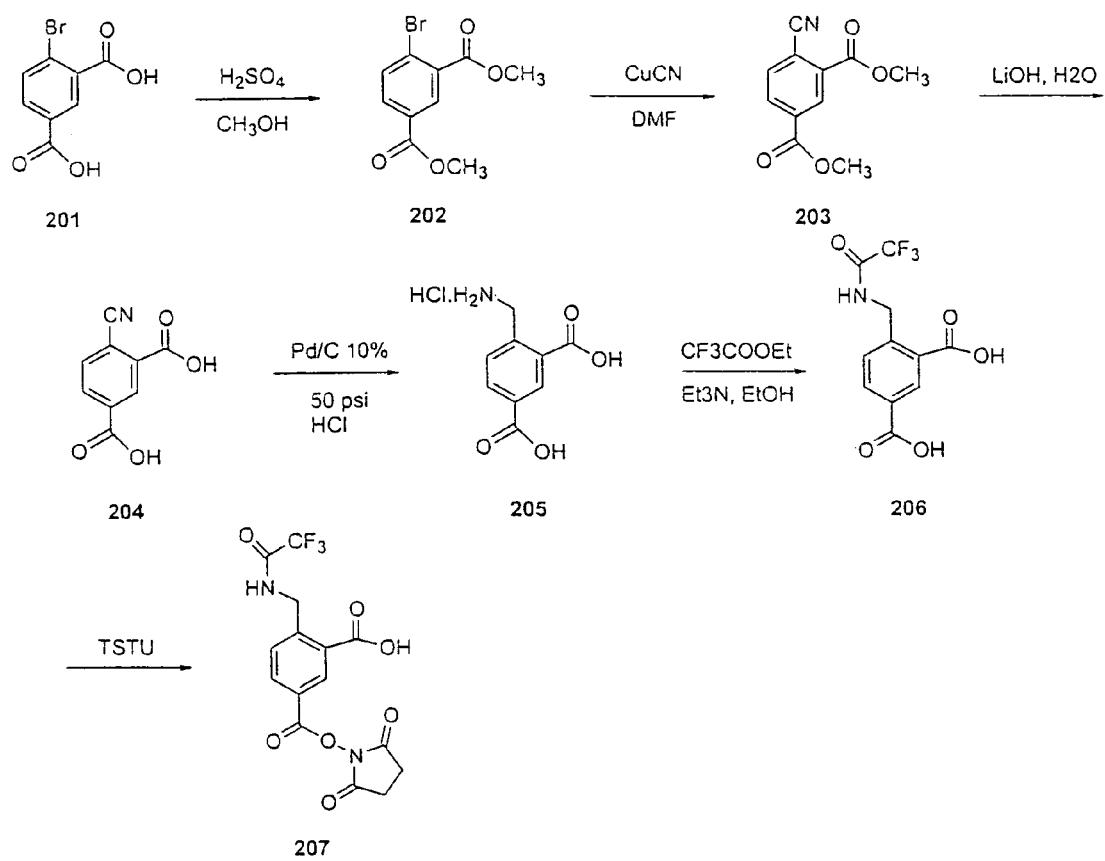

Example 18 (see also FIGS. 22A and 22B) provides a method of forming a conjugate of the form B-L-D having a linker that comprises a carboxyl anionic group, as illustrated with a carboxy benzene moiety as part of the linker. It will be appreciated that carboxylic acid groups can also be included in linkers in other ways, by preparing appropriate carboxylated linker synthons.

Examples 14, 15 and 16 provide additional methods for preparing FRET-labeled conjugates wherein the nucleobase and first dye are linked by an anionic linker, and the donor and acceptor dyes are linked by a charge-neutral linker. The nucleobase in Examples 14 and 16 is 7-deazaadenine. The nucleobase in Example 15 is 7-deazaguanine. In Example 14, a phosphodiester moiety is linked to a 7-propargyl group on the nucleobase, and the remainder of the linker is provided as an ethylaminoacyl moiety linked to the pendent phenyl ring of a fluorescein dye. In Example 15, a phosphodiester moiety is linked to the nucleobase by a 7-propargylphenylpropynyl group, and the remainder of the linker is provided as an ethylaminoacyl moiety. In Example 16, a phosphonate monoester is linked to the nucleobase by a methylacylaminopropargyl group, and the remainder of the linker is provided as an ethylaminoacyl moiety.

The foregoing examples illustrate a broad variety of dye-labeled nucleobase compounds in accordance with the invention, including four different types of nucleobases, linkers of different compositions and lengths, a number of different types of dyes, and various combinations thereof. Several specific examples of conjugates of the form B-L1-D1-L2-D2 are described wherein L1, L2 or both, are anionic linkers of various types and lengths. Specific examples of conjugates of the form B-L-D are also provided (Examples 12A, 12B, and 13), and modifications should be immediately apparent from the FRET pair Examples in which L1 is an anionic linker.

The present invention also includes nucleosides and nucleotides containing conjugates in accordance with the invention. Particularly preferred nucleosides/tides of the present invention are shown below in the following formula:

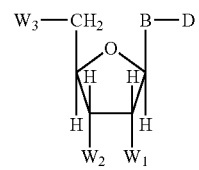

wherein $W_1$ is OH, H, F, Cl, $NH_2$, $N_3$, or OR, where R is C1-C6 alkyl (e.g., $OCH_3$ or $OCH_2CH_3$); $W_2$ is OH or a group capable of blocking polymerase-mediated template-directed primer extension (such as H, F, Cl, $NH_2$, $N_3$, or OR, where R is C1-C6 alkyl (e.g., $OCH_3$ or $OCH_2CH_3$)); $W_3$ is OH, or mono-, di- or triphosphate or a phosphate analog thereof; and LB (labeled base) represents a dye-labeled nucleobase conjugate of the invention. In one embodiment, $W_1$ is not OH. In another embodiment, $W_2$ is not OH, so that the compound is not 3' extendable. In another embodiment, $W_1$ and $W_2$ are selected from H, F, and $NH_2$. In further embodiments, $W_1$ is F and $W_2$ is H, or $W_1$ is H and $W_2$ is F, or $W_1$ and $W_2$ are each F, or $W_1$ and $W_2$ are each H. In addition, for each of the foregoing embodiments for $W_1$ alone, $W_2$ alone, and $W_1$ and $W_2$ in combination, it is contemplated that $W_3$ can be OH, monophosphate, diphosphate, or triphosphate. For LB, exemplary nucleobases include adenine, 7-deazaadenine, 7-deaza-8-azaadenine, cytosine, guanine, 7-deazaguanine, 7-deaza-8-azaguanine, thymine, uracil, and inosine.

For example, in one particular embodiment, when $W_3$ is triphosphate, the present invention includes nucleotide triphosphates having the structure shown in the formula below:

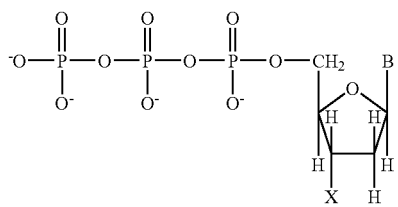

wherein X is H or F. Such terminator nucleotides, and others discussed above which lack a 3' OH group, find particular application as chain terminating agents in Sanger-type DNA sequencing methods utilizing fluorescent detection, and also in minisequencing.

In another embodiment, the invention includes deoxynucleotide triphosphates having the structure shown in the formula below:

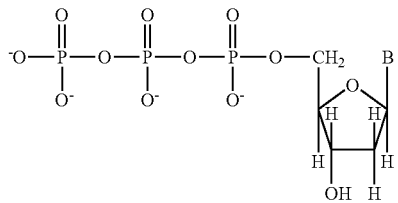

wherein LB is defined as above. Such compounds are examples of 3' extendable nucleotides. Labeled 2'-deoxynucleotides of this type find particular application as reagents for labeling polymerase extension products, e.g., in the polymerase chain reaction and nick-translation.

In yet another embodiment, the invention includes ribonucleotide triphosphates having the structure shown in the formula below:

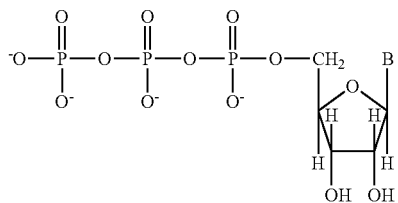

wherein LB is defined as above. Labeled nucleotides of this type find particular application as reagents for and in sequencing methods that utilize labile nucleotides having cleavable internucleotide linkages, as discussed for example in U.S. Pat. No. 5,939,292 (Gelfand et al.), Eckstein, *Nucl. Acids Res.* 16:9947-9959 (1988), and Shaw, *Nucl. Acids Res.* 23:4495 (1995).

The invention also provides polynucleotides and mixtures of polynucleotides that contain one or more different nucleobase-dye conjugates of the type discussed above. Such polynucleotides are useful in a number of important contexts, such as DNA sequencing, ligation assays, the polymerase chain reaction (PCR), probe hybridization assays, and various other sequence detection or quantitation methods.

Dye-containing polynucleotides (also referred to herein as labeled polynucleotides) may be synthesized enzymatically, e.g., using a DNA or RNA polymerase, nucleotidyl transferase, ligase, or other enzymes, e.g., Stryer, *Biochemistry*, Chapter 24, W.H. Freeman and Company (1981), or by chemical synthesis, e.g., by the phosphoramidite method, the phosphite-triester method, or the like. Dye-labels of the invention may be introduced during enzymatic synthesis utilizing labeled nucleotide triphosphate monomers as described above, or during chemical synthesis using labeled non-nucleoside or nucleoside phosphoramidites, or may be introduced subsequent to synthesis. Exemplary methods for forming labeled polynucleotides can be found in Sambrook et al., *Molecular Cloning: A Laboratory Manual*, 2nd Ed., Cold Spring Harbor Laboratory Press, NY (1989), U.S. Pat. No. 6,008,379 (Benson et al.), and references cited therein.

Generally, if a labeled polynucleotide is made using enzymatic synthesis, the following procedure may be used. An oligonucleotide primer is annealed to a complementary sequence in a template DNA strand. A mixture of deoxynucleotide triphosphates (such as dGTP, dATP, dCTP, and dTTP) is added, where at least one of the deoxynucleotides contains a nucleobase-dye conjugate of the invention. In the presence of a polymerase enzyme, a dye-labeled polynucleotide is formed by incorporation of a labeled deoxynucleotide during polymerase-mediated strand synthesis. In an alternative enzymatic synthesis method, two primers are used instead of one, one primer complementary to the +strand and the other complementary to the −strand of the target, the polymerase is a thermostable polymerase, and the reaction temperature is cycled between a denaturation temperature and an extension temperature, thereby exponentially synthesizing (amplifying) a labeled complement to the target sequence by PCR, e.g., *PCR Protocols*, Innis et al. eds., Academic Press (1990).

Labeled polynucleotides may be chemically synthesized using any suitable method, such as the phosphoramidite method. Detailed descriptions of the chemistry used to form polynucleotides by the phosphoramidite method are provided elsewhere, e.g., Caruthers et al., U.S. Pat. Nos. 4,458,066 and 4,415,732, Caruthers et al., *Genetic Engineering* 4: 1-17 (1982), *Users Manual Model* 392 and 394 *DNA/RNA Synthesizers*, pages 6-1 through 6-22, Applied Biosystems, Part No. 901237 (1991). Descriptions of the phosphoramidite method and other synthesis methods for making polynucleotides containing standard phosphodiester linkages or linkage analogs can be found in Gait, *Oligonucleotide Synthesis*, IRL Press (1990), and S. Agrawal, *Protocols for Oligonucleotides and Analogs*, Methods in Molecular Biology Vol. 20, Humana Press, Totowa, N.J. (1993).

The phosphoramidite method is a preferred method because of its efficient and rapid coupling and the stability of the starting materials. The synthesis is performed with a growing polynucleotide chain attached to a solid support, so that excess reagents, which are in the liquid phase, can be easily removed by filtration, thereby eliminating the need for purification steps between synthesis cycles.

III. Methods

The nucleobase-dye conjugates of the present invention are suited for any method utilizing fluorescent detection, particularly methods requiring simultaneous detection of analytes which are not well separated by electrophoresis. The present invention is particularly well suited for detecting classes of polynucleotides that have been subjected to a biochemical separation procedure, such as electrophoresis.

In one aspect, the invention provides a method of identifying one or more polynucleotide(s). The method utilizes one or more labeled different-sequence polynucleotides, which may have the same lengths or different lengths, wherein each different-sequence polynucleotide contains a unique nucleobase-dye conjugate. The one or more labeled different-sequence polynucleotides are separated by electrophoresis to separate different-sequence polynucleotides on the basis of size. Each different-sequence polynucleotide can then be identified on the basis of its electrophoretic mobility and fluorescence signal.

The polynucleotide(s) may be formed by any appropriate method, with the proviso that each different polynucleotide is identifiable on the basis of a unique combination of electrophoretic mobility and fluorescence signal. For example, two different polynucleotides may contain identical dye moieties but may exhibit different electrophoretic mobilities. Alternatively, two different polynucleotides can contain different dye moieties that produce distinct (spectrally resolvable) fluorescence signals but can exhibit the same electrophoretic mobilities. In another example, different polynucleotides can differ in both their fluorescence signals and mobilities.

In one embodiment, the method can be used in a multiplex format in which different labeled polynucleotides are formed by reaction with (i) a plurality of different target sequences and (ii) a plurality of different polynucleotides that are complementary to the target sequences. For example, the different polynucleotide can be designed to undergo a change in structure after hybridization to their complementary target sequences in a polynucleotide sample, e.g., due to modification by enzyme action, thereby producing different labeled polynucleotides having unique combinations of mobility and fluorescence to allow identification. Such reactions can be performed simultaneously in a single reaction mixture or can be performed in separate reaction mixtures that can be combined prior to electrophoretic separation. Several examplary assay formats for producing such labeled polynucleotides are discussed below.

Sanger-type sequencing involves the synthesis of a DNA strand by a DNA polymerase in vitro using a single-stranded or double-stranded DNA template whose sequence is to be determined or confirmed. Synthesis is initiated at a defined site based on where an oligonucleotide primer anneals to the template. The synthesis reaction is terminated by incorporation of a nucleotide analog that will not support continued DNA elongation. Exemplary chain-terminating nucleotide analogs include the 2',3'-dideoxynucleoside 5'-triphosphates (ddNTPs) which lack the 3'-OH group necessary for 5' to 3' DNA chain elongation. When proper proportions of dNTPs (2'-deoxynucleoside 5'-triphosphates) and one of the four ddNTPs are used, enzyme-catalyzed polymerization will be terminated in a fraction of the population of chains at each site where the ddNTP is incorporated. If labeled ddNTPs are used for each reaction, a desired sequence read can be obtained by detection of the fluorescence signals of the terminated chains during or after separation by high-resolution electrophoresis. In the chain termination method, dyes of the invention can be attached to either sequencing primers or terminator nucleotides.

In "fragment analysis" or "genetic analysis" methods, labeled polynucleotide fragments can be generated through template-directed enzymatic synthesis using labeled primers or nucleotides, e.g., by polynucleotide ligation or polymerase-directed primer extension. The resultant fragments are then subjected to a size-dependent separation process, e.g., electrophoresis or chromatography, and the separated fragments are detected, e.g., by laser-induced fluorescence. In a particular embodiment, multiple classes of polynucleotides are separated simultaneously and the different classes are distinguished by spectrally resolvable labels.

A fragment analysis method, known as amplified fragment length polymorphisim detection (AmpFLP), is based on amplified fragment length polymorphisms, i.e., restriction fragment length polymorphisms that are amplified by PCR. These amplified fragments of varying size serve as linked markers for following mutant genes in family lineages. The closer the amplified fragment is to the mutant gene on the chromosome, the higher the linkage correlation. Because genes for many genetic disorders have not been identified, these linkage markers serve to help evaluate disease risk or paternity. In the AmpFLP technique, the polynucleotides may be labeled by using a labeled polynucleotide PCR primer, or by utilizing labeled nucleotide triphosphates in the PCR.

In another fragment analysis method, known as nick translation, one or more unlabeled nucleotide subunits in a double-stranded DNA molecule are replaced with labeled subunits. Free 3'-hydroxyl groups are created within the unlabeled DNA by "nicks" caused by treatment with deoxyribonuclease I (DNAase I). The DNA polymerase I then catalyzes the addition of one or more labeled nucleotides to the 3'-hydroxyl of the nick. At the same time, the 5' to 3'-exonuclease activity of this enzyme can remove one or more nucleotide subunits from the 5'-phosphoryl terminus of the nick. A new nucleotide with a free 3'-OH group is incorporated at the position of the excised nucleotide, and the nick is shifted along by one nucleotide unit in the 3' direction. This 3' shift will result in the sequential addition of new labeled nucleotides to the DNA with the removal of existing unlabeled nucleotides. The nick-translated polynucleotide is then analyzed using a separation process, e.g., electrophoresis.

Another exemplary fragment analysis method is based on the variable number of tandem repeats, or VNTRs. VNTRs are regions of double-stranded DNA that contain adjacent multiple copies of a particular sequence, with the number of repeating units being variable among different members of a population (e.g., of humans). Examples of VNTR loci are pYNZ22, pMCT118, and Apo B. A subset of VNTR methods are based on the detection of microsatellite repeats, or short tandem repeats (STRs), i.e., tandem repeats of DNA characterized by a short (2-4 bases) repeated sequence. One of the most abundant interspersed repetitive DNA families in humans is the (dC-dA)n-(dG-dT)n dinucleotide repeat family (also called the (CA)n dinucleotide repeat family). There are thought to be as many as 50,000 to 100,000 (CA)n repeat regions in the human genome, typically with 15-30 repeats per block. Many of these repeat regions are polymorphic in length and can therefore serve as useful genetic markers. Preferably, in VNTR or STR methods, label is introduced into the polynucleotide fragments by using a dye-labeled PCR primer.

In another example, known sometimes as an oligonucleotide ligation assay (OLA), two polynucleotides (probe pair) which are complementary to adjacent regions in a target sequence are hybridized to the target region of a polynucleotide, to create a nicked duplex structure in which the ends of the two polynucleotide abut each other. When the ends of the hybridized polynucleotide probes match (basepair with) corresponding subunits in the target, the two probes can be joined by ligation, e.g., by treatment with ligase. The ligated product is then detected, evidencing the presence of the target sequence. In a modification of this approach, known as the ligation chain reaction (or ligation amplification reaction), the ligation product acts as a template for a second pair of polynucletide probes which are complementary to the ligated product from the first pair. With continued cycles of denaturation, reannealing and ligation in the presence of the two complementary pairs of probe, the target sequence is amplified exponentially, allowing very small amounts of target sequence to be detected and/or amplified. Exemplary conditions for carrying out such processes, including chemical ligation formats, are described in U.S. Pat. No. 5,962,223 (Whiteley et al.), U.S. Pat. No. 4,988,617 (Landegren et al.), and U.S. Pat. No. 5,476,930 (Letsinger et al.), and European Patent Publications EP 246864A (Carr et al.), EP 336731A (Wallace), and EP 324616A (Royer et al.).

Conveniently, a fragment analysis method such as any of those discussed above can be performed in a multi-probe format, in which a sample is reacted with a plurality of different polynucleotide probes or probe sets which are each specific for a different target sequence, such as different alleles of a genetic locus and/or different loci. The probes are designed to have a unique combination of mobility and fluorescence signal, to permit specific detection of the individual probes or probe products that are generated in the assay as a result of the presence of the different target sequences.

In the above fragment analysis methods, labeled polynucleotides are preferably separated by electrophoretic procedures. Methods for electrophoresis of nucleic acids are well known and are described, for example in Rickwood and Hames, Eds., *Gel Electrophoresis of Nucleic Acids: A Practical Approach*, IRL Press Limited, London (1981), Osterman, *Methods of Protein and Nucleic Acid Research*, Vol. 1 Springer-Verlag, Berlin (1984), Sambrook et al. (1989, supra), P. D. Grossman and J. C. Colburn, Capillary Electrophoresis: Theory and Practice, Academic Press, Inc., NY (1992), and U.S. Pat. Nos. 5,374,527, 5,624,800 and/or 5,552,028. Typically, the electrophoretic matrix contains crosslinked or uncrosslinked polyacrylamide having a concentration (weight to volume) of between about 2-20 weight percent, and often about 4 to 8 percent. For DNA sequencing, the electrophoresis matrix usually includes a denaturing agent such as urea, formamide, or the like. Detailed exemplary procedures for forming such matrices are given by Maniatis et al., "Fractionation of Low Molecular Weight DNA and RNA in Polyacrylamide Gels Containing 98% Formamide or 7 M Urea," in *Methods in Enzymology*, 65: 299-305 (1980), Sambrook et al. (1989, supra), and *ABI PRISM™ 377 DNA Sequencer User's Manual*, Rev. A, January 1995, Chapter 2 (p/n 903433), Applied Biosystems, Foster City, Calif.). A variety of suitable electrophoresis media are also commercially available from Applied Biosystems and other vendors, including non-crosslinked media, for use with automated instruments such as the Applied Biosystems "3700" and "3100" Instruments, by way of example. Optimal electrophoresis conditions, e.g., polymer concentration, pH, temperature, voltage, concentration of denaturing agent, employed in a particular separation depends on many factors, including the size range of the nucleic acids to be separated, their base compositions, whether they are single stranded or double stranded, and the nature of the polynucleotides for which information is sought by electrophoresis. Accordingly application of the invention may require standard preliminary testing to optimize conditions for particular separations.

During or after electrophoretic separation, the labeled polynucleotides can be detected or identified by recording fluorescence signals and migration times (or migration distances) of the separated polynucleotides, or by constructing a chart of relative fluorescent and order of migration of the polynucleotides (e.g., as an electropherogram). To perform such detection, the labeled polynucleotides can be illuminated by standard means, e.g. a high intensity mercury vapor lamp, a laser, or the like. Typically, the labeled polynucleotides are illuminated by laser light generated by a He—Ne gas laser or a solid-state diode laser. The fluorescence signals can then be detected by a light-sensitive detector, e.g., a photomultiplier tube, a charged-coupled device, or the like. Exemplary electrophoresis detection systems are described elsewhere, e.g., U.S. Pat. Nos. 5,543,026, 5,274,240, 4,879,012, 5,091,652 and 4,811,218.

FIGS. 19A-19B, 20A-20B, and 21A-21B show various results in support of the present invention. The results were obtained for sequencing fragments prepared by template-dependent primer extension in the presence of selected dye-labeled terminators following the methodology described in U.S. Pat. No. 6,096,875 (see Example 12, except that the primers were not labeled). Primer extension reactions were performed in the presence of a single type of terminator to generate a ladder of extension fragments. The two extension reactions in each study differed only in the linkers that were present between the nucleobase and the dye, or between a donor dye and acceptor dye. Specifically, the linker in one reaction mixture (A) is non-anionic, whereas the linker in the other reaction mixture (B) is an exemplary anionic linker.

Figure 19A:
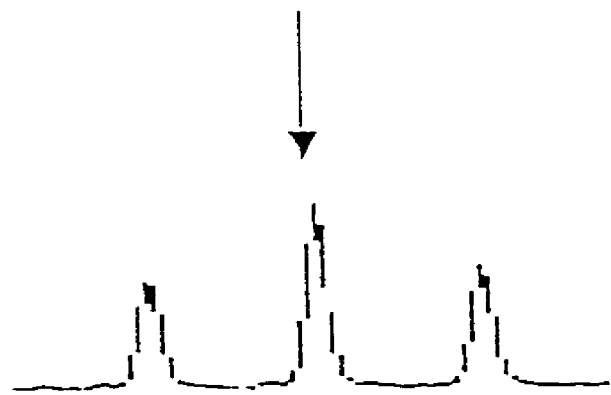
FIGS. 19A and 19B show electropherograms of sequencing ladders terminating with a first set of terminators (ddG).
Figure 19B:
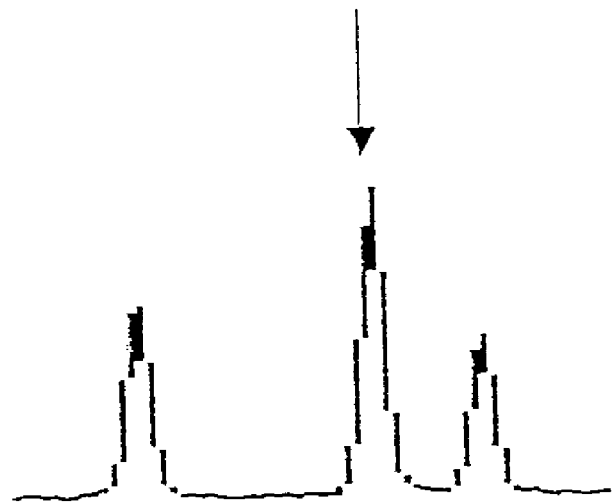

For FIGS. 19A and 19B, two primer extension reactions were performed using 7-deaza analogs of dideoxyguanosine-5'-triphosphate (ddGTP). Both terminators contained only one dye, which is a dibenzoxanthene dye of the type described in U.S. Pat. No. 5,936,087 at FIG. 14, wherein $R_1$ is $CH_2$-p-$C_6H_4$ and $R_2$ is propyldiyl, and wherein the C4 and C10 of the benzo groups are sulfonated. The dye is linked by the 12-nitrogen atom of the dibenzoxanthene ring structure to C7 of the 7-deazaguanine ring. For FIG. 19A, the structure of the L linker is B—C≡CCH$_2$OCH$_2$CH$_2$NHC(O)-p-C$_6$H$_4$CH$_2$-D, wherein B represents C7 of the nucleobase and D represents N12 of the dye. For FIG. 19B, the structure of the L linker is B—C≡CCH$_2$OCH$_2$CH$_2$NHC(O)CH$_2$OP(O)(OH)OCH$_2$CH$_2$—NH—C(O)-p-C$_6$H$_4$CH$_2$-D, wherein B and D are as just described.

An arrow in FIG. 19A points to a middle peak flanked on each side by a left peak and a right peak. The spacing between the left and middle fragments appears to be about equal to the spacing between the middle and right fragments, suggesting that the target sequence contains three cytosine subunits (complementary to the ddG terminator) which are separated from each other by an equal number of intervening subunits. However, based on the known sequence of the target template (pGEM), the 3'-terminal subunits of the fragments corresponding to the left and middle peaks are known to be separated by three intervening subunits, whereas the 3'-terminal subunits of the fragments corresponding to the middle and right peaks are separated by only one intervening subunit. In other words, the middle peak is four subunits longer than the left peak, and the right peak is only two subunits longer than the middle peak. Thus, based on the observed profile in FIG. 19A, a user would have great difficulty in determining the correct target sequence. For example, if primer extension had been performed in the presence of four spectrally resolvable terminator, the middle peak could co-migrate with a longer or shorter fragment containing a different terminator, thereby obscuring the correct order of the fragments and rendering indeterminate the sequence information.

In contrast, the profile in FIG. 19B, which was obtained using a dye-labeled nucleobase in accordance with the invention, has the expected spacing between the three peaks. The separation between the left and middle peaks is twice the separation between the middle and right peaks, consistent with length differences of four and two subunits, respectively, between the left, middle, and right peaks. Clearly, this profile would allow a user to more easily determine the correct target sequence. These results demonstrate how the use of an anionic linker in a dye-labeled nucleobase can significantly improve the correlation between fragment length and electrophoretic mobility of dye-labeled polynucleotides.

Figure 20A:
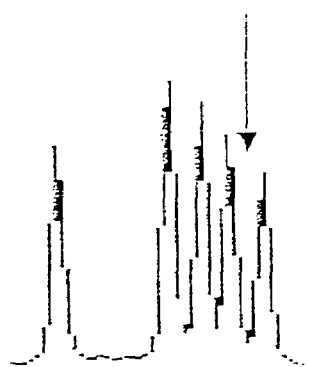
FIGS. 20A and 20B show electropherograms of sequencing ladders terminating with a second set of terminators different from those in FIGS. 1A and 1B (ddA).
Figure 20A:
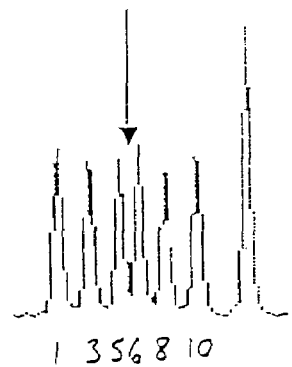
Figure 20B:
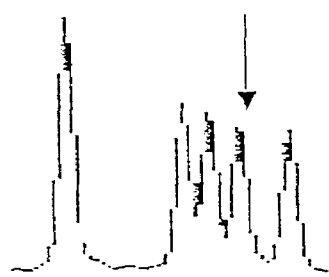
Figure 20B:
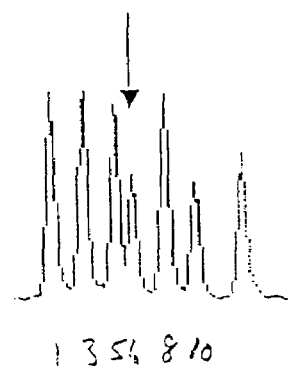

FIGS. 20A and 20B show electrophoretic profiles obtained using two different 7-deaza analogs of dideoxyadenosine-5'-triphosphate (ddATP). In this study, both terminators contained a donor/acceptor dye pair in which D1 is a 6-carboxyfluorescein containing a 5'-amino methyl group, and D2 is the same as the 5-carboxy-4,7-dichlororhodamine dye used in Example 1 herein. In both conjugates, D1 is linked via the 4'amino methyl group to C5 of the pendent phenyl ring of D2 using the L2 linker from Example 1. For FIG. 20A, B and D1 were linked by the L1 linker from Example 4 (—C≡CCH$_2$NHC(O)—). For FIG. 20B, B and D1 were linked by an L1 linker of the form: B—C≡CCH$_2$NHC(O)-p-C$_6$H$_4$(SO$_3$)CH$_2$NHC(O)-D1, wherein the sulfonate group on the benzene ring is ortho to the aminomethyl group.

The profile in the left-hand window of FIG. 20A contains a single peak that is separated from a quartet of four peaks on the right. From the approximately equal spacing between adjacent peaks in the quartet, a user would probably conclude that the target sequence contains four consecutive thymidine subunits. However, such a conclusion would be erroneous, since the target sequence actually contains an adenosine subunit between the third and fourth thymidine subunits. A profile having a significantly improved profile is shown in the left-hand window of FIG. 20B. In particular, the third and fourth peaks in the quartet are separated by a distance consistent with a length difference of two subunits for those peaks.

With reference to the right-hand windows of FIGS. 20A and 20B, the right-hand window of FIG. 20A shows a set of closely eluting peaks which are numbered 1, 3, 5, 6, 8, and 10. Based on the known template sequence, the correct terminator sequence reading is 5'-ACACAACATA-3' (SEQ ID NO:1) (corresponding to a template sequence of 3'-TGTGTTGTAT-5') (SEQ ID NO:2). Unfortunately, peaks 5 and 6 in the right-hand window of FIG. 20A are separated from each other by more than one peak interval, so that a user might conclude that the two peaks are separated by an intervening fragment corresponding to the presence of an intervening subunit in the target sequence. (One "peak interval" refers to the average spacing between adjacent peaks differing in length by one nucleotide, for a selected region of an electropherogram.) Each peak corresponds to a unique-sequence fragment of DNA.

A profile having significantly improved spacing is shown in the right-hand window of FIG. 20B. In this case, peaks 5 and 6 are separated by about one peak interval, as expected for fragments that differ in length by one nucleotide subunit. Overall, the improvement in spacing between peaks 1, 3, 5, 6, 8 and 10 allows more accurate determination of the target sequence.

Figure 21A:
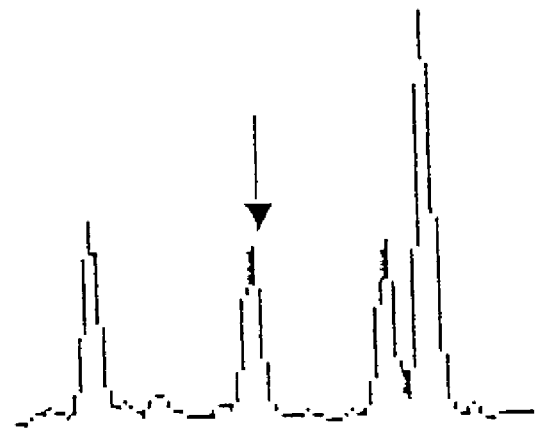
FIGS. 21A and 21B show electropherograms of sequencing ladders terminating with a third set of terminators (ddA).
Figure 21B:
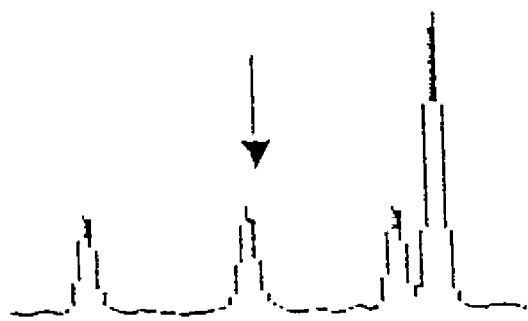

Yet another example of the advantages of the invention is illustrated in FIGS. 21A and 21B. In this study, extension reactions were performed using 7-deaza analogs of ddATP. Both terminators contained a fluorescein dye (compound 33 from U.S. Pat. No. 6,008,379) which is linked via C5 of the pendent phenyl ring to C7 of the 7-deazaadenine ring. For FIG. 21A, the structure of the L linker is B—C≡C-p-C$_6$H$_4$—C≡CCH$_2$OCH$_2$CH$_2$NHC(O)-D, wherein B represents C7 of the nucleobase and D represents C5 of the pendent phenyl ring of the dye. For FIG. 21B, the structure of the L linker is B—C≡C-p-C$_6$H$_4$—C≡CCH$_2$OCH$_2$CH$_2$NHC(O)—CH$_2$OP(O)(OH)OCH$_2$CH$_2$NHC(O)-D, wherein B and D are as just described.

FIG. 21A shows a profile containing four peaks consisting of a singlet on the left, a singlet in the middle, and a doublet on the right. From the known target sequence, the singlets should be separated from each other by four peak intervals (due to the presence of three intervening non-T subunits in the target sequence), the middle singlet and left-hand peak in the doublet should also be separated by four peak intervals, and the two peaks in the doublet should be separated from each other by one peak interval. The profile in FIG. 21A is problematic because the middle singlet is separated from the left-hand member of the doublet by approximately 3.5 peak intervals. In the profile shown in FIG. 21B, however, the spacing is more uniform, such that the middle singlet and left-hand peak in the doublet are separated by four peak intervals. Thus, the target sequence can be determined more easily using the dye-labeled terminator of FIG. 21B in accordance with the invention.

The results above demonstrate how the use of an anionic linker in a dye-labeled nucleobase can significantly improve the correlation between fragment length and electrophoretic mobility of dye-labeled polynucleotides.

In conclusion, the present invention provides conjugate compounds in which a dye and nucleobase are linked by an anionic linker, or, in the case of energy transfer dyes, one or more linkers located between a dye and a nucleobase and/or between energy transfer dyes are anionic linkers. Such linkers can be used in a variety of different forms and may include any of a variety of different anionic groups, such that base-pairing characteristics of the nucleobase and fluorescent properties of the dye are retained. Compounds of the invention are useful in nucleoside and nucleotides that can be incorporated into polynucleotides for detection. In particular, polynucleotides containing dye-labeled conjugates of the invention show reduced sequence-dependent variations in electrophoretic mobility. Thus, the invention provides electrophoretic separation patterns having more even spacing between nearby polynucleotide bands, as well as reduced band-compression, resulting in a more consistent and uniform relationship between polynucleotide length and electrophoretic mobility. Furthermore, nucleoside triphosphates that contain nucleobase-dye conjugates of the invention are good substrates for polymerase enzymes which can be used to incorporate such nucleotides into polynucleotides to form labeled polynucleotides. This is advantageous in terminator-based sequencing methods. When compounds of the invention are incorporated at the 3' ends of sequencing fragments, artifacts in electrophoretic mobility are reduced, so that accuracy of base-calling can be improved.

IV. Kits

The invention also provides kits for performing the various methods of the invention. For nucleic acid sequencing, the kit comprises at least one labeled nucleoside triphosphate comprising a conjugate described herein. The kit may also include one or more of the following components: a 3'-extendable primer, a polymerase enzyme, one or more 3' extendable nucleotides which are not labeled with conjugate, and/or a buffering agent. In some embodiments, the kit includes at least one labeled nucleoside triphosphate that is nonextendable. In other embodiments, the kit comprises four different labeled nucleoside triphosphates which are complementary to A, C, T and G, and each of which contains a distinct conjugate as described herein. In yet another embodiment, the labeled nucleoside triphosphates are nonextendable. In another embodiment, the labeled nucleoside triphosphates are extendable ribonucleoside triphosphates. In another embodiment, the kit comprises at least one labeled, nonextendable nucleoside triphosphate comprising a conjugate described herein, and one or more of the following components: a 3'-extendable primer, a polymerase enzyme, and/or a buffering agent.

The operation of the invention can be further understood in light of the following non-limiting examples which illustrate various aspects of the invention.

EXAMPLES

Materials and Methods

Unless indicated otherwise, all reagents and anhydrous solvents were purchased from Aldrich Chemicals. Thin layer chromatography (TLC) analysis was conducted on aluminum plates precoated with 250 µm layers of silica gel 60-F254. Compounds were located by UV-VIS lamp and/or by charring with aqueous $K_2MnO_4$. Flash column chromatography purification was carried out using EM Science silica gel 60 angstrom (230-400 Mesh ASTM). NMR spectra were recorded in deuterated solvents ($CDCl_3$, $CH_3OD$, and $D_2O$ with an internal $Me_4Si$ standard, δ 0). $^1H$ NMR spectra were recorded at 300 MHz, $^{13}C$ NMR spectra at 75.7 MHz, $^{19}F$ NMR spectra at 282.23 MHz, and $^{31}P$ NMR spectra at 121.44 MHz. In all cases, the observed NMR spectra were in agreement with the indicated structures. Satisfactory mass spectra were also obtained for the reported compounds.

Anion-exchange high-performance chromatography (AE-HPLC) was performed as follows. Column: Aquapore™ AX300, 7 µm particle size and 220×4.6 mm (PE Applied Biosystems). Gradient: 40% acetonitrile:60% triethylammonium bicarbonate (TEAB, 0.1 M) to 40% acetonitrile:60% TEAB (1.5 M) at 1.5 ml/min over 20 minutes. Detection: UV absorbance at 260 nm or λmax of each dye compound.

Reverse phase high-performance chromatography (RP HPLC) was performed as follows. Column: Spheri-5 RP-C18, 5 µm particle size, 220×4.6 mm (PE Applied Biosystems); gradient: 95% triethylammonium acetate (TEAA, 0.1 M): 5% acetonitrile to 50% acetonitrile: 50% TEAA at 1.5 ml/min over 20 minutes and then to 100% acetonitrile over 5 minutes.

Example 1

Synthesis of Dye-Nucleotide Conjugate 15

Methyl glycolate 2 (4.5 eq.) was added to Amino-Link™ 1 (1 eq.) (Connell, C., et al., BioTechniques 5:342-348 (1987); U.S. Pat. No. 4,757,151), followed by 4-N,N-dimethyl aminopyridine (DMAP) (0.1 eq.). The mixture was stirred at ambient temperature for 1 hour. After the reaction was complete (TLC analysis), the solution was cooled with ice-bath and then treated with a solution of 3-chloroperoxybenzoic acid (4 eq.) in methylene chloride. The ice-bath was removed. After 30 minutes, an aqueous solution of $NaHSO_3$ (10%) was added. The mixture was diluted with ethyl acetate. The organic layer was washed with $NaHSO_3$ (10%), saturated solution of $NaHCO_3$, and dried with $Na_2SO_4$. The crude product was purified by flash chromatography to afford compound 3.

To a solution of compound 3 (36 mM, 1 eq.) in methylethylketone was added NaI (10 eq.). The mixture solution was heated at reflux for 3 hours. Solvent was removed under vacuum to afford crude compound 4 with NaI which was used as such without further purification.

Crude compound 4 (1 eq.) was dissolved in 0.3 M solution of LiOH (5 eq.) in a mixed solvent $H_2O$: $CH_3OH$ (1:3). The mixture was stirred overnight. Solvent was removed to afford crude compound 5 which was then dissolved in aqueous $Na_2CO_3$ (5%). N-(9-Fluorenylmethoxy-carbonyloxy)succinimide (FmocOSu, 1.5 eq.) in THF was added in one portion. The mixture was stirred at ambient temperature for 3 hours. The crude product was purified by flash chromatography to afford compound 6.

Compound 6 (1 eq.) was dissolved in ethyl acetate and the resultant solution was washed with aqueous solution of HCl (10%). The organic layer was dried with $Na_2SO_4$. Concentration under vacuum gave a yellow oil which was dissolved in anhydrous $CH_2Cl_2$. N-hydroxysuccinimide (4 eq.) was added. The solution was cooled with an ice-bath and then treated with dicyclohexyl carbodiimide (DCC, 2 eq.). The ice-bath was then removed, and stirring was continued for 2 hours (with TLC analysis). When the reaction was complete, ethyl acetate was added and the solution was washed with aqueous solution of HCl (5%). Removal of solvent gave compound 7.

Nucleoside triphosphate 8 (7-(3-amino-1-propynyl)-2',3'-dideoxy-7-deazaadenosine-5'-triphosphate—see U.S. Pat. Nos. 5,047,519 and 5,151,507 by Hobbs et al. for synthesis) in 100 mM TEA-bicarbonate solution (pH 7.0) was evaporated to dryness. The dried residue was suspended in a solution of 250 mM bicarbonate (pH 9.0). A solution of compound 7 in DMSO was added. After 1 hour, the reaction mixture was purified by HPLC (AX-300 anion exchange). The product fractions were collected, concentrated to dryness, and purified by RP HPLC (C-18 reverse phase) to afford compound 9.

Ammonium hydroxide solution (28-30%) was added to dried compound 9. The solution was heated to 55° C. for 20 minutes. Concentration under vacuum gave crude compound 10 which was purified by HPLC (C-18 reverse phase).

NHS-ester dye intermediate 11 was prepared by reacting the fluorenylmethoxy-carbonyloxy ester of N-hydroxysuccinimide with the HCl salt of p-aminomethylbenzoic acid (both commercially available) in the presence of base to form the expected N-Fmoc derivative. This product was then reacted with N-hydroxysuccinimide in the presence of DCC to form the NHS ester of the benzoic acid carboxyl group. This NHS ester was then reacted with 4'-aminomethyl-6-carboxyfluorescein (M. T. Shipchandler et al., *Anal. Biochem.* 162:89-101 (1987)) to form the expected product. This product was then reacted with N-hydroxysuccinimide in the presence of DCC to produce NHS-ester dye intermediate 11.

Compound 10 was suspended in a solution of 250 mM bicarbonate (pH 9.0). Then a solution of dye intermediate 11 in DMSO was added. The reaction mixture was placed in the dark at ambient temperature for 2 hours. Purification was done by HPLC (AX-300 anion exchange). The recovered dye-labeled compound 12 was dried and then heated at 55° C. in ammonium hydroxide (28-30%) for 20 minutes. Concentration under vacuum gave crude compound 13 which was purified by HPLC (C-18 reverse phase).

Compound 13 was suspended in a solution of 250 mM bicarbonate (pH 9.0). Then a solution of dye 14 (e.g., see Example 17 or U.S. Pat. No. 5,847,162 for synthesis) in DMSO was added. The reaction mixture was placed in dark at ambient temperature for 2 hours. Purification was done by HPLC, AX-300 anion exchange and then C-18 reverse phase to afford pure nucleotide-dye compound 15, which contains a phosphate diester moiety within the chain of linker atoms linking the inner dye to the nucleotide.

Example 2

Alternative Synthesis of Nucleotide 10

A solution of propargyl amine 16 (3-amino-1-propyne, 3.4 eq.), DMAP (0.1 eq.), and methyl glycolate 2 (1 eq.) was heated to reflux for 2 hours. The reaction solution was cooled to ambient temperature and was poured into aqueous solution of HCl (10%). The solution was extracted with ethyl acetate. Concentration under vacuum gave desired compound 17 as a yellow solid.

In a manner similar to the method described in Example 1, reaction of compound 17 (1 eq.) and Amino-Link™ 1 (1 eq.) followed by oxidation with mCPBA gave compound 18 which was purified by flash column chromatography. Deprotection of the methyl group in 18 (1 eq.) using NaI (10 eq.) gave compound 19 after purification by flash column chromatography.

Nucleoside 20 (7-iodo-7-deazaadenosine, 1 eq.) was reacted with linker synthon 19 (2 eq.) in the presence of cuprous iodine (0.4 eq.), tetrakis(triphenylphosphine)palladium (0.4 eq.), and triethylamine (8 eq.) in N,N-dimethylformamide for 4 hours. The reaction was concentrated and purified by flash column chromatography to afford nucleoside 21.

Phosphorous oxychloride (6 eq.) was added to nucleoside 21 (1 eq.) in trimethylphosphate at 0° C. to form the corresponding dichloromonophosphate 22. The reaction mixture was stirred at 0° C. for 2 hours after which it was transferred via cannula to another flask containing tributylammonium pyrophosphate (12 eq.) and tributylamine (22 eq.) in the presence of DMF. After another 30 minutes at 0° C., the solution was quenched with TEAB buffer (1M). The solution was then stirred overnight at ambient temperature. Purification was carried out by HPLC (C-18 reverse phase) to afford nucleoside triphosphate 23. Ammonium hydroxide (28-30%) was added to dried nucleoside triphosphate 23, and the resultant solution was stirred at ambient temperature for 1 hour. Concentration under vacuum gave nucleotide 10 which was stored in 0.1 M TEAB solution. Nucleotide 10 can be used in the synthesis of compound 15 as described in Example 1.

Example 3

General Coupling Reactions

For the Examples below, the following general conditions were used. For reactions involving the coupling of an amino group to an N-hydroxysuccinimide-activated carboxyl group (NHS ester), the compound containing the amino group was suspended in 100 mM TEA-bicarbonate (pH-7.0) and evaporated to dryness. The residue was then suspended in a solution of 250 mM bicarbonate (pH 9.0), and then a solution of the compound containing the NHS ester was added. After 1 hour, the coupling reaction mixture was purified by HPLC (AX-300 anion exchange). The product fractions were collected, concentrated to dryness, and purified by HPLC (C-18 reverse phase).

Removal of trifluoroacetate protecting groups was accomplished by treatment with ammonium hydroxide (28-30%) at ambient temperature for one hour.

Fmoc groups were removed by heating at 55° C. for 20 minutes in the presence of 28-30% ammonium hydroxide.

Example 4

Synthesis of Dye-Nucleotide Conjugate 33

Aminobenzoic acid 24 (1 eq.) was dissolved in fuming sulfuric acid and the resultant solution was heated in an oil bath at 130° C. for 4 hours. The viscous solution was poured into ice and then was neutralized with a concentrated solution of sodium bicarbonate to a pH of 8 to 9. The aqueous solvent was removed under vacuum to afford crude compound 25 which was then dissolved in aqueous solution of sodium carbonate (5%). To this solution was added FmocOSu (Example 1, 1.5 eq.) in THF. The mixture was stirred at ambient temperature for 3 hours. The resultant crude compound 26 was purified by flash column chromatography.

N-hydroxysuccinimide and N,N-dimethylformamide were added to a slurry solution of compound 26 (1 eq.) in methylene chloride. The solution was cooled to 0° C., followed by addition of a solution of dicyclohexylcarbodiimide (DCC, 2 eq.) in methylene chloride. The ice-bath was removed and stirring was continued for 2 hours. The mixture was diluted with ethyl acetate, and the organic portion was washed with aqueous solution of HCl (5%). Purified NHS ester 27 was obtained by flash column chromatography.

Nucleoside triphosphate 8 (Example 1) was reacted with dye-NHS ester 28 (4'-N-trifluoroacetylaminomethyl-6-carboxyfluorescein according to procedures generally described in Example 3 to form the expected dye-labeled nucleotide 29. Removal of the trifluoroacetyl (TFA) protecting group (Example 3) from conjugate 29 afforded amine compound 30. Reaction of compound 30 with NHS ester 27 afforded the expected Fmoc-protected compound 31.

Following removal of the Fmoc group from compound 31 to afford amine 32, rhodamine NHS ester 14 was added to afford nucleotide-dye compound 33 which contains a sulfonate substituent in the linker chain between the two dyes.

Example 5

Synthesis of Dye-Nucleotide Conjugate 38

Nucleoside triphosphate 8 was reacted with Fmoc-protected fluorescein NHS ester 11 to provide the expected product 34. Following removal of the Fmoc group to afford deprotected aminomethyl compound 35, Fmoc protected NHS ester 7 was reacted with 35 to afford Fmoc-protected compound 36. Removal of the Fmoc group afforded aminoethyl phosphate ester compound 37 which was combined with rhodamine NHS ester 14 to afford nucleotide-dye compound 38.

Example 6

Synthesis of Dye-Nucleotide Conjugate 43

Nucleotide 10 (Example 1) was combined with TFA-protected fluorescein NHS ester 28 to afford the expected dye-nucleotide conjugate 39. Following removal of the TFA protecting group, the resultant deprotected product 40 was reacted with NHS ester 27 to afford Fmoc-protected conjugate 41. Removal of the Fmoc group afforded amine 42, which was reacted with rhodamine NHS ester 14 (Example 1) to afford nucleotide-dye conjugate 43 having a phosphate diester moiety within the chain of linker atoms between the inner dye and the nucleobase, and a sulfonate substituent in the linker between the two dyes.

Example 7

Alternative Route to Dye-Nucleotide Conjugate 15

NHS ester 44 (preparable by reacting dye NHS ester 14 from Example 1 with p-aminomethylbenzoic acid 24 from Example 4, followed by activation of the benzoic acid with N-hydroxysuccinimide) was combined with amino 40 (Example 6) to afford nucleotide-dye conjugate 15 (Example 1).

Example 8

Synthesis of Dye-Nucleotide Conjugates 51 and 57

8A. Using procedures described in Example 1, 5-(3-amino-1-propynyl)-2',3'-dideoxycytidine-5'-triphosphate 45 (see Hobbs et al., supra, for synthesis) was reacted with NHS ester 7 (Example 1) to afford Fmoc-protected intermediate 46. Removal of the Fmoc group afforded amine 47, which was then reacted with NHS ester 11 (Example 1) to afford conjugate 48. Removal of the Fmoc protecting group afforded amine 49, which was then reacted with rhodamine NHS ester 50 (e.g., see U.S. Pat. No. 5,847,162, for synthesis) to afford conjugate 51.

8B. The protocol in Example 8A was carried out using 5-(3-aminoethoxy-1-propynyl)-2',3'-dideoxycytidine-5'-triphosphate 52 (e.g., see U.S. Pat. No. 5,821,356 for synthesis) instead of nucleotide triphosphate 45, to afford conjugate 57.

Example 9

Synthesis of Dye-Nucleotide Conjugate 64

Using the synthetic scheme described in Example 4, conjugate 64 was prepared from 5-(3-aminoethoxy-1-propynyl)-2',3'-dideoxythymidine-5'-triphosphate 58 (e.g., see U.S. Pat. No. 5,821,356 for synthesis) instead of nucleotide 8, dye-NHS ester 28 (supra), linker NHS ester 27 (supra), and dye-NHS ester 63 (e.g., prepared following methods described in U.S. Pat. No. 6,080,852) instead of compound 14.

Example 10

Synthesis of Dye-Nucleotide Conjugate 69

Using procedures described in Example 5, conjugate 69 was prepared from 5-(3-aminoethoxy-1-propynyl)-2',3'-dideoxythymidine-5'-triphosphate 58 (Example 9) instead of nucleotide 8, dye NHS ester 11 (supra), phosphate linker synthon 7 (supra), and dye NHS ester 63 (Example 9) instead of compound 14.

Example 11

Synthesis of Dye-Nucleotide Conjugate 77

Using procedures described in Example 5, conjugate 77 was prepared from 7-(3-aminoethoxy-1-propynyl)-2',3'-dideoxy-7-deazaguanosine-5'-triphosphate 70 instead of nucleotide 8, dye NHS ester 71 (prepared in the same way as compound 11 supra, using the 5-carboxyfluorescein instead of the 6-carboxyfluorescein), phosphate linker synthon 7 (supra), and dye NHS ester 76 (e.g., see U.S. Pat. No. 5,847,162 for synthesis) instead of compound 14.

Example 12

Synthesis of Dye-Nucleotide Conjugates 82 and 85

12A. Using methods described in Example 3, sulfonate-containing linker synthon 27 (supra) was coupled to 7-(3-aminoethoxy-1-propynyl)-3'-fluoro-2',3'-dideoxy-7-deazaguanosine-5'-triphosphate 78 (e.g., see U.S. Pat. No. 5,821,356 for synthesis) to afford Fmoc-protected product 79. After the Fmoc group was removed, resultant amine 80 was reacted with NHS-activated dye 81 (e.g., see U.S. Pat. No. 6,051,719 for synthesis) to produce dye-labeled nucleotide 82 containing a sulfonated benzene linker.

12B. Dye-nucleotide conjugate 85 was prepared by coupling deprotected amine 80 (Example 12A) to phosphate-containing linker synthon 7 (supra) to afford Fmoc-protected product 83. After removal of the Fmoc group, resultant amine 84 was coupled to NHS-activated dye 81 (Example 12A) to afford dye-nucleotide conjugate 85 having a linking group containing both a sulfonate group and a phosphate group.

Example 13

Synthesis of Dye-Nucleotide Conjugate 95

Using procedures described in Example 1, methyl 4-(hydroxymethyl) benzoate 86 (1.3 eq.), Amino-Link™ 1 (Example 1, 1 eq.), and DMAP (0.1 eq.) were reacted together, followed by oxidation with mCPBA (1.5 eq.) to afford phosphotriester 87. Removal of the methyl group from the phosphotriester group using NaI (10 eq.) afforded phosphodiester 88, which was subsequently treated with LiOH (6 eq.) to remove the methyl and trifluoroacetyl protecting groups, yielding amino acid phosphate diester 89. Protection of the amino group with FmocOSu (Example 1) gave compound 90. NHS ester 91 was obtained by treating compound 90 with DCC (1.3 eq.) and N-hydroxysuccinimide (3 eq.). NHS ester 91 was added to nucleotide 78 (Example 12A) to form Fmoc-protected compound 92. After removal of the Fmoc group, resultant amine compound 93 was coupled to dye 81 (Example 12A) to afford dye-nucleotide conjugate 95 containing a phosphodiester within the linker chain.

Example 14

Synthesis of Dye-Nucleotide Conjugate 106

Using procedures described in Example 2, propargyl alcohol 96 (3-propyn-1-ol, 1.5 eq.), Amino-Link™ 1 (Example 1, 1 eq.), and DMAP (0.1 eq.) were reacted together, followed by oxidation with mCPBA (1.5 eq.) to afford phosphotriester 97. Removal of the methyl group from the phosphotriester group using NaI (10 eq.) afforded propargyl-trifluoroacetylaminoethyl phosphodiester 98.

Phosphodiester 98 (1.5 eq.) was reacted with 7-iodo-7-deazaadenosine 20 (1 eq.) in the presence of CuI (0.4 eq.), Pd[PPh$_3$]$_4$ (0.4 eq.), and triethylamine (8 eq.) in DMF to afford nucleoside product 99.

Phosphorous oxychloride (6 eq.) was reacted with nucleoside 99 (1 eq.) to form dichlorophosphate intermediate 100. This intermediate was treated with tributylammonium pyrophosphate (12 eq.) and tributylamine (22 eq.), followed by hydrolysis with TEAB buffer (1 M), to form nucleotide 5' triphosphate 101. Removal of the TFA group was achieved by ammonium hydroxide to afford nucleotide amine 102.

Dye NHS ester 11 (Example 1) was added to nucleotide amine 102 in NaHCO$_3$ buffer to afford dye-nucleotide 104.

After the Fmoc group was removed, the resultant amine compound 105 was coupled to dye NHS ester 14 (Example 1) to afford dye-nucleotide conjugate 106.

Example 15

Synthesis of Dye-Nucleotide Conjugate 123

Triethylsilylacetylene 108 (3 eq.) was coupled to 4-iodophenol 107 (1 eq.) in the presence of CuI (0.05 eq.), Pd[PPh$_3$]$_4$ (0.05 eq.), and triethylamine (2 eq.) in DMF. The mixture was stirred at ambient temperature for 5 hours after which it was concentrated under vacuum to afford a crude black oil. The oil was purified by flash column chromatography to afford pure p-(triethylsilyl)ethynyl phenol 109.

To a solution of compound 109 in dichloromethane were added triflic anhydride (trifluoromethanesulfonic anhydride, 1.2 eq.) and triethylamine (1.2 eq.) at −40° C. After 30 minutes, the reaction was quenched with water and the solution was extracted with dichloromethane. Purification was achieved by flash column chromatography to afford trifluoromethanesulfonate 111.

Propargyl alcohol 110 (1.1 eq.) was coupled to compound 111 (1 eq.) in the presence of CuI (0.1 eq.), Pd[PPh$_3$]$_4$ (0.05 eq.), and triethylamine (2 eq.) in DMF. The mixture was stirred at 60° C. for 7 hours and then concentrated under vacuum. Purification by flash column chromatography gave alcohol 112.

Alcohol 112 (1 eq.), Amino-Link™ 1 (1 eq.), and DMAP (0.1 eq.) were reacted together using procedures described above, followed by oxidation with mCPBA (1.2 eq.) to produce phosphotriester 113. Removal of the methyl group from the phosphate triester group using NaI (10 eq.) afforded phosphodiester 114.

To a solution of compound 114 in tetrahydrofuran (THF) at 0° C. was added tetra-butylammonium fluoride (1.5 eq.). After 30 minutes, the solution was quenched with aqueous ammonium chloride solution (10%) and extracted with ethyl acetate. Purification was achieved by flash column chromatography to afford phosphate-containing linker synthon 115. Compound 115 (2 eq.) was coupled to nucleoside 116 (7-iodo-3'-fluoro-2',3'-dideoxy-7-deazaguanosine, 1 eq.) (e.g., see Hobbs et al., supra, for synthesis) in the presence of CuI (0.4 eq.), Pd[PPh$_3$]$_4$ (0.4 eq.), and triethylamine (10 eq.) in DMF to afford nucleoside 117.

Phosphorous oxychloride (6 eq.) was reacted with nucleoside 117 (1 eq.) to form intermediate 118 which was treated with tributylammonium pyrophosphate (12 eq.) and tributylamine (22 eq.), followed by hydrolysis with TEAB buffer (1 M) to form nucleotide 119. Removal of the TFA group was achieved using ammonium hydroxide to afford amine 120.

Dye 71 (supra) was added to nucleotide amine 120 in NaHCO$_3$ buffer to afford dye-labeled nucleotide 122 (in these examples, there is no compound 121). After the Fmoc group was removed, the resultant amine compound 123 was coupled with dye 76 (Example 11) to afford dye-nucleotide conjugate 124.

Example 16

Nucleotide-Dye Conjugate 137 with Phosphonate-Containing Linker

Lithiated tert-butyl acetate 125, prepared from tert-butyl acetate and lithio N,N-diisopropylamine (prepared according to M. W. Rathke et al., *J. Amer. Chem. Soc.* 95:3050 (1973)) in hexane, is added dropwise to a hexane solution of 2-cyanoethyl diisopropylchlorophosphoramidite 126 (Aldrich Chemical Company) under an inert atmosphere. The reaction mixture is washed free from salts with water. The resultant organic layer is dried over anhydrous sodium sulfate, filtered, reduced in volume, and phosphoramidite 127 is isolated by column chromatography on silica gel by elution with hexane and dichloromethane.

Phosphoramidite 127 is dissolved in dry acetonitrile and placed under an inert atmosphere. To this solution is added an acetonitrile solution of 1.2 equivalents of 2-(trifluoroacetamido)ethanol 128 and 1.2 equivalents of tetrazole. The product phosphonite 129 is isolated by column chromatography on silica gel by elution with hexane and dichloromethane.

Phosphonite 129 is dissolved in dry dichloromethane. To the solution is added 1.5 equivalents of tert-butyl hydroperoxide (TBHP) in dichloromethane. After complete reaction, the excess TBHP is removed from the reaction mixture by washing with water. The resultant organic layer is dried over anhydrous sodium sulfate, filtered, reduced in volume, and the phosphonate diester product 130 is isolated by column chromatography on silica gel by elution with hexane and dichloromethane.

Phosphonate diester 130 is dissolved in dichloromethane, and 2 equivalents of tri-fluoroacetic acid (TFA) are added. After the reaction is complete, the excess TFA is removed by washing with water. The resultant organic layer is dried over anhydrous sodium sulfate, filtered, reduced in volume, and the phosphonate diester carboxylic acid 131 is isolated by column chromatography on silica gel by elution with methanol and acetic acid in dichloromethane.

Phosphonate diester 131 is dissolved in ethyl acetate. To the solution is added N-hydroxysuccinimide (NHS, 2 eq.) and dicyclohexylcarbodiimide (DCC, 1.2 eq.). After the reaction is complete, dicyclohexylurea is removed by filtration, and excess NHS is removed by washing with water. The resultant organic layer is dried over anhydrous sodium sulfate, filtered, reduced in volume, and the phosphonate NHS ester 132 is isolated by column chromatography on silica gel by elution with hexane and dichloromethane.

Phosphonate NHS ester 132 is added to nucleotide 8 (Example 1) in NaHCO$_3$ buffer to afford nucleotide 133. After the cyanoethyl and TFA group are removed by treatment with ammonium hydroxide, the resultant nucleotide amine 134 is coupled to dye-NHS ester 11 (Example 1) to afford the expected dye-labeled nucleotide 135. The Fmoc group is removed, and the amine product 136 is coupled with dye-NHS ester 14 (Example 1) to afford dye-nucleotide conjugate 137.

Example 17

Synthesis of Dye-NHS Ester 14

Bicyclic amine t-Boc ester 141 (12.8 gm, 47 mmole, U.S. Pat. No. 5,688,808), 1-bromo-3-chloropropane (29.3 gm, 187 mmole), sodium iodide (56.4 gm, 376 mmole) and sodium bicarbonate (7.9 gm, 94 mmole) were refluxed together in 150 ml CH$_3$CN for 18 hours. The mixture was cooled to room temperature, filtered, and evaporated. The filter cake was washed with 300 ml hexane which was combined with the filtrate and washed with 2×50 ml water and 50 ml saturated NaCl, dried over MgSO$_4$, filtered, and concentrated under vacuum. The product was purified by chromatography on silica gel, eluting with hexane/ethyl acetate: 20/1, to give tricyclic amine pivalate ester 142 (pale yellow oil, 9.5 gm, 30 mmole, 64% yield). The ester group of 142 was hydrolyzed in a solution of lithium hydroxide monohydrate (2.6 gm, 60 mmole) in 15 ml water and 120 ml methanol. After stirring for one hour at room temperature, the mixture was concentrated under vacuum, dissolved in 30 ml 1M HCl, and extracted with 3×100 ml of diethylether. The combined ether extracts were washed with 50 ml of 200 mM pH 7 phosphate buffer, dried over MgSO$_4$, filtered and concentrated under vacuum to give tricyclic amine 143 as a brown solid. Tricyclic amine 143 and 3,6-dichloro, 4-isopropylcarboxylate phthalic anhydride 144 were refluxed in toluene to give Friedel-Craft acylation product ketone 145 (Abs. max 400 nm). Cyclization of 145 with 143 in phosphoryl trichloride (as activating agent) and chloroform at reflux gave dye isopropyl carboxylic ester 146 as a mixture of isopropylcarboxylate regioisomers. After cleavage of the isopropyl group, dye carboxylic acid 147 was converted to NHS-rhodamine dye 14 (which can be used in Example 1).

Example 18

Synthesis of Dye-Nucleotide Conjugate 211

To a solution of 4-bromoisophthalic acid 201 (10 g, 40.8 mmol) in methanol (150 mL) was added concentrated sulfuric acid (3.5 mL). The solution mixture was heated at reflux temperature for 24 hours. After the reaction was complete, the methanol solvent was removed under reduced pressure. The residue was made basic with saturated sodium bicarbonate (NaHCO$_3$). The solution was extracted with ethyl acetate. The extract was washed with water and dried over sodium sulfate (Na$_2$SO$_4$). Removal of solvent gave oil, which solidified at ambient temperature. The solid was titurated twice with 20 mL of methanol and hexane (1:3) to give 8 g (90%) of 4-bromoisophthalic acid dimethyl ester 202: $^1$H NMR (400 MHz, CDCl$_3$) δ 3.93 (s, 3H), 3.93 (s, 3H), 7.74 (d, J=8 Hz, 1H), 7.95 (dd, J=2 Hz, J=8 Hz, 1H), 8.43 (d, J=2 Hz, 1H).

To a solution of 4-bromoisophthalic acid dimethyl ester 202 (2.95 g, 10.8 mmol) in anhydrous DMF (50 ml), Copper (I) cyanide (1.20 g, 13.5 mmol) was added in one portion. The slurry solution was heated at reflux temperature for one hour. When the solution was cooled to ambient temperature, it was poured into 300 mL of ammonium chloride solution (10%) at 0° C. White precipitate was formed. The slurry solution was stirred at ambient temperature for 30 minutes. Then it was extracted with ethyl acetate. The combined extracts were dried over sodium sulfate. Removal of solvent gave white solid which was washed with cold methanol to give 1.89 g (80%) of 4-cyanoisophthalic acid dimethyl ester 203: $^1$H NMR (400 MHz, CDCl$_3$) δ 3.95 (s, 3H), 4.05 (s, 3H), 7.91 (d, J=8 Hz, 1H), 8.30 (dd, J=1.7 Hz, J=8 Hz, 1H), 8.77 (d, J=1.7 Hz, 1H).

4-Cyanoisophthalic acid dimethyl ester 203 (1.70 g, 7.76 mmol) was dissolved in methanol (100 mL) and then treated with an aqueous solution of lithium hydroxide (2.0 g, 46.5 mmol) in 50 mL of water. The basic solution was stirred at ambient temperature for 1.5 hour. It was then poured into a 10% HCl solution. The solution was extracted with ethyl acetate and the combined extracts were dried over Na$_2$SO$_4$. Removal of solvent gave quantitative yield of 4-cyanoisophthalic acid 204: $^1$H NMR (400 MHz, CD$_3$OD) δ 8.01 (d, J=8 Hz, 1H), 8.33 (dd, J=1.7 Hz, J=8 Hz, 1H), 8.73 (d, J=1.7 Hz, 1H).

A pressure flask was charged with 4-cyanoisophthalic acid 204 (1.40 g, 7.33 mmol), ethanol (100 mL), Pd/C (10%) (0.50 mg), and concentrated HCl (1.5 mL). The mixture solution was hydrogenated at 50 PSI overnight. The solid impurities were removed by filtration. Removal of solvent gave quantitative yield of 4-aminomethylisophthalic acid 205: $^1$H NMR (400 MHz, CD$_3$OD) δ 4.46 (s, 2H), 7.69 (d, J=8 Hz, 1H), 8.26 (dd, J=2 Hz, J=8 Hz, 1H), 8.76 (d, J=1.7 Hz, 1H).

A round bottom flask was charged with 4-aminomethylisophthalic acid 205, ethanol (20 mL), methanol (20 mL), excess ethyl trifluoroacetate (20 mL), and triethylamine (10 mL). The mixture solution was stirred at ambient temperature for 1 hour. It was then poured into a hydrochloric acid solution (10%). The solution was extracted with ethyl acetate. The combined extracts were dried over Na$_2$SO$_4$. Removal of solvent gave compound 206 (1.8 g): $^1$H NMR (400 MHz, CD$_3$OD) δ 4.9 (s, 2H), 7.51 (d, J=8 Hz, 1H), 8.17 (dd, J=2 Hz, J=8 Hz, 1H), 8.65 (d, J=2 Hz, 1H).

A 100 mL, round bottom flask was charged with crude compound 206 (1 g, 3.43 mmol), anhydrous DMF (30 mL), O-(N-succinimidyl)-N,N,N',N'-tetramethyluronium tetrafluoroborate (1 g, 3.43 mmol), and diisopropylethylamine (1.3 g, 10.3 mmol). The reaction solution was stirred at ambient temperature for 30 minutes. Solvent was removed under reduced pressure. The crude compound was added 5% HCl solution and was extracted with ethyl acetate. The combined organic extracts were dried over Na$_2$SO$_4$. Purification was achieved by flash column chromatography on silica gel with eluent CH$_2$Cl$_2$:CH$_3$OH (10:1) followed by CH$_2$Cl$_2$:CH$_3$OH (5:1) to afford 500 mg (38%) of activated ester 207: H$^1$NMR (400 MHz, CDCl$_3$+10% CD$_3$OD) δ 2.93 (s, 4H), 4.80 (s, 2H)), 7.60 (d, J=8 Hz, 1H), 8.17 (dd, J=2 Hz, J=8 Hz, 1H), 8.7.0 (d, J=2 Hz, 1H); $^{19}$F NMR–178 ppm (s).

Compound 208 (which is the same as compound 58 noted in Example 9) (1 equiv) was dissolved in a minimum amount of formamide and a solution of linker synthon 207 (7 equiv) in DMSO (1 mg of 207 per 5 μL of DMSO) was added, followed by diisopropylethylamine (20 equiv). The coupling reaction was complete in one hour at ambient temperature. Purification was carried out by HPLC (AX-300 anion exchange). The recovered compound was dried under reduced pressure and purified by HPLC (C-18 reverse phase). The compound was dried under reduced pressure and then heated in ammonium hydroxide (28-30%) for 15 minutes at 55° C. Then it was dried and purified by HPLC (C-18 reverse phase) to give nucleotide 209.

Figure 22B:
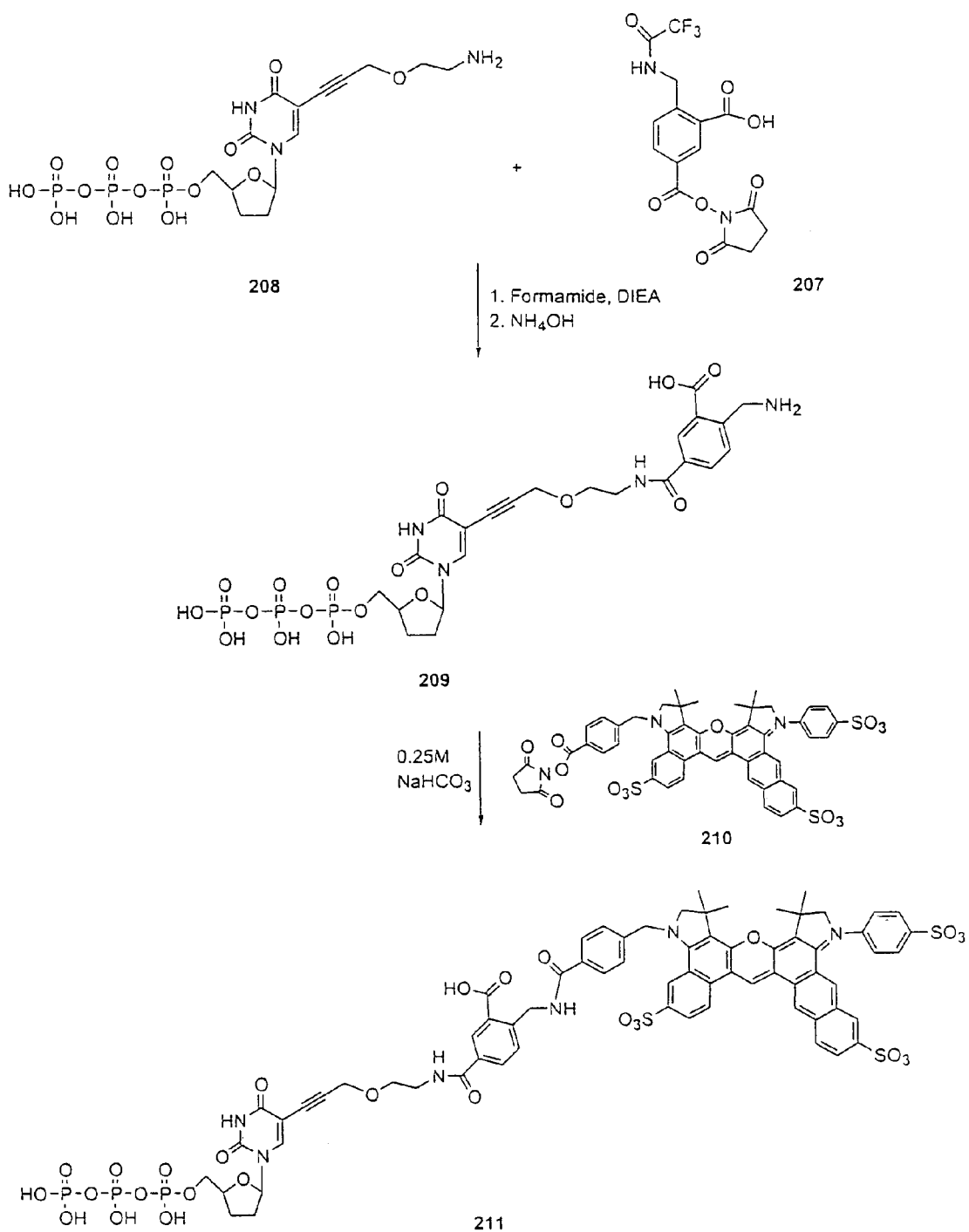

The following can be used as a general procedure to produce dye conjugates from compound 209 and an activated ester, such as an NHS ester of a dye (referred to as "NHS dye" in FIG. 22B). Compound 209 (1 equiv) is suspended in a minimum amount of a solution of 250 mM bicarbonate (pH 9.0), and a solution of dye NHS ester 210 in DMSO (3 equiv, 1 mg of dye NHS ester per 12 μL of DMSO) is then added. The reaction mixture is placed in the dark at ambient temperature for 1 hour. The product can be purified by anion exchange HPLC (AX-300) and then C-18 reverse phase HPLC to give pure dye-labeled nucleotide 211.

All publications and patent applications mentioned herein are hereby incorporated by reference as if each publication or patent application was specifically and individually indicated to be incorporated by reference.

Although the invention has been described with reference to certain illustrative embodiments and examples, it will be appreciated that various modifications and variations can be made without departing from the scope and spirit of the invention.

The invention claimed is:

1. A conjugate comprising a dye labeled nucleobase of the form:
   (1) B-L-D, wherein B is a nucleobase, L is an anionic linker, and D comprises at least one fluorescent dye that comprises a xanthene, a rhodamine or a fluorescein, or (2) B-L1-D1-L2-D2, wherein B is a nucleobase, L1 and L2 are linkers such that at least one of L1 and L2 is an anionic linker, and D1 and D2 are members of a fluorescent donor/acceptor pair, such that one of D1 and D2 is a donor dye capable of absorbing light at a first wavelength and emitting energy in response thereto, and the other of D1 and D2 is an acceptor dye capable of absorbing energy emitted by the donor dye and fluorescing at a second wavelength in response thereto, and at least one of D1 and D2 comprises a xanthene, a rhodamine or a fluorescein, wherein B comprises adenine, 7-deazaadenine, 7-deaza-8-azaadenine, cytosine, guanine, 7-deazaguanine, 7-deaza-8-azaguanine, thymine, uracil, or inosine, and wherein L or at least one of L1 and L2 comprises at least one anionic phosphate or anionic phosphonate, and comprises 4 to 20 chain atoms.

2. The conjugate of claim 1, wherein the labeled nucleobase is of the form B-L1-D1-L2-D2.

3. The conjugate of claim 2, wherein D1 is a donor dye and D2 is an acceptor dye.

4. The conjugate of claim 2, wherein at least one of D1 or D2 comprises at least one xanthene dye.

5. The conjugate of claim 2, wherein at least one of D1 or D2 comprises at least one rhodamine dye.

6. The conjugate of claim 2, wherein at least one of D1 or D2 comprises at least one fluorescein dye.

7. The conjugate of claim 1, wherein the dye-labeled nucleobase is of the form B-L-D.

8. The conjugate of claim 7, wherein D comprises at least one xanthene dye.

9. The conjugate of claim 7, wherein D comprises at least one rhodamine dye.

10. The conjugate of claim 7, wherein D comprises at least one fluorescein dye.

* * * * *